US009365634B2

(12) United States Patent
Béliveau et al.

(10) Patent No.: US 9,365,634 B2
(45) Date of Patent: *Jun. 14, 2016

(54) APROTININ-LIKE POLYPEPTIDES FOR DELIVERING AGENTS CONJUGATED THERETO TO TISSUES

(75) Inventors: Richard Béliveau, Montréal (CA); Michel Demeule, Beaconsfield (CA); Christian Che, Montréal (CA); Anthony Regina, Montréal (CA)

(73) Assignee: Angiochem Inc., Montreal (CA)

( * ) Notice: Subject to any disclaimer, the term of this patent is extended or adjusted under 35 U.S.C. 154(b) by 1074 days.

This patent is subject to a terminal disclaimer.

(21) Appl. No.: 12/601,803

(22) PCT Filed: May 29, 2008

(86) PCT No.: PCT/CA2008/001030
§ 371 (c)(1),
(2), (4) Date: Aug. 2, 2010

(87) PCT Pub. No.: WO2008/144919
PCT Pub. Date: Dec. 4, 2008

(65) Prior Publication Data
US 2010/0297120 A1    Nov. 25, 2010

Related U.S. Application Data

(63) Continuation-in-part of application No. 11/807,597, filed on May 29, 2007, and a continuation-in-part of application No. 11/807,917, filed on May 30, 2007.

(60) Provisional application No. 61/008,880, filed on Dec. 20, 2007.

(51) Int. Cl.
| A61K 38/00 | (2006.01) |
| A61K 38/04 | (2006.01) |
| C07K 7/08 | (2006.01) |
| C07K 9/00 | (2006.01) |
| C07K 14/81 | (2006.01) |

(52) U.S. Cl.
CPC ............... *C07K 14/8117* (2013.01); *C07K 7/08* (2013.01); *A61K 38/00* (2013.01)

(58) Field of Classification Search
None
See application file for complete search history.

(56) References Cited

U.S. PATENT DOCUMENTS

| 3,953,417 A | 4/1976 | Konig et al. |
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,169,933 A | 12/1992 | Anderson et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,506,120 A | 4/1996 | Yamamoto et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,922,754 A | 7/1999 | Burchett et al. |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Pagé et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,306,993 B1 | 10/2001 | Rothbard et al. |

(Continued)

FOREIGN PATENT DOCUMENTS

| CA | 2283474 | 9/1998 |
| CA | 2421042 A1 | 5/2002 |

(Continued)

OTHER PUBLICATIONS

Fioretti et al (Biol Chem Hoppe-Seyler 369 37-42, 1988).*
Correspondence sharing timeline, Jun. 18, 2015.*
Timeline.*
U.S. Appl. No. 12/632,557, filed Dec. 7, 2009, Castaigne et al.
Arpicco et al., "New Coupling Reagents for the Preparation of Disulfide Cross-Linked Conjugates with Increased Stability," *Bioconjugate Chem.* 8:327-337 (1997).
Banks, "Leptin Transport Across the Blood-Brain Barrier: Implications for the Cause and Treatment of Obesity," *Curr. Pharm. Des.* 7:125-133 (2001).
Banks, "The Blood-Brain Barrier as a Cause of Obesity," *Curr. Pharm. Des.* 14:1606-1614 (2008).

(Continued)

*Primary Examiner* — Daniel E Kolker
*Assistant Examiner* — Aditi Dutt
(74) *Attorney, Agent, or Firm* — Clark & Elbing LLP; Kristina Bicker-Brady

(57) ABSTRACT

Based on our identification of a polypeptide (Angiopep-7) that is efficiently transported to cells such as liver, lung, kidney, spleen, and muscle, the invention provides polypeptides, conjugates including the polypeptides, and methods for treating diseases associated with these cell types. Unlike other aprotinin related polypeptides identified herein (including Angiopep-3, Angiopep-4a Angiopep-4b Angiopep-5, and Angiopep-6) which efficiently cross the blood-brain barrier (BBB), Angiopep-7 is not efficiently transported across the BBB.

13 Claims, 35 Drawing Sheets

(56) References Cited

U.S. PATENT DOCUMENTS

| | | |
|---|---|---|
| 6,310,039 B1 | 10/2001 | Kratz |
| 6,316,024 B1 | 11/2001 | Allen et al. |
| 6,348,207 B1 | 2/2002 | Milstein et al. |
| 6,376,648 B2 | 4/2002 | White et al. |
| 6,391,305 B1 | 5/2002 | Feng et al. |
| 6,469,047 B1 | 10/2002 | Jackson et al. |
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,689,582 B1 | 2/2004 | Davies et al. |
| 6,713,454 B1 | 3/2004 | Ekwuribe et al. |
| 6,906,033 B2 | 6/2005 | White et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,569,323 B2 | 10/2013 | Ren et al. |
| 2002/0086384 A1 | 7/2002 | Levine et al. |
| 2003/0129186 A1 | 7/2003 | Beliveau et al. |
| 2003/0170891 A1 | 9/2003 | McSwiggen |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2010/0297120 A1 | 11/2010 | Beliveau et al. |
| 2011/0059187 A1 | 3/2011 | Basu et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2011/0318322 A1 | 12/2011 | Bossard |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1* | 2/2013 | Hood et al. .................. 506/2 |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |
| 2014/0017166 A1 | 1/2014 | Hettmann et al. |
| 2015/0037311 A1 | 2/2015 | Boivin et al. |

FOREIGN PATENT DOCUMENTS

| | | |
|---|---|---|
| CA | 2525236 | 1/2005 |
| CA | 2637893 | 7/2007 |
| CA | 2638034 | 7/2007 |
| CN | 101160403 A | 4/2008 |
| CN | 101262890 A | 9/2008 |
| CN | 102406949 A | 4/2012 |
| CN | 102552928 A | 7/2012 |
| CN | 102614105 A | 8/2012 |
| DE | 2344886 A1 | 4/1975 |
| DE | 19953696 | 5/2001 |
| EP | 0 393 431 | 4/1990 |
| EP | 0393431 | 10/1990 |
| EP | 0495049 B1 | 4/1997 |
| EP | 1466924 A1 | 10/2004 |
| EP | 1982699 A1 | 10/2008 |
| EP | 2333074 A1 | 6/2011 |
| GB | 2360453 A | 9/2001 |
| JP | 2007-509977 A | 4/2007 |
| JP | 2008-529539 A | 8/2008 |
| JP | 2009-500431 A | 1/2009 |
| JP | 2011-144174 A | 7/2011 |
| RU | 2172323 C2 | 10/1999 |
| WO | WO 87/05702 | 9/1987 |
| WO | WO 96/31531 | 10/1996 |
| WO | WO 96/35788 | 11/1996 |
| WO | WO-96/39160 A1 | 12/1996 |
| WO | WO 96/39183 | 12/1996 |
| WO | WO 96/40210 | 12/1996 |
| WO | WO 97/33996 | 9/1997 |
| WO | WO-97/40160 A1 | 10/1997 |
| WO | WO 97/40854 | 11/1997 |
| WO | WO-99/46575 A2 | 9/1999 |
| WO | WO 00/01417 | 1/2000 |
| WO | WO 00/71574 | 11/2000 |
| WO | WO 01/30319 | 5/2001 |
| WO | WO 02/33090 | 4/2002 |
| WO | WO-02/43765 A2 | 6/2002 |
| WO | WO-02/085923 A2 | 10/2002 |
| WO | WO 03/009815 | 2/2003 |
| WO | WO-03/102583 A1 | 12/2003 |
| WO | WO 2004/060403 | 7/2004 |
| WO | PCT/JP2004/011668 | 8/2004 |
| WO | WO 2004/091623 | 10/2004 |
| WO | WO-2004/093897 A1 | 11/2004 |
| WO | WO-2004/108071 A2 | 12/2004 |
| WO | WO 2005/002515 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO 2006/086870 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO 2007/009229 | 1/2007 |
| WO | WO 2007/020085 | 2/2007 |
| WO | WO 2007/030619 | 3/2007 |
| WO | WO-2007/035716 A2 | 3/2007 |
| WO | WO-2007/044323 A2 | 4/2007 |
| WO | WO-2007/082978 A1 | 7/2007 |
| WO | WO-2007/082979 A1 | 7/2007 |

(56) References Cited

FOREIGN PATENT DOCUMENTS

| WO | WO 2007/103515 | 9/2007 |
|---|---|---|
| WO | WO 2007/113172 | 10/2007 |
| WO | WO 2008/012629 | 1/2008 |
| WO | WO-2008/036682 A2 | 3/2008 |
| WO | WO 2008/046228 | 4/2008 |
| WO | WO 2008/069876 | 6/2008 |
| WO | WO-2008/116171 A1 | 9/2008 |
| WO | WO 2008/144919 | 12/2008 |
| WO | WO 2009/039188 | 3/2009 |
| WO | WO 2009/046220 | 4/2009 |
| WO | WO 2009/070597 | 6/2009 |
| WO | WO 2009/079790 | 7/2009 |
| WO | WO 2009/105671 | 8/2009 |
| WO | WO 2009/127072 | 10/2009 |
| WO | WO-2010/006239 A2 | 1/2010 |
| WO | WO 2010/043047 | 4/2010 |
| WO | WO 2010/043049 | 4/2010 |
| WO | WO 2010/063123 | 6/2010 |
| WO | WO 2010/063124 | 6/2010 |
| WO | WO 2010/069074 | 6/2010 |
| WO | WO 20101063122 | 6/2010 |
| WO | WO 2010/121379 | 10/2010 |
| WO | WO 2010/142035 | 12/2010 |
| WO | WO 2011/000095 | 1/2011 |
| WO | WO-2011/008823 A2 | 1/2011 |
| WO | WO 2011/041897 | 4/2011 |
| WO | WO-2011/063507 A1 | 6/2011 |
| WO | WO-2011/112635 A1 | 9/2011 |
| WO | WO 2011/153642 | 12/2011 |
| WO | WO 2012/000118 | 1/2012 |
| WO | WO-2012/006239 A1 | 1/2012 |
| WO | WO 2012/037687 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/023184 A1 | 2/2013 |
| WO | WO-2013/032591 A1 | 3/2013 |
| WO | WO-2013/043232 A2 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |
| WO | WO-2014/028487 A1 | 2/2014 |
| WO | WO-2014/028777 A2 | 2/2014 |
| WO | WO-2014/194428 A1 | 12/2014 |
| WO | WO-2014/194429 A1 | 12/2014 |

OTHER PUBLICATIONS

Bicamumpaka et al., "In Vitro Cytotoxicity of Paclitaxel-Transferrin Conjugate on H69 Cells," *Oncol. Rep.* 5:1381-1383 (1998).

Demeule et al., "Drug Transport to the Brain: Key Roles for the Efflux Pump P-Glycoprotein in the Blood-Brain Barrier," *Vascul. Pharmacol.* 38:339-348 (2002).

Dooley et al., "An All D-amino Acid Opioid Peptide with Central Analgesic Activity from a Combinatorial Library," *Science* 266:2019-2022 (1994).

Eigenbrot et al., "X-Ray Structure of Glial Cell-Derived Neurotrophic Factor at 1.9 Å Resolution and Implications for Receptor Binding," *Nat. Struct. Biol.* 4:435-438 (1997).

Gabius et al., "Targeting of Neoglycoprotein-Drug Conjugates to Cultured Human Embryonal Carcinoma Cells," *J. Cancer Res. Clin. Oncol.* 113:126-130 (1987).

Gottschalk et al., "Protein Self-Association in Solution: The Bovine Pancreatic Trypsin Inhibitor Decamer," *Biophys. J.* 84: 3941-3958 (2003).

Harkavyi et al., "Glucagon-Like Peptide 1 Receptor Stimulation Reverses Key Deficits in Distinct Rodent Models of Parkinson's Disease," *J. Neuroinflammation.* 5:19 (2008) (pp. 1-9).

Kalra, "Central Leptin Insufficiency Syndrome: An Interactive Etiology for Obesity, Metabolic and Neural Diseases and for Designing New Therapeutic Interventions," *Peptides* 29:127-138 (2008).

Karyekar et al., "*Zonula Occludens* Toxin Increases the Permeability of Molecular Weight Markers and Chemotherapeutic Agents Across the Bovine Brain Microvessel Endothelial Cells," *J. Pharm. Sci.* 92:414-423 (2003).

Kirsch et al., "Anti-Angiogenic Treatment Strategies for Malignant Brain Tumors," *J. Neurooncol.* 50:149-163 (2000).

Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconjugate Chem.* 9:72-86 (1998).

Saito et al., "Drug Delivery Strategy Utilizing Conjugation Via Reversible Disulfide Linkages: Role and Site of Cellular Reducing Activities," *Adv. Drug. Deliv. Rev.* 55:199-215 (2003).

Samson et al., "Gene Therapy for Diabetes: Metabolic Effects of Helper-Dependent Adenoviral Exendin 4 Expression in a Diet-Induced Obesity Mouse Model," *Mol. Ther.* 16:1805-1812 (2008) (pp. 1-18).

Uekita et al., "Cytoplasmic Tail-Dependent Internalization of Membrane-Type 1 Matrix Metalloproteinase is Important for its Invasion-Promoting Activity," *J. Cell. Biol.* 155:1345-1356 (2001).

Uekita et al., "Membrane-Type 1 Matrix Metalloproteinase Cytoplasmic Tail-Binding Protein-1 is a New Member of the Cupin Superfamily. A Possible Multifunctional Protein Acting as an Invasion Suppressor Down-Regulated in Tumors," *J. Biol. Chem.* 279:12734-12743 (2004).

Akhtar et al., "Nonviral Delivery of Synthetic siRNAs in Vivo," *J. Clin. Invest.* 117: 3623-3632 (2007).

Anonymous, "Blood-Brain Barrier Tackled," <http:www.ecancermedicalscience.com/news-insider-news.asp?itemId=326> Oct. 22, 2008.

Bertrand et al., "Transport Characteristics of a Novel Peptide Platform for CNS Therapeutics," *J. Cell Mol. Med.* published online Oct. 10, 2009.

Boules et al., "Bioactive Analogs of Neurotensin: Focus on CNS Effects," *Peptides* 27: 2523-2533 (2006).

Chari, "Targeted Cancer Therapy: Conferring Specificity to Cytotoxic Drugs," *Acc. Chem. Res.* 41:98-107 (2008).

Ché et al., "New Angiopep-Modified Doxorubicin (ANG1007) and Etoposide (ANG1009) Chemotherapeutics with Increased Brain Penetration," *J. Med. Chem.* 53: 2814-2824 (2010).

Demeule et al., "Involvement of the Low-Density Lipoprotein Receptor-Related Protein in the Transcytosis of the Brain Delivery Vector Angiopep-2," *J. Neurochem.* 106: 1534-1544 (2008).

Garsky et al., "The Synthesis of a Prodrug of Doxorubicin Designed to Provide Reduced Systemic Toxicity and Greater Target Efficacy," *J. Med. Chem.* 44: 4216-4224 (2001).

Huang et al., "Targeting Delivery of Paclitaxel into Tumor Cells via Somatostatin Receptor Endocytosis," *Chem. Biol.* 7: 453-461 (2000).

Kilic et al., "Intravenous TAT-GDNF is Protective after Focal Cerebral Ischemia in Mice," *Stroke* 34: 1304-1310 (2003).

Kumar et al., "Transvascular Delivery of Small Interfering RNA to the Central Nervous System," *Nature* 448: 39-43 (2007).

Rousselle et al., "New Advances in the Transport of Doxorubicin through the Blood-Brain Barrier by a Peptide Vector-Mediated Strategy," *Mol. Pharmacol.* 57: 679-686 (2000).

Takei et al., "A Small Interfering RNA Targeting Vascular Endothelial Growth Factor as Cancer Therapeutics," *Cancer Res.* 64: 3365-3370 (2004).

Trail et al., "Cure of Xenografted Human Carcinomas by BR96-Doxorubicin Immunoconjugates," *Science* 261:212-215 (1993).

U.S. Appl. No. 61/546,851, filed Oct. 13, 2011, Demeule et al.

(56) References Cited

OTHER PUBLICATIONS

Grimm et al., "Ten Year Biochemical Outcomes Following 125-Iodine Monotherapy for Early Stage Prostate Cancer." *Int. J. Radiation Oncology Biol.Phys.* 48:146-147 (2000).
Kurzrock et al., "ANGI005: Results of a Phase I study in patients with advanced solid tumors and metastatic brain cancer" Poster B168, ACCR/NCI/EORTC Annual Meeting, 2009.
Mathupala, "Delivery of Small-interfering RNA (siRNA) to the Brain," *Exp. Opin. Ther. Pat.* 19: 137-140, (2009).
Nyalendo et al., "Impaired Tyrosine Phosphorylation of Membrane type 1-Matrix Metalloproteinase Reduces Tumor Cell Proliferation in Three-Dimensional Matrices and Abrogates Tumor Growth in Mice," *Carcinogenesis* 29:1655-1664, (2008).
Sadeghi-aliabadi et al., "Solvent optimization on Taxol extraction from *Taxus baccata L.*, using HPLC and LC-MS," *DARU* 17:192-198, (2009).
Schiff and Horwitz, "Taxol Stabilizes Microtubules in Mouse Fibroblast Cells," *Proc Natl Acad Sci USA* 77:1561-1565, (1980).
Tilstra et al., "Protein Transduction: Identification, Characterization and Optimization," *Biochem. Soc. Trans.* 35:811-815, (2007).
Zhang et al., "Tat-modified Leptin is more Accessible to Hypothalamus Through Brain-blood Barrier with a Significant Inhibition of Body-weight Gain in High-fat-diet Fed Mice," *Exp. Clin. Endocrin. Diabet.* 118:31-37 (2010).
International Search Report and Written Opinion of the International Search Authority for Application No. PCT/CA2008/001030, mailed Sep. 15, 2008.
Ballabh et al., "The Blood-Brain Barrier: An Overview Structure, Regulation, and Clinical Implications," *Neurobiol Dis.* 16:1-13 (2004).
Bickel et al., "Delivery of Peptides and Proteins Through the Blood-Brain Barrier," *Adv Drug Deliv Rev.* 46:247-279 (2001).
Boado, "Blood-brain Barrier Transport of Non-viral Gene and RNAi Therapeutics," *Pharm Res.* 24:1772-1787 (2007).
Bork, "Powers and Pitfalls in Sequence Analysis: The 70% Hurdle," *Genome Res.* 10:398-400 (2000).
Bork et al., "Go Hunting in Sequence Databases But Watch Out for the Traps," *Trends Genet.* 12:425-427 (1996).
Brenner, "Errors in Genome Annotation," *Trends Genet.* 15:132-133 (1999).
Castex et al., "2-Pyrrolinodoxorubicin and Its Peptide-vectorized Form Bypass Multidrug Resistance," *Anticancer Drugs.* 15:609-617 (2004).
Coon et al., "Solutol HS 15, Nontoxic Polyoxyethylene Esters of 12-hydroxystearic Acid, Reverses Multidrug Resistance," *Cancer Res.* 51:897-902 (1991).
D'Onofrio et al., "Glycomimetics as Decorating Motifs for Oligonucleotides: Solid-phase Synthesis, Stability, and Hybridization Properties of Carbopeptoid-oligonucleotide Conjugates," *Bioconjug Chem.* 16:1299-1309 (2005).
Dagenais et al., "Development of an in Situ Mouse Brain Perfusion Model and Its Application to mdr1a P-glycoprotein-deficient Mice," *J Cereb Blood Flow Metab.* 20:381-386 (2000).
Deane et al., "LRP/Amyloid β-Peptide Interaction Mediates Differential Brain Efflux of Aβ Isoforms," *Neuron.* 43:333-344 (2004).
Dehouck et al., "A New Function for the LDL Receptor: Transcytosis of LDL Across the Blood-Brain Barrier," *J Cell Biol.* 138:877-889 (1997).
Dehouck et al., "An Easier, Reproducible, and Mass-production Method to Study the Blood-brain Barrier in Vitro," *J Neurochem.* 54:1798-1801 (1990).
Dehouck et al., "Drug Transfer Across the Blood-Brain Barrier: Correlation Between in Vitro and in Vivo Models," *J Neurochem.* 58:1790-1797 (1992).
Demeule et al., "High Transcytosis of Melanotransferrin (P97) Across the Blood-Brain Barrier," *J Neurochem.* 83:924-933 (2002).
Demeule et al., "Identification and Design of Peptides As a New Drug Delivery System for the Brain," *J Pharmacol Exp Ther.* 324:1064-1072 (2008).
Demeule et al., "Isolation of Endothelial Cells from Brain, Lung, and Kidney: Expression of the Multidrug Resistance P-Glycoprotein Isoforms," *Biochem Biophys Res Commun.* 281:827-834 (2001).
Doerks et al., "Protein Annotation: Detective Work for Function Prediction," *Trends Genet.* 14:248-250 (1998).
Fillebeen et al., "Receptor-Mediated Transcytosis of Lactoferrin Through the Blood-Brain Barrier," *J Biol Chem.* 274:7011-7017 (1999).
Fromm, "P-glycoprotein: A Defense Mechanism Limiting Oral Bioavailability and CNS Accumulation of Drugs," *Int J Clin Pharmacol Ther.* 38:69-74 (2000).
Gelmon, "The Taxoids: Paclitaxel and Docetaxel," *Lancet.* 344:1267-1272 (1994).
Gewirtz, "A Critical Evaluation of the Mechanisms of Action Proposed for the Antitumor Effects of the Anthracycline Antibiotics Adriamycin and Daunorubicin," *Biochem Pharmacol.* 57:727-741 (1999).
Grabb et al., "Neoplastic and Pharmacological Influence on the Permeability of an in vitro Blood-Brain Barrier," *J Neurosurg.* 82:1053-1058 (1995).
Guillot et al., "Angiotensin Peptide Regulation of Bovine Brain Microvessel Endothelial Cell Monolayer Permeability," *J Cardiovasc Pharmacol.* 18:212-218 (1991).
Gumbleton et al., "Progress and Limitations in the Use of in Vitro Cell Cultures to Serve as a Permeability Screen for the Blood-Brain Barrier," *J Pharm Sci.* 90:1681-1698 (2001).
Hawkins et al., "The Blood-Brain Barrier/Neurovascular Unit in Health and Disease," *Pharmacol Rev.* 57:173-185 (2005).
Hussain et al., "The Mammalian Low-Density Lipoprotein Receptor Family," *Annu Rev Nutr.* 19:141-172 (1999).
Ito et al., "Functional Characterization of the Brain-to-Blood Efflux Clearance of Human Amyloid-β Peptide (1-40) Across the Rat Blood-Brain Barrier," *Neurosci Res.* 56:246-252 (2006).
Ke et al., "Gene Delivery Targeted to the Brain Using an Angiopep-conjugated Polyethyleneglycol-modified Polyamidoamine Dendrimer," *Biomaterials.* (2009) (Epub ahead of print).
Kiernan et al., "Fluorescent—Labelled Aprotinin: A New Reagent for the Histochemical Detection of Acid Mucosubstances," *Histochemie.* 34: 77-84 (1973).
Kobayashi et al., "The Protease Inhibitor Bikunin, a Novel Anti-Metastatic Agent," *Biol Chem.* 384:749-754 (2003).
Koo et al., "Differential Expression of Amyloid Precursor Protein mRNAs in Cases of Alzheimer's Disease and in Aged Nonhuman Primates," *Neuron.* 2:97-104 (1990).
Kounnas et al, "LDL Receptor-related Protein, a Multifunctional ApoE Receptor, Binds Secreted Beta-amyloid Precursor Protein and Mediates Its Degradation," *Cell.* 82:331-340 (1995).
Koziara et al., "In Situ Blood-brain Barrier Transport of Nanoparticles," *Pharm Res.* 20:1772-1778 (2003).
Kreuter et al., "Apolipoprotein-Mediated Transport of Nanoparticle-Bound Drugs Across the Blood-Brain Barrier," *J Drug Target.* 10:317-325 (2002).
Kreuter et al., "Direct Evidence that Polysorbate-80-coated Poly(Butylcyanoacrylate) Nanoparticles Deliver Drugs to the CNS Via Specific Mechanisms Requiring Prior Binding of Drug to the Nanoparticles," *Pharm Res.* 20:409-416 (2003).
Kreuter, "Nanoparticulate Carriers for Drug Delivery to the Brain," Nanoparticles as Drug Carriers, Torchilin VP, Imperial College Press, London pp. 527-547 (2006).
Laccabue et al., "A Novel Taxane Active against an Orthotopically Growing Human Glioma Xenograft," *Cancer.* 92:3085-3092 (2001).
Lai et al., "The Critical Component to Establish in vitro BBB Model: Pericyte," *Brain Res Rev.* 50:258-265 (2005).
Larionova et al., "Carbohydrate-Containing Derivatives of the Trypsin-Kallikrein Inhibitor Aprotinin from Bovine Organs II. Inhibitor Coupled to the (Carboxymethyl)dextran Derivatives of D-Galactose," *Biol Chem Hoppe-Seyler.* 366:743-748 (1985).
Larsson, "Megalin, an Endocytic Receptor With Signaling Potential," *Acta Universitatis Upsaliensis Uppsala* 1-60 (2006).
Ma et al., "Cationic Charge-Dependent Hepatic Delivery of Amidated Serum Albumin," *J Control Release.* 102:583-594 (2005).

(56) References Cited

OTHER PUBLICATIONS

Marinò et al., "Megalin-Mediated Transcytosis of Thyroglobulin by Thyroid Cells is a Calmodulin-Dependent Process," *Thyroid.* 10:461-469 (2000).
Marinò et al., "Transcytosis of Retinol-Binding Protein Across Renal Proximal Tubule Cells After Megalin (gp 330)-Mediated Endocytosis," *J Am Soc Nephrol* .12:637-648 (2001).
Martel et al., "Transport of Apolipoproteins E and J at the Blood-Brain Barrier Relevance to Alzheimer's disease," *S.T P. Pharma Sciences.* 7:28-36 (1997).
Mazel et al., "Doxorubicin-peptide Conjugates Overcome Multidrug Resistance," *Anticancer Drugs.* 12:107-116 (2001).
McCarty, "Cell Biology of the Neurovascular Unit: Implications for Drug Delivery Across the Blood-Brain Barrier," *Assay Drug Dev Technol.* 3:89-95 (2005).
Moestrup et al., "Evidence that Epithelial Glycoprotein 330/Megalin Mediates Uptake of Polybasic Drugs," *J.Clin. Invest.* 96:1404-1413 (1995).
Moore et al., "The Role of Flexible Tethers in Multiple Ligand-receptor Bond Formation Between Curved Surfaces," *Biophys J.* 91:1675-1687 (2006).
Muratovska et al., "Conjugate for Efficient Delivery of Short Interfering RNA (siRNA) Into Mammalian Cells," *FEBS Lett.* 558:63-68 (2004).
Ngo et al., "Computational Complexity: Protein Structure Prediction, and the Levinthal Paradox," *The Protein Folding Problem and Tertiary Structure Prediction* Merz, Jr. and Le Grand, Eds. 491-495 (1994).
Niola et al., "A Plasmid-encoded VEGF siRNA Reduces Glioblastoma Angiogenesis and Its Combination with Interleukin-4 Blocks Tumor Growth in a Xenograft Mouse Model," *Cancer Biol Ther.* 5:174-179 (2006).
Orlando et al., "Identification of the Second Cluster of Ligand-Binding Repeats in Megalin as a Site for Receptor-Ligand Interactions," *Proc Natl Acad Sci.* 94:2368-2373 (1997).
Pan et al., "Efficient Transfer of Receptor-Associated Protein (RAP) Across the Blood-Brain Barrier," *J Cell Sci.* 117:5071-5078 (2004).
Pardridge, "Blood-Brain Barrier Biology and Methodology," *J Neurovirol.* 5:556-569 (1999).
Pardridge, "CNS Drug Design Based on Principles of Blood-Brain Barrier Transport," *J Neurochem.* 70:1781-1792 (1998).
Pardridge, "Drug Targeting to the Brain," *Pharm Res.* 24:1733-1744 (2007).
Peri et al., "D-Glucose as a Regioselectively Addressable Scaffold for Combinatorial Chemistry on Solid Phase," *J Carbohydr Chem.* 22:57-71 (2003).
Prince et al., "Lipoprotein Receptor Binding, Cellular Uptake, and Lysosomal Delivery of Fusions Between the Receptor-Associated protein (RAP) and α-L-Iduronidase or Acid α-Glucosidase," *J Biol Chem.* 279:35037-35046 (2004).
Qu et al., "Carbohydrate-based Micelle Clusters Which Enhance Hydrophobic Drug Bioavailability by Up to 1 Order of Magnitude," *Biomacromolecules.* 7:3452-3459 (2006).
Ramakrishnan, "The Role of P-glycoprotein in the Blood-Brain Barrier," *Einstein Q J Biol Med.* 19:160-165 (2003).
Rawat et al., "Lipid Carriers: A Versatile Delivery Vehicle for Proteins and Peptides," *Yakugaku Zasshi.* 128:269-280 (2008).
Régina et al., "Antitumour Activity of ANG1005, a Conjugate Between Paclitaxel and the New Brain Delivery Vector Angiopep-2," *Br J Pharmacol.* 155:185-197 (2008).
Régina et al., "Differences in Multidrug Resistance Phenotype and Matrix Metalloproteinases Activity Between Endothelial Cells from Normal Brain and Glioma," *J Neurochem.* 84:316-324 (2003).
Scherrmann, "Drug Delivery to Brain Via the Blood-Brain Barrier," *Vascul Pharmacol.* 38:349-354 (2002).
Schinkel, "P-Glycoprotein, S Gatekeeper in the Blood-Brain Barrier," *Adv Drug Deliv Rev.* 36:179-194 (1999).
Seidel et al., "Effects of Trasylol on the Blood-Brain Barrier in Rats," *Naunyn Schmiedebergs Arch Pharmacol.* 284:R73 (1974).

Shibata et al., "Clearance of Alzheimer's Amyloid-$\beta_{1-40}$ Peptide From Brain LDL Receptor-Related Protein-1 at the Blood-Brain Barrier," *J Clin Invest.* 106:1489-1499 (2000).
Shiiki et al., "Brain Insulin Impairs Amyloid-$\beta$(1-40) Clearance From the Brain," *J Neurosci.* 24:9632-9637 (2004).
Shimura et al., "Transport Mechanism of a New Behaviorally Highly Potent Adrenocorticotropic Hormone (ACTH) Analog, Ebiratide, through the Blood-Brain Barrier," *J Pharmacol Exp Ther.* 258:459-465 (1991).
Skolnick et al., "From Genes to Protein Structure and Function: Novel Applications of Computational Approaches in the Genomic Era," *Trends Biotechnol.* 18:34-39 (2000).
Smith, "Brain Perfusion Systems for Studies of Drug Uptake and Metabolism in the Central Nervous System," *Pharm Biotechnol.* 285-307 (1996).
Smith et al., "The Challenges of Genome Sequence Annotation or 'The Devil is in the Details'," *Nat Biotechnol.* 15:1222-1223 (1997).
Steiniger et al., "Chemotherapy of Glioblastoma in Rats Using Doxorubicin-loaded Nanoparticles," *Int J Cancer.* 109:759-767 (2004).
Tamai et al., "Structure-Internalization Relationship for Absorptive-Mediated Endocytosis of Basic Peptides at the Blood-Brain Barrier," *J Pharmacol Exp Ther.* 280:410-415 (1997).
Temsamani et al., "Vector-Mediated Drug Delivery to the Brain," *Expert Opin Biol Ther.* 1:773-782 (2001).
Terasaki et al., "New Approaches to in vitro Models of Blood-Brain Barrier Drug Transport," *Drug Discov Today.* 8:944-954 (2003).
Triguero et al., "Capillary Depletion Method for Quantification of Blood-Brain Barrier Transport of Circulating Peptides and Plasma Proteins," *J Neurochem.* 54:1882-1888 (1990).
Turner et al., "RNA Targeting With Peptide Conjugates of Oligonucleotides, siRNA and PNA," *Blood Cells Mol Dis.* 38:1-7 (2007).
Veronese et al., "PEGylation, Successful Approach to Drug Delivery," *Drug Discov Today.* 10:1451-1458 (2005).
Wang et al., "DNA/dendrimer Complexes Mediate Gene Transfer into Murine Cardiac Transplants ex Vivo," *Mol Ther.* 2:602-608 (2000).
Wells, "Additivity of Mutational Effects in Proteins," *Biochemistry.* 29:8509-8517 (1990).
Witt et al., "Peptide Drug Modifications to Enhance Bioavailability and Blood-Brain Barrier Permeability," *Peptides.* 22:2329-2343 (2001).
Xu et al., "In Vitro and in Vivo Evaluation of Actively Targetable Nanoparticles for Paclitaxel Delivery," *Int J Pharm.* 288:361-368 (2005).
Yepes et.al., "Tissue-Type Plasminogen Activator Induces Opening of the Blood-Brain Barrier Via the LDL Receptor-Related Protein," *J Clin Invest.* 112:1533-1540 (2003).
Zhang et al., "Intravenous RNA Interference Gene Therapy Targeting the Human Epidermal Growth Factor Receptor Prolongs Survival in Intracranial Brain Cancer," *Clin Cancer Res.* 10:3667-3677 (2004).
Zhang et al., "Silencing the Epidermal Growth Factor Receptor Gene with RNAi may be Developed as a Potential Therapy for Non Small Cell Lung Cancer," *Genet Vaccines Ther.* 3 (2005).
Zhang et al., "siRNA-containing Liposomes Modified with Polyarginine Effectively Silence the Targeted Gene," *J Control Release.* 112:229-239 (2006).
Zlokovic et al., "Glycoprotein 330/Megalin: Probable Role in Receptor-mediated Transport of Apolipoprotein J Alone and in a Complex With Alzheimer Disease Amyloid β at the Blood-Brain and Blood Cerebrospinal Fluid Barriers," *Proc Nati Acad Sci U S A.* 93:4229-4234 (1996).
Communication and Supplementary European Search Report for EP 08 75 7166, dated May 10, 2010.
International Search Report for PCT/CA2008/001030, mailed on Sep. 15, 2008.
Written Opinion of the International Searching Authority for PCT/CA2008/001030, mailed on Sep. 15, 2008.
European Search Report for European Application No. 14001676.7, dated Sep. 8, 2014 (7 pages).
U.S. Appl. No. 61/138,375, Beliveau et al.

(56) References Cited

OTHER PUBLICATIONS

Author manuscript of Howes et al., "Rapid induction of therapeutic hypothermia using convective-immersion surface cooling: Safety, efficacy and outcomes," published in final edited form as: Resuscitation. 81(4):388-392 (2010); (13 pages).
Barakat et al., "Modulation of p-glycoprotein function by caveolin-1 phosphorylation," J Neurochem. 101(1):1-8 (2007).
Becker, "Putative antigenic domains in glycoprotein G of rabies virus: is the RGK sequence involved in virus adsorption to cellular receptors?," Virus Genes. 3(3):277-84 (1990).
Belkin et al., "Matrix-dependent proteolysis of surface transglutaminase by membrane-type metalloproteinase regulates cancer cell adhesion and locomotion," J Biol Chem. 276(21):18415-18422 (2001).
Boado et al., "GDNF fusion protein for targeted-drug delivery across the human blood-brain barrier," Biotechnol Bioeng. 100(2):387-96 (2008).
Brady et al., "Drug design. Refelections on a peptide." Nature. 368(6473):692-693 (1994).
Buvanendran et al., "Recent advances in nonopioid analgesics for acute pain management," Tech Reg Anesth Pain Man. 1 1(1):19-26 (2007).
Carell et al., "A novel procedure for the synthesis of libraries containing small organic molecules," Angew Chem Int Ed Engl. 33(20):2059-2061 (1994).
Carell et al., "A solution-phase screening procedure for the isolation of active compounds from a library of molecules," Angew Chem Int Ed Engl. 33(20):2061-2064 (1994).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261:1303-1305 (1993).
Chu et al., "$^1$H NMR spectra of diastereomeric aromatic dipeptides (Phe-Phe) in aqueous solution," Magn Reson Chem. 23(6):450-3 (1985).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmacol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Demeule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
DeWitt et al., "'Diversomers': an approach to nonpeptide, nonoligomeric chemical diversity," Proc Natl Acad Sci U S A. 90(15):6909-6913 (1993).
Erb et al., "Recursive deconvolution of combinatorial chemical libraries," Proc Natl Acad Sci U S A. 91(24):11422-11426 (1994).
Evans et al., "Design of nonpeptidal ligands for a peptide receptor: Cholecystokinin antagonists," J Med Chem. 30(7):1229-1239 (1987).
Fauchere et al., "Association with HeLa cells of campylobacter jejuni and campylobacter coli isolated from human feces," Infect Immun. 54(2):283-287 (1986).
Fodor et al., "Multiplexed biochemical assays with biological chips," Nature. 364(6437):555-556 (1993).
Furuta et al., "Structure-antinociceptive activity studies with neurotensin," Br J Pharmacol. 83(1):43-48 (1984).
Gabathuler, "Approaches to transport therapeutic drugs across the blood-brain barrier to treat brain diseases," Neurobiol Dis. 37(1):48-57 (2010).
Gallop et al., "Applications of combinatorial technologies to drug discovery. 1. Background and peptide combinatorial libraries," J Med Chem. 37(9):1233-1251 (1994).
Halab et al., "Design, synthesis, and conformational analysis of azacycloalkane amino acids as conformationally constrained probes for mimicry of peptide secondary structures," Biopolymers. 55(2):101-122 (2000).
Hanessian et al., "Synthesis of (4$S$)-hydroxymethyl-(2$R$)-(2-propyl)-butyrolactone: A quest for a practical route to an important hydroxyethylene isostere chiron," Tetrahedron. 53(18):6281-6294 (1997).
Hein et al., "Click chemistry, a powerful tool for pharmaceutical sciences," Pharm Res. 25(10):2216-2230 (2008).
Henderson et al., "Terminal amino acid sequences and proteolytic cleavage sites of mouse mammary tumor virus env gene products," J Virol. 48(1):314-9 (1983).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpression of cyclooxygenase-2 and matrix metalloproteinases in human aortic atherosclerotic lesions," Yonsei Med J. 41(1):82-88 (2000).
Hotary et al., "Membrane type I matrix metalloproteinase usurps tumor growth control imposed by the three-dimensional extracellular matrix," Cell. 114(1):33-45 (2003).
Huang et al., "Production of bioactive human beta-defensin 5 and 6 in *Escherichia coli* by soluble fusion expression," Protein Expr Purif. 61(2):168-174 (2008).
Hudson et al., "Methionine enkephalin and isosteric analogues. I. Synthesis on a phenolic resin support," Int J Pept Protein Res. 14(3):177-185 (1979).
Imai et al., "Expression of membrane-type 1 matrix metalloproteinase and activation of progelatinase A in human osteoarthritic cartilage," Am J Pathol. 151(1):245-256 (1997).
Itoh et al., "MT1-MMP: a potent modifier of pericellular microenvironment," J Cell Physiol. 206(1):1-8 (2006).
Jameson et al., "A rationally designed CD4 analogue inhibits experimental allergic encephalomyelitis," Nature. 368(6473):744-746 (1994).
Jiang et al., "Tumor cell targeting of transferrin-PEG-TNF-alpha conjugate via a receptor-mediated delivery system: design, synthesis, and biological evaluation," Bioconjug Chem. 18(1):41-9 (2007).
Jodoin et al., "P-glycoprotein in blood-brain barrier endothelial cells: interaction and oligomerization with caveolins," J Neurochem. 87(4):1010-23 (2003).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and celecoxib for newly diagnosed glioblastoma in adults," Neuro Oncol. 10(3):300-308 (2008).
Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 58(11):691-7 (1999).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012).

(56) References Cited

OTHER PUBLICATIONS

Lam et al., A new type of synthetic peptide library for identifying ligand-binding activity, Nature. 354(6348):82-4 (1991).
Lam, "Application of combinatorial library methods in cancer research and drug discovery," Anticancer Drug Des. 12(3):145-67 (1997).
Langer, "New methods of drug delivery," Science. 249(4976):1527-33 (1990).
Li et al., "Expression of alpha2-macroglobulin receptor/low density lipoprotein receptor-related protein on surfaces of tumour cells: a study using flow cytometry," Cancer Lett. 111(1-2):199-205 (1997).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Markman et al., "Phase II trial of weekly single-agent paclitaxel in platinum/paclitaxel-refractory ovarian cancer," J Clin Oncol. 20(9):2365-9 (2002).
Martinez-Fong et al., "Neurotensin-SPDP-poly-L-lysine conjugate: a nonviral vector for targeted gene delivery to neural cells," Molecular Brain Research 69:249-262 (1999).
Michaud et al., "Risks and benefits of taxanes in breast and ovarian cancer," Drug Saf. 23(5):401-28 (2000).
Moase et al., "Anti-MUC-1 immunoliposomal doxorubicin in the treatment of murine models of metastatic breast cancer," Biochim Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).
Nam et al., "Sterically stabilized anti-G(M3), anti-Le(x) immunoliposomes: targeting to B16BL6, HRT-18 cancer cells," Oncol Res. 11(1):9-16 (1999).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Oldendorf, "Stereospecificity of blood-brain barrier permeability to amino acids," Am J Physiol. 224(4):967-9 (1973).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Park et al., "Development of anti-p185HER2 immunoliposomes for cancer therapy," Proc Natl Acad Sci U S A. 92(5):1327-31 (1995).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Powell et al., "Peptide stability in drug development. II. Effect of single amino acid substitution and glycosylation on peptide reactivity in human serum," Pharm Res. 10(9):1268-73 (1993).
Rajavashisth et al., "Membrane type 1 matrix metalloproteinase expression in human atherosclerotic plaques: evidence for activation by proinflammatory mediators," Circulation. 99(24):3103-9 (1999).
Rizo et al. "Constrained peptides: models of bioactive peptides and protein substructures," Annu Rev Biochem. 61:387-418 (1992).
Rose et al., "Metastatic patterns in histologic variants of ovarian cancer. An autopsy study," Cancer. 64(7):1508-13 (1989).
Rudikoff et al., "Single amino acid substitution altering antigen-binding specificity," Proc Natl Acad Sci USA. 79:1979-83 (1982).

Sabeh et al. "Tumor cell traffic through the extracellular matrix is controlled by the membrane-anchored collagenase MT1-MMP," J Cell Biol. 167(4):769-81 (2004).
Sahm et al. "Receptor binding affinities and biological activities of linear and cyclic melanocortins in B16 murine melanoma cells expressing the native MC1 receptor," J Pharm Pharmacol. 48(2):197-200 (1996).
Scott et al. "Searching for peptide ligands with an epitope library," Science. 249(4967):386-90 (1990).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Spatola et al., "Structure-activity relationships of enkephalins containing serially replaced thiomethylene amide bond surrogates," Life Sci. 38(14):1243-9 (1986).
Svenson et al., "Dendrimers in biomedical applications—reflections on the field," Adv Drug Deliv Rev. 57(15):2106-2129 (2005).
UniProt Consortium, "P08183 (MDR1_HUMAN)," <http://www.uniprot.org/uniprot/P08183>, retrieved on Sep. 18, 2013 (16 pages).
van de Waterbeemd et al., "Lipophilicity of amino acids," Amino Acids. 7(2):129-45 (1994).
Vincent, "Neurotensin receptors: binding properties, transduction pathways, and structure," Cell Mol Neurobiol. 15(5):501-512 (1995).
Wang et al., "Polyamidoamine dendrimers with a modified Pentaerythritol core having high efficiency and low cytotoxicity as gene carriers," Biomacromolecules. 10(3):617-622 (2009).
Wang et al., "Synthesis and antinociceptive effects of endomorphin-1 analogs with C-terminal linked by oligoarginine," Peptides. 32(2):293-9 (2011).
Williamson et al., "Expression and purification of recombinant neurotensin in *Escherichia coli*," Protein Expr Purif. 19(2):271-5 (2000).
Yano et al., "Simultaneous activation of two different receptor systems by enkephalin/neurotensin conjugates having spacer chains of various lengths," Eur J Pharm Sci. 7:41-48 (1998).
Zhai et al. "Expression of membrane type 1 matrix metalloproteinase is associated with cervical carcinoma progression and invasion," Cancer Res. 65(15):6543-6550 (2005).
Zhang et al. "In vitro gene delivery using polyamidoamine dendrimers with a trimesyl core," Biomacromolecules. 6(1):341-350 (2005).
EPO Communication for European Patent Application No. 08757166.7, dated Oct. 28, 2011 (4 pages).
EPO Communication for European Patent Application No. 08757166.7, dated Jun. 14, 2012 (3 pages).
EPO Communication for European Patent Application No. 08757166.7, dated Nov. 23, 2012 (3 pages).
Examination Report for Australian Application No. 2008255556, dated Nov. 15, 2012 (4 pages).
Examination Report for Australian Application No. 2008255556, dated Dec. 6, 2013 (4 pages).
First Office Action for Chinese Patent Application No. 200880100847.X, mailed Apr. 19, 2012 (13 pages).
Second Office Action for Chinese Patent Application No. 200880100847.X, mailed Apr. 8, 2013 (7 pages).
Third Office Action for Chinese Patent Application No. 200880100847.X, mailed Nov. 4, 2013 (9 pages).
Notice of Reasons for Rejection for Japanese Patent Application No. 2010-509648, mailed Jun. 11, 2013 (7 pages).
Second Office Action for Chinese Patent Application No. 200980156242.7, mailed Jan. 27, 2014 (13 pages).
Demeule et al., "Conjugation of a brain-penetrant peptide with neurotensin provides antinociceptive properties," J Clin Invest. 124(3):1199-213 (2014).
Shao et al., "Angiopep-2 modified PE-PEG based polymeric micelles for amphotericin B delivery targeted to the brain," J Control Release. 147(1):118-26 (2010).
Xin et al., "The brain targeting mechanism of Angiopep-conjugated poly(ethylene glycol)-co-poly(epsilon-caprolactone) nanoparticles," Biomaterials. 33(5):1673-81 (2012).

* cited by examiner

| Peptide | Amino acid sequence | Charge |
| --- | --- | --- |
| Angiopep | TFFYGGCRGKRNNFKTEEY | +2 |
| # 67 | TFFYGGCRGKRNNFKTEEY-amide | +2 |
| # 76 | TFFYGGCRGKRNNFKTKEY-amide | +3 |
| # 91 | RFKYGGCLGNKNNYLRLKY-amide | +5 |
| # 5 | TFFYGGCRAKRNNFKRAKY-amide | +6 |

Charge + : lysine (K), arginine (R)
Charge − : glutamic acid (E), aspartic acid (D)

Fig. 1

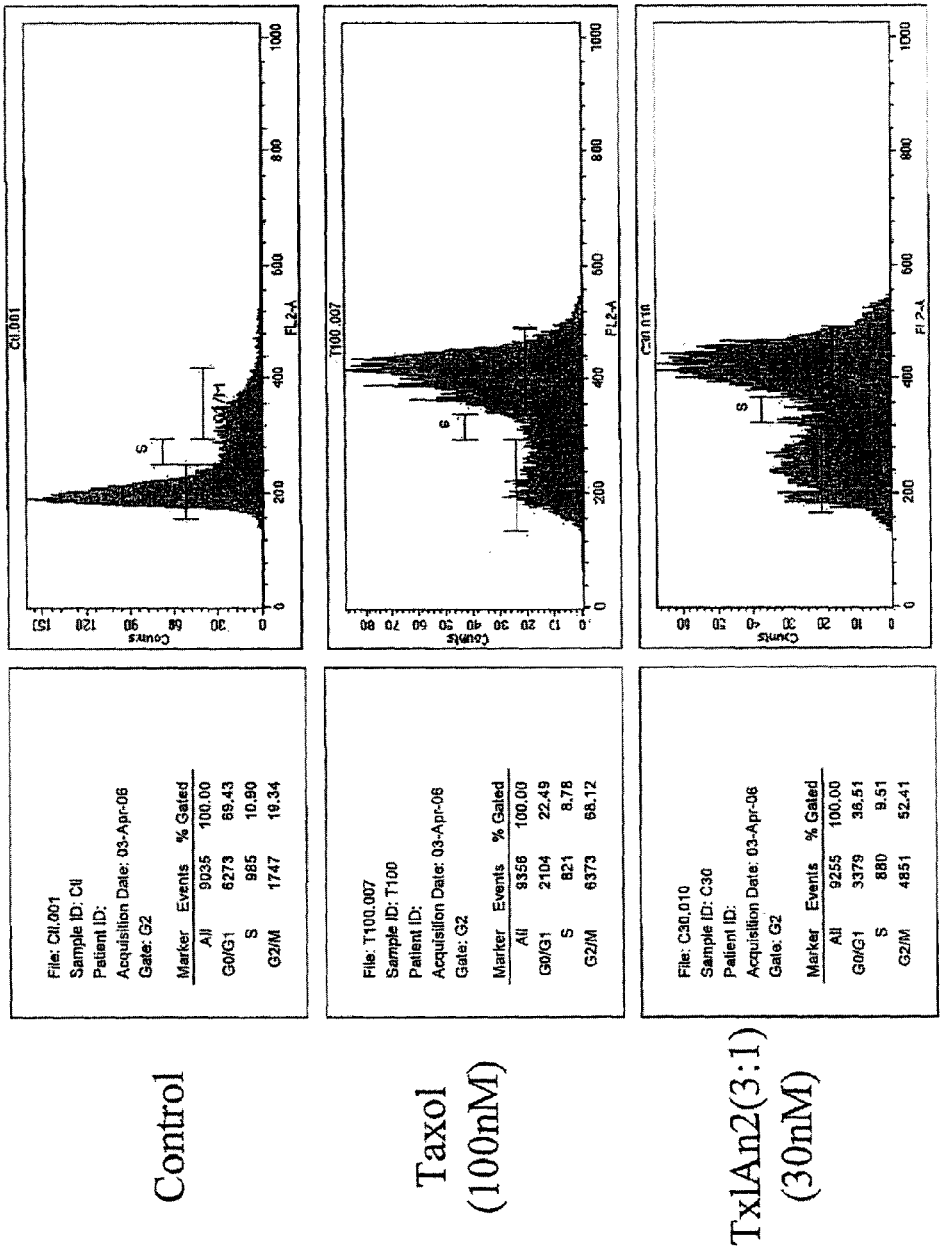

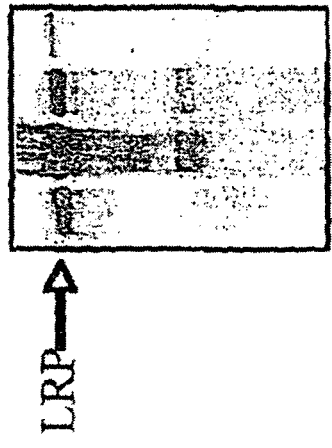
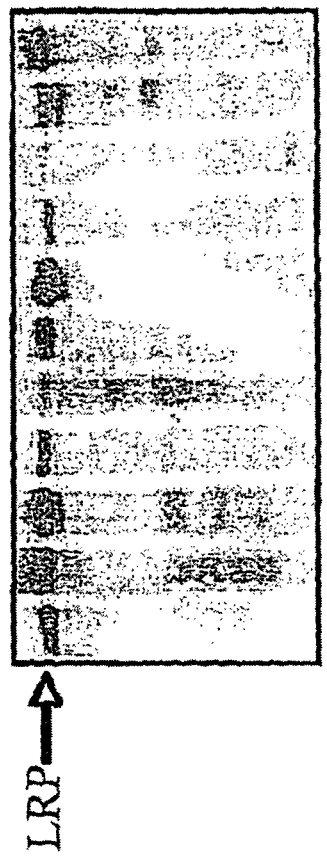
Fig. 22A
Fig. 22B

[TxlAn2 (3:1)]

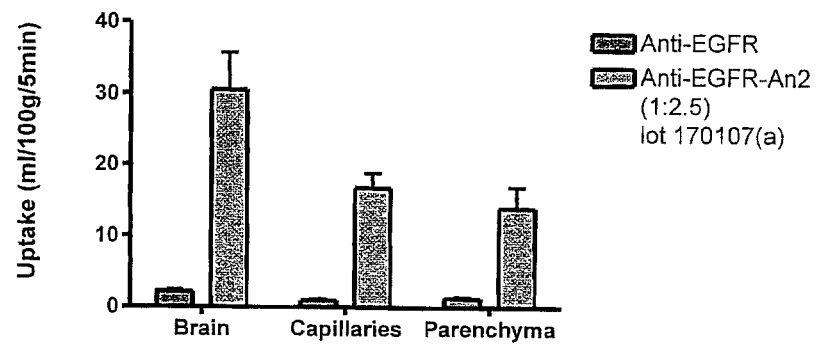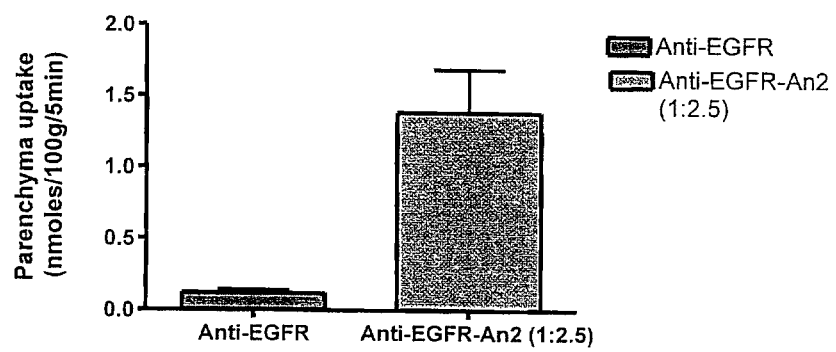
Fig.31

APROTININ-LIKE POLYPEPTIDES FOR DELIVERING AGENTS CONJUGATED THERETO TO TISSUES

CROSS-REFERENCE TO RELATED APPLICATIONS

This application is the national stage of International Application No. PCT/CA2008/001030, filed May 29, 2008, which claims the benefit of U.S. Provisional Application No. 61/008,880, filed Dec. 20, 2007, and, further, is a continuation-in-part of U.S. Application Nos. 11/807,917, filed May 30, 2007, and 11/807,597, filed May 29, 2007.

INCORPORATED BY REFERENCE OF A SEQUENCE LISTING FILED ELECTRONICALLY

Kindly incorporate the .txt file Sequence Listing, submitted Aug. 2, 2010, having the name 50546 004006 Sequence Listing ST25.txt, file size 36.0 kB, created Jul. 30,2010.

BACKGROUND OF THE INVENTION

The invention relates to improvements in the field of drug delivery. More particularly, the invention relates to polypeptides, conjugates and pharmaceutical compositions including the polypeptides of the invention and their use for transporting agents (e.g., therapeutic agents) across into particular cell types such as liver, lung, or kidney.

Diseases of the liver, including hepatitis (e.g., viral hepatitis) and cancers of the liver (e.g., hepatocarcinoma), and lung diseases, such as lung cancer (e.g., small cell and non-small cell lung cancer) are serious health problems. Many therapeutic agents for such diseases have undesirable side effects (e.g., chemotherapeutic agents) or, for reasons such as in vivo stability, transport, or other pharmacokinetic properties, are difficult to provide at a sufficiently high concentration in the target tissue or for a sufficiently long duration to allow maximal therapeutic effect in the target tissue.

Accordingly, there is a need for methods and compositions that increase concentrations of therapeutic and diagnostic agents in target organs or tissues.

SUMMARY OF THE INVENTION

We have discovered that the polypeptides described herein (e.g., Angiopep-7; SEQ ID NO:112) are efficiently transported into particular cell types (e.g., liver, lung, spleen, kidney, and muscle), but are not efficiently transported across the blood-brain barrier (BBB). When conjugated to an agent, the polypeptides act as vectors and are capable of increasing the concentration of the conjugated agent in the cell. We have also identified Angiopep-3, Angiopep-4a, Angiopep-4b, Angiopep-5, and Angiopep-6 (SEQ ID NOS:107-111) as vectors which can be efficiently transported across the BBB and may additionally be transported into particular cell types. The invention therefore features polypeptides, conjugates including the polypeptides as vectors, and methods for diagnosing and treating diseases (e.g., cancer) with such polypeptides and conjugates.

Accordingly, in a first aspect the invention features a polypeptide including an amino acid sequence having the formula:

X1-X2-X3-X4-X5-X6-X7-X8-X9-X10-X11-X12-X13-X14-X15-X16-X17-X18-X19 where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-112 (e.g., Angiopep-1, Angiopep-2, Angiopep-3, Angiopep-4a, Angiopep-4b, Angiopep-5, Angiopep-6, and Angiopep-7). In some embodiments at least one (e.g., 2, 3, 4, or 5) of the amino acids X1-X19 are Arg (e.g., any one, two, or three of X1, X10, and X15).

In other embodiments, the invention features a polypeptide including an amino acid sequence having substantial identity to any one of SEQ ID NOS:1-105 and 107-112 (e.g., Angiopep-3, Angiopep-4a, Angiopep-4b, Angiopep-5, Angiopep-6 and Angiopep-7). In certain embodiments, the polypeptide may include or may be Angiopep-3, Angiopep-4a, Angiopep-4b, Angiopep-5, Angiopep-6, or Angiopep-7 (SEQ ID NOS: 107-112), may include a sequence substantially identical to the Angiopep-7 sequence or a fragment thereof (e.g., a functional fragment). The polypeptide may have an amino acid sequence of 10 to 50 amino acids, e.g., 10 to 30 amino acids, in length. The invention also features functional derivatives (e.g., chemical derivatives or variants) of these polypeptides.

Exemplary polypeptides of the invention have a lysine or arginine at position 10 (with respect to amino acid sequence of SEQ ID NO:1) or a lysine or arginine at position 15 (with respect to amino acid sequence of SEQ ID NO:1), or a lysine or arginine at both position 10 and at position 15. The polypeptides of the invention may also have a serine or cysteine at position 7 (with respect to amino acid sequence of SEQ ID NO:1). Where multimerization of polypeptides is desired, the polypeptide may include a cysteine (e.g., at position 7).

In certain embodiments, the polypeptides of the invention (e.g., any polypeptide described herein) are modified (e.g., as described herein). The polypeptide may be amidated, acetylated, or both. For example, a polypeptide including Angiopep-6 or Angiopep-7 may be amidated, or SEQ ID NO:67 may be amidated (polypeptide No. 67). In another example, the amino acid of any one of SEQ ID NOS:107-112, or any other polypeptide of the invention, is amidated or acetylated. Such modifications to polypeptides of the invention may be at the amino or carboxy terminus of said polypeptide. The invention also features peptidomimetics (e.g., those described herein) of any of the polypeptides described herein. The polypeptides of the invention may be in a multimeric form. For example, polypeptides may be in a dimeric form (e.g., formed by disulfide bonding through cysteine residues).

The polypeptides of the invention may be efficiently transported into particular cells (e.g., liver, kidney, lung, muscle, or spleen cells) or may efficiently cross the BBB (e.g., Angiopep-3, Angiopep-4a, Angiopep-4b, Angiopep-5, and Angiopep-6). In some embodiments, the polypeptide are efficiently transported into particular cells (e.g., liver, kidney, lung, muscle, or spleen cells) and are not efficiently transported across the BBB (e.g., Angiopep-7). The polypeptide may be efficiently transported into at least one (e.g., at least two, three, four, or five) of a cell or tissue selected from the group consisting of liver, kidney, lung, muscle, or spleen.

For any of the polypeptides and conjugates described herein, the amino acid sequence may specifically exclude a polypeptide including or consisting of any of SEQ ID NOS:

1-105 and 107-112 (e.g., any of SEQ ID NOS:1-96, Angiopep-1, Angiopep-2, Angiopep-3, Angiopep-4a, Angiopep-4b, Angiopep-5, Angiopep-6, and Angiopep-7). In some embodiments, the polypeptides and conjugates of the invention exclude the polypeptides of SEQ ID NOS:102, 103, 104 and 105. In other embodiments, the polypeptides and conjugates of the invention include these polypeptides.

In certain embodiments, a polypeptide of the invention may have an amino acid sequence described herein with at least one amino acid substitution (e.g., 2, 3, 4, 5, 6, 7, 8, 9, 10, 11, or 12 substitutions). In certain embodiments, the polypeptide may have an arginine at one, two, or three of the positions corresponding to positions 1, 10, and 15 of the amino acid sequence of any of SEQ ID NO:1, Angiopep-1, Angiopep-2, Angiopep-3, Angiopep-4a, Angiopep-4b, Angiopep-5, Angiopep-6, and Angiopep-7. For example, the polypeptide may contain 1 to 12 amino acid substitutions (e.g., SEQ ID NO:91). For example, the amino acid sequence may contain 1 to 10 (e.g., 9, 8, 7, 6, 5, 4, 3, 2) amino acid substitutions or 1 to 5 amino acid substitutions. In accordance with the invention, the amino acid substitution may be a conservative or non-conservative amino acid substitution.

The polypeptides of the invention may be synthesized chemically (e.g., solid phase synthesis) or may be produced by recombinant DNA technology, as known in the art. Any of the polypeptides, compositions, or conjugates described herein may be in an isolated form or in a substantially purified form.

In another aspect, the invention features a polynucleotide sequence encoding a polypeptide of the invention (e.g., any polypeptide described herein, such as Angiopep-3, Angiopep-4a, Angiopep-4b, Angiopep-5, Angiopep-6, and Angiopep-7). More particularly, nucleotide sequences (deoxyribonucleotides, ribonucleotides, or derivatives thereof) encoding a polypeptide selected from the group consisting of any one of SEQ ID NOS:1-97 and SEQ ID NO:107-112 are encompassed by the invention. A desired nucleotide sequence may be synthesized chemically by methods known in the art.

In another aspect, the invention features a conjugate including a vector selected from the group consisting of any one of the polypeptides, analogs, or derivatives thereof described herein (e.g., Angiopep-3, Angiopep-4a, Angiopep-4b, Angiopep-5, Angiopep-6, and Angiopep-7), and an agent, where the agent is conjugated to the vector.

The agent may be selected from the group consisting of a therapeutic agent (e.g., a small molecule drug, such as an anticancer agent, antibiotic, or any described herein), a detectable label, a polypeptide (e.g., an enzyme), and a protein complex. In some embodiments, the agent has a maximum molecular weight of about 160,000 Daltons. The agent may be a molecule active in the central nervous system. The agent may be any agent useful for treating or detecting a neurological, liver, lung, kidney, or spleen disease. The detectable label may be, for example, a radioimaging agent (e.g., an isotope), a fluorescent label (e.g., rhodamine, FITC, cy5.5, alexa), a reporter molecule (e.g., biotin). Other examples of detectable labels include green fluorescent protein, histag protein, and β-galactosidase. The conjugate may he a fusion protein consisting essentially of the vector and a protein. Examples of protein-based compounds which can be conjugated to a vector of the invention include an antibody (e.g., including heavy and/or light chains), an antibody fragment (e.g., an antibody binding fragment such as Fv fragment, F(ab)2, F(ab)2', and Fab). An antibody or fragment thereof that may be conjugated to the vector includes a monoclonal or polyclonal antibody and, further, may be of any origin (e.g., human, chimeric, and humanized antibodies).

Other protein or protein-based compounds include cellular toxins (e.g., monomethyl auristatin E (MMAE), bacteria endotoxins and exotoxins, diphtheria toxins, botulinum toxin, tetanus toxins, perussis toxins, staphylococcus enterotoxins, toxin shock syndrome toxin TSST-1, adenylate cyclase toxin, shiga toxin, and cholera enterotoxin) and anti-angiogenic compounds (endostatin, catechins, nutriceuticals, chemokine IP-10, inhibitors of matrix metalloproteinase (MMPIs), anastellin, vironectin, antithrombin, tyrosine kinase inhibitors, VEGF inhibitors, antibodies against receptor, herceptin, avastin, and panitumumab).

Leptin exendin-4, GLP-1, PYY, or PYY(3-36) may be used, e.g., for treatment of obesity. Other polypeptides that may be included in a conjugate of the invention are adrenocortiocotropic hormones (ACTH, corticotropin), growth hormone peptides (e.g., human placental lactogen (hPL), growth hormones, and prolactin (Prl)), melanocyte stimulating hormones (MSH), oxytocin, vasopressin (ADH), corticotropin releasing factor (CRF), gonadotropin releasing hormone associated peptides (GAP), growth hormone releasing factor (GRF), lutenizing hormone release hormones (LH-RH), orexins, prolactin releasing peptides, somatostatin, thyrotropin releasing hormone (THR), calcitonin (CT), caltitonin precursor peptide, calcitonins gene related peptide (CGRP), parathyroid hormones (PTH), parathyroid hormone related proteins (PTHrP), amylin, glucagon, insulin and insulin-like peptides, neuropeptide Y, pancreatic polypeptide (PP), peptide YY, somatostatin, cholecystokinin (CCK), gastrin releasing peptide (GRP), gastrin, gastrin inhibitory peptide, motilin, secretin, vasoactive intestinal peptide (VIP), natriuretic peptides (e.g., atrial natriuretic peptide (ANP), B-type natriuretic peptide (BNP), brain natriuretic peptide, and C-type natriuretic peptide (CNP)), tachykinins (e.g., neurokinin A, neurokinin B, and substance P), substance P, angiotensins (e.g., angiotensin I and angiotensin II), renin, endothelins (e.g., endothelin-1, endothelin-2, endothelin-3, sarafotoxin (a snake venom) and scorpion toxin), sarafotoxin peptides, opioid peptides (e.g., casomorphin peptides, demorphins, endorphins, enkephalins, deltorphins, dynorphins), thymic peptides (e.g., thymopoietin, thymulin, thymopentin, thymosin, thymic humoral factor (THF)), adrenomedullin peptides (AM), allatostatin peptides, amyloid beta-protein fragments (Aβ fragments), antimicrobial peptides (e.g., defensin, cecropin, buforin, and magainin), antioxidant peptides (e.g., natural killer-enhancing factor B (NKEF-B), bombesin, bone Gla protein peptides (e.g., osteocalcin (bone Gla-protein, or BGP), CART peptides, cell adhesion peptides, cortistatin peptides, fibronectin fragments and fibrin related peptides, FMRF peptides, galanin, guanylin and uroguanylin, and inhibin peptides.

Small molecule drugs include an anticancer agents (e.g., any such agent described herein). Examples of anticancer agents include paclitaxel (Taxol), vinblastine, vincristine, etoposide, doxorubicin, cyclophosphamide, taxotere, melphalan, chlorambucil, and any anticancer agent described herein, or any combination thereof. An anticancer agent may have chemical moiety allowing conjugation to the vector of the invention.

In certain embodiments, the conjugate of the invention may include the formula $V_x$-$L_y$-$A_z$ or a pharmaceutically acceptable salt thereof, wherein V is a polypeptide or derivative thereof described herein (e.g., Angiopep-3, Angiopep-4a, Angiopep-4b, Angiopep-5, Angiopep-6, Angiopep-7, or any of the analogs, derivatives, or fragments described herein). V may be efficiently transported into a particular cell type (e.g., a liver, lung, kidney, spleen, or muscle cell) or may be efficiently transported across the BBB (e.g., after attachment to $L_y$-$A_z$). In certain embodiments, the vector or conjugate is not efficiently transported across the BBB, but is efficiently transported into a particular cell type (e.g., Angiopep-7). L is a linker or a bond (e.g., chemical or covalent bond). A is an agent such as those selected from the group consisting of a therapeutic agent (e.g., a small molecule drug), a detectable label, a protein, or protein-based compound (e.g., antibody, an antibody fragment), an antibiotic, an anti-cancer agent, an anti-angiogenic compound and a polypeptide or any molecule active at the level of the central nervous system.

X, Y, and Z may each independently be any number greater than 0 (e.g., 1, 2, 3, 4, 5, 6, 7, 8, 9, or 10) or may represent a range of values between 1 (e.g., 2, 3, 4, 5, 6, 7, 8, 9) and 10 (e.g., 9, 8, 7, 6, 5, 4, 3, 2). Accordingly, the formula $V_x$-$L_y$-$A_z$ is not restricted to a specific order or specific ratio; for example, the conjugate may include 1 to 5 vectors (1, 2, 3, 4, or 5) coupled to the agent. In other embodiments, more than one agent may be conjugated to the vector. The agent or conjugate may be active when the agent is conjugated to the vector. In some embodiments, the compound can be released from the vector, e.g., following transport across the BBB or into a particular cell type. The compound may become active following its release (e.g., as a prodrug). In some embodiments, the agent remains conjugated to the vector following transport. Here, the conjugate may exhibit reduced efflux transport (e.g., by P-glycoprotein) as compared to the unconjugated agent. In this case, it may be desirable that the agent and vector remain bound. The conjugate may be provided in a pharmaceutically acceptable composition.

The agent, when conjugated to a vector, may exhibit modified (e.g., improved) bioavailability, improved potency (e.g., anticancer activity), altered tissue distribution of the agent, decreased toxicity, or altered pharmacokinetics as compared to the agent when unconjugated to the vector. A vector (e.g., Angiopep-3, Angiopep-4a, Angiopep-4b, Angiopep-5, and Angiopep-6) may promote accumulation of the agent in the brain of an individual (e.g., a brain containing a tumor cell such as a glioblastoma, lung, breast, colon, liver, pancreas, or spleen, tumor cell) or in a particular cell or tissue (e.g., liver, lung, kidney, spleen, and muscle). A vector such as Angiopep-7 may be able to promote accumulation in cell types such as liver, lung, kidney, spleen or muscle, but not promote accumulation in the brain. More particularly, the vector can increase the accumulation or potency of an agent which is a P-gp substrate or therapeutic agents which are expelled by P-gp or a P-gp-related protein (e.g., a P-gp human or mammalian allelic variant, e.g., a mdrla or mdrlb isoforms from a rodent), when provided (e.g., administered) to a subject. The cell may express or may be able to express P-gp or P-gp related protein. The cell into which the conjugate is transported may express a vector receptor or transporter, for example, a low-density lipoprotein related receptor (LRP) (e.g., a cell which co-expresses P-gp or a P-gp related protein). The cell may be, for example a normal cell, a tumor cell, or a metastatic cell (e.g., a multidrug resistance cancer cell). The cell or tumor may be a metastasis (e.g., of any of the cancers described herein).

A vector or conjugate may be efficiently transported into a particular cell type (e.g., liver, lung, kidney, spleen, or muscle cells) and may be efficiently transported across the BBB; such conjugates include Angiopep-3, Angiopep-4a, Angiopep-4b, Angiopep-5, and Angiopep-6. In certain embodiments, the transporting activity of the vector, per se, does not affect the integrity of the cell into which it is being delivered or does not affect BBB integrity. In other embodiments, the vector or conjugate, such as Angiopep-7, is efficiently transported into a particular cell type, but is not efficiently transported across the BBB. Any vector or conjugate described here may be transported by receptor-mediated endocytosis or transcytosis or by adsorptive-mediated endocytosis or transcytosis.

Any vector or conjugate described herein may be present in an pharmaceutically acceptable carrier (e.g., may be in the form a medicament). The invention therefore features a pharmaceutical composition including (a) a conjugate (e.g., any conjugate described herein); (b) a pharmaceutically acceptable carrier (e.g., any described herein). The conjugate may further include (c) a solubilizer. The solubilizer may be, for example, a polyoxyethylene ester of fatty acid (e.g., Solutol® HS-15). The pharmaceutical composition may be used for modifying the pharmacokinetics of a compound, for reducing the growth of a tumor cell, or for the detection of a tumor cell.

In another aspect, the invention features the use of a vector or a conjugate of the invention for the diagnosis or treatment of (e.g., for the manufacture of a medicament or use in treating) a liver disease, lung disease, kidney disease, spleen disease, or muscle disease. In certain embodiments a neurological disease or a central nervous system disease (e.g., any disease described herein) may be treated using a conjugate of the invention that is efficiently transported across the BBB. For example, the vector or conjugate may be used for the in vivo detection of any of these diseases. The treatment or diagnosis may be performed in a mammal (e.g., a human or non-human mammal) in need thereof, such as a mammal having or at risk (e.g., increased risk) of having the disease (e.g., a cancer). The administration may be performed using any means known in the art, for example, intraarterially, intranasally, intraperitoneally, intravenously, intramuscularly, subcutaneously, transdermally, or per os. The administration may be in a therapeutically effective amount.

By conjugating an agent to a vector described herein, the toxicity of the agent may be reduced, thus allowing the agent to be provided to the subject at a dose higher than the recommended dose for the agent alone. Accordingly, the invention features a method of treating a subject having a disease or condition (e.g., any disease or condition described herein such as cancer) including providing a conjugate of the invention to the subject, wherein said conjugate includes an agent, at a dose higher (e.g., at least 5%, 10%, 25%, 50%, 75%, 100%, 250%, 500%, 1,000%, 5,000%, or 10,000% higher) than the therapeutic dose of the agent alone.

Because a vector described herein may be capable of targeting an agent to a particular cell type (e.g., those described herein), the agent when conjugated to a vector can, in certain embodiments, have a higher efficacy when administered to the subject. Accordingly, the invention also features a method of treating a subject having a disease or condition (e.g., any disease or condition described herein such as cancer) by administering to the subject a conjugate or a composition including a conjugate of the invention, wherein the conjugate includes agent, in a dose lower (e.g., 5%, 10%, 15%, 20%, 30%, 50%, 70%, 80%, 90%, 95%, 98%, 99%, 99.9% lower) than the therapeutic dose of the agent alone.

The treatments methods of the invention may further comprise a step of assessing whether the tumor of the individual includes a multiple drug resistant tumor cell (e.g., a cell expressing P-gp (MDR1) or determining whether the tumor may have or has a multiple resistance drug phenotype). The treatment methods may include a step of providing chemotherapy, radiotherapy, or both. Alternatively, the subject being treated may have received (or will receive) such therapies (e.g., within 1 year, 6 mo, 3 mo, 2 mo, 1 mo, 2 weeks, 1 week, 3 days, 2 days, or 1 day). The individual may have had surgery. The individual may have a brain tumor (e.g., a primary brain tumor) or a tumor at a site other than the brain (e.g., does not have a brain tumor). An individual in need may have present or is at risk of developing a resistance to at least one drug (e.g., a multiple drug resistance (MDR) phenotype). The tumor may be a lung tumor, an extracranial metastasis of a brain tumor of (e.g., from a glioblastoma), a brain tumor of metastatic origin (e.g., from a lung tumor, a breast tumor, a melanoma, a colorectal cancer, or a urinary organ tumor). The tumor may include a cell expressing P-gp, LRP, or both, or a cell capable of expressing P-gp, LRP, or both. P-gp and LRP may be localized to a cell surface.

In other aspect, the invention also features a method of increasing the concentration of an agent in a cell or transport of an agent to a cell, where the cell expresses a member of the LRP receptor family. The method includes contacting the cell with a conjugate comprising the agent conjugated to a vector (e.g., any polypeptide described herein), thereby increasing concentration of the agent in the cell, or transporting the agent to the cell. The invention also features a method of increasing the concentration of agent in a cell, where the cell expresses P-glycoprotein. The method includes contact the cell with a conjugate including the agent conjugated to a vector (e.g., any polypeptide described herein), thereby increasing the concentration of the agent in the cell, as compared to the unconjugated agent.

In accordance with the any of the aspects of the invention, neurological diseases include a brain tumor, a brain metastasis, schizophrenia, epilepsy, Alzheimer's disease, Parkinson's disease, Huntington's disease, stroke, and BBB related malfunctions (e.g., obesity). The liver disease may be a cancer such as hepatocarcinoma. Other liver diseases include those described herein. The lung disease may be a lung cancer (e.g., those described herein).

The conjugates can include vectors in the form of multimers such as dimers. Multimeric forms of the vectors can, in some embodiments, increase the transport or accumulation of the agent. Vectors may also be in a ratio of at least 1:1 (agent: vector), 1:2, 1:3, 1:4, 1:5, 1:6, or 1:10. As indicated herein, the higher ratios of vector to agent can lead to increased transport. As such, the number of vector per agent is not intended to be limited.

Also in accordance with the invention, the pharmaceutical composition may be used, for example, for the delivery of an agent to the CNS of an individual.

A pharmaceutically acceptable salt of a vector (polypeptide) or of a conjugate is encompassed by the invention and may include pharmaceutically acceptable acid addition salts of the agent.

The vector or conjugate of the invention may be used in combination with or separately from conventional methods of treatment or therapy. Combination therapy with other agents may include sequential or concurrent administration to an individual. Pharmaceutical compositions of the invention may include a combination of a vector-agent conjugate of the invention in association with a pharmaceutically acceptable excipient, as described herein, and another therapeutic or prophylactic agent known in the art.

By "vector" is meant a compound or molecule such as a polypeptide that is able to be transported into a particular cell type (e.g., liver, lungs, kidney, spleen, or muscle) or across the BBB. The vector may be attached to (covalently or not) or conjugated to an agent and thereby may be able to transport the agent into a particular cell type or across the BBB. In certain embodiments, the vector may bind to receptors present on cancer cells or brain endothelial cells and thereby be transported into the cancer cell or across the BBB by transcytosis. The vector may be a molecule for which high levels of transendothelial transport may be obtained, without affecting the cell or BBB integrity. The vector may be a polypeptide or a peptidomimetic and may be naturally occurring or produced by chemical synthesis or recombinant genetic technology.

By "conjugate" is meant a vector linked to an agent. The conjugation may be chemical in nature, such as via a linker, or genetic in nature for example by recombinant genetic technology, such as in a fusion protein with for example a reporter molecule (e.g., green fluorescent protein, β-galactosidase, Histag, etc.).

By a vector which is "efficiently transported across the BBB" is meant a vector that is able to cross the BBB at least as efficiently as Angiopep-6 (i.e., greater than 38.5% that of Angiopep-1 (250 nM) in the in situ brain perfusion assay described herein). Accordingly, a vector or conjugate which is "not efficiently transported across the BBB" is transported to the brain at lower levels (e.g., transported less efficiently than Angiopep-6).

By a vector or conjugate which is "efficiently transported to a particular cell type" is meant a vector or conjugate that is able to accumulate (e.g., either due to increased transport into the cell, decreased efflux from the cell, or a combination thereof) in that cell type at least 10% (e.g., 25%, 50%, 100%, 200%, 500%, 1,000%, 5,000%, or 10,000%) greater extent than either a control substance, or, in the case of a conjugate, as compared to the unconjugated agent.

By "substantially pure" or "isolated" is meant a compound (e.g., a polypeptide or conjugate) that has been separated from other chemical components. Typically, the compound is substantially pure when it is at least 30%, by weight, free from other components. In certain embodiments, the preparation is at least 50%, 60%, 75%, 85%, 90%, 95%, 96%, 97%, 98%, or 99% by weight, free from other components. A purified polypeptide may be obtained, for example, by expression of a recombinant polynucleotide encoding such a polypeptide or by chemically synthesizing the polypeptide. Purity can be measured by any appropriate method, for example, column chromatography, polyacrylamide gel electrophoresis, or by HPLC analysis.

By "analogue" is meant a polypeptide originating from an original sequence or from a portion of an original sequence and which may include one or more modification; for example, one or more modification in the amino acid sequence (e.g., an amino acid addition, deletion, insertion, or substitution), one or more modification in the backbone or side-chain of one or more amino acid, or an addition of a group or another molecule to one or more amino acids (side-chains or backbone). An analog may have one or more amino acid insertions, at either or at both of the ends of the polypeptide or inside the amino acid sequence of the polypeptide. An analogue may have sequence similarity and/or sequence identity (e.g., may be substantially identical) with that of an original sequence or a portion of an original sequence. Analogs may include a modification of its structure, e.g., as described herein. The degree of similarity between two sequences is base upon the percentage of identities (identical amino acids) and of conservative substitution. An analogue may have at least 35%, 50f%, 60%, 70%, 80%, 90%, or 95% (e.g., 96%, 97%, 98%, 99%, and 100%) sequence similarity to an original sequence with a combination of one or more modifications in a backbone or side-chain of an amino acid, or an addition of a group or another molecule. Exemplary amino acids which are intended to be similar (a conservative amino acid) to others are known in the art and includes, for example, those listed in Table 3.

By "substantially identical" is meant a polypeptide or nucleic acid exhibiting at least 35%, 40%, 50%, 55%, 60%, 65%, 70%, 75%, 85%, 90%, 95%, or even 99% identity to a reference amino acid or nucleic acid sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For nucleic acids, the length of comparison sequences will generally be at least 60 nucleotides, preferably at least 90 nucleotides, and more preferably at least 120 nucleotides, or full length. It is to be understood herein that gaps may be found between the amino acids of an analogs which are identical or similar to amino acids of the original polypeptide. The gaps may include no amino acids, one or more amino acids which are not identical or similar to the original polypeptide. Biologically active analogs of the vectors (polypeptides) of the invention are encompassed herewith. Percent identity may be determined, for example, with n algorithm GAP, BESTFIT, or FASTA in the Wisconsin Genetics Software Package Release 7.0, using default gap weights.

By "functional derivative" is meant a "chemical derivative," "fragment," or "variant" biologically active sequence or portion of a vector or agent or conjugate and a salt thereof of the invention. A vector functional derivative may be able to be attached to or conjugated to an agent and enter a particular cell type, thereby transporting the agent into that cell.

By "chemical derivative" is meant a vector, an agent, or a conjugate of the invention, which contains additional chemical moieties not a part of the vector, agent or vector-agent conjugate, including covalent modifications. A chemical derivative may be prepared by direct chemical synthesis using methods known in the art. Such modifications may be introduced into a protein or peptide vector, agent, or vector-agent conjugate by reacting targeted amino acid residues with an organic derivatizing agent capable of reacting with selected side chains or terminal residues. A vector chemical derivative may be able to cross the BBB or to enter or accumulate in a particular cell type (e.g., those described herein). In a preferred embodiment, very high levels of transendothelial transport across the BBB are obtained without effecting BBB integrity.

By "fragment" is meant a polypeptide originating from a portion of an original or parent sequence or from an analogue of said parent sequence. Fragments encompass polypeptides having truncations of one or more amino acids, wherein the truncation may originate from the amino terminus (N-terminus), carboxy terminus (C-terminus), or from the interior of the protein. A fragment may include the same sequence as the corresponding portion of the original sequence. Functional fragments of the vector (polypeptide) described herein are encompassed by the invention. Fragments may be at least 5 (e.g., at least 5, 6, 7, 8, 9, 10, 11, 12, 13, 14, 15, 16, 17, 18, 19, 20, 21, 22, 23, 25, 28, 30, 35, 40, 45, 50, 60, 75, 100, or 150) amino acids. Fragments of the invention may include, for example, a polypeptide of 7, 8, 9 or 10 amino acids to 18 amino acids. Fragments may contain any of the modifications described herein (e.g., acetylation, amidation, amino acid substitutions)

A "non-naturally occurring amino acid" is an amino acid which is not naturally produced or found in a mammal.

By "agent" is meant, any compound, for example, an antibody, or a therapeutic agent, a marker, a tracer, or an imaging compound.

By "therapeutic agent" is meant an agent having a biological activity. In some cases, the therapeutic agent is used to treat the symptoms of a disease, a physical or mental condition, an injury, or an infection and includes anti-cancer agents, antibiotics, anti-angiogenic agents, and molecules active at the level of the central nervous system.

By "small molecule drug" is meant a drug having a molecular weight of 1,000 g/mol or less (e.g., less than 800, 600, 500, 400, or 200 g/mol).

By "subject" is meant a human or non-human animal (e.g., a mammal).

By "treatment," "treating," and the like are meant obtaining a desired pharmacological or physiological effect, e.g., inhibition of cancer cell growth, death of a cancer cell, amelioration of a disease or condition (e.g., any disease or condition described herein), or amelioration of at least one symptom associated with a disease or condition. The effect may be prophylactic, e.g., completely or partially preventing a disease or symptom thereof or may be therapeutic in terms of a partial or complete cure for a disease and/or adverse effect attributable to the disease. Treatment includes: (a) preventing a disease or condition (e.g., preventing cancer) from occurring in an individual (e.g., one who is predisposed to the disease but has not been diagnosed as having it); (b) inhibiting a disease (e.g., arresting its development); or (c) relieving a disease (e.g., reducing symptoms associated with a disease). Treatment includes any administration of a therapeutic agent to an individual to treat, cure, alleviate, improve, diminish or inhibit a condition in the individual, including, without limitation, administering a vector-agent conjugate to an individual.

By "cancer" is meant any cellular proliferation whose unique trait is the loss of normal controls which can result in unregulated growth, lack of differentiation, or ability to invade tissues and metastasize. Cancer can develop in any tissue or in any organ. Cancer is intended to include, without limitation, cancer of the brain, liver, lungs, kidney, or spleen. Additional cancers are described herein.

By "providing" is meant, in the context of a vector or conjugate of the invention, to bring the vector or conjugate into contact with a target cell or tissue either in vivo or in vitro. A vector or conjugate may be provided by administering the vector or conjugate to a subject.

By "administering" and "administration" is meant a mode of delivery including, without limitation, intra-arterially, intra-nasally, intraperitoneally, intravenously, intramuscularly, subcutaneously, transdermally, or per os. A daily dosage can be divided into one, two, or more doses in a suitable form to be administered at one, two or more times throughout a time period.

By "therapeutically effective" or "effective amount" is meant an amount of a therapeutic agent sufficient to improve, decrease, prevent, delay, suppress, or arrest any symptom of the disease or condition being treated. A therapeutically effective amount of an agent need not cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

By "condition" is meant any situation causing pain, discomfort, sickness, disease or disability (mental or physical) to or in an individual, including neurological disease, injury, infection, or chronic or acute pain. Neurological diseases include brain tumors, brain metastases, schizophrenia, epilepsy, Alzheimer's disease, Parkinson's disease, Huntington's disease, and stroke.

By "pharmaceutical composition" is meant a therapeutically effective amount of an agent together with a pharmaceutically acceptable diluent, preservative, solubilizer, emulsifier, or adjuvant, for example, any of those described herein.

By "therapeutic dose" is meant the dosage of a agent such as a drug (without the vector) acceptable for use clinically with respect to its toxicity or efficacy. By conjugation of an agent to a vector of the invention, it may be possible to administer the agent at a dosage either lower or higher dosage than the therapeutic dose.

If a "range" or "group of substances" is mentioned with respect to a particular characteristic (e.g., temperature, concentration, time and the like), the invention relates to and explicitly incorporates herein each and every specific member and combination of sub-ranges or sub-groups therein. Thus, for example, with respect to a length of from 9 to 18 amino acids, is to be understood as specifically incorporating herein each and every individual length, e.g., a length of 18, 17, 15, 10, 9, and any number therebetween. Therefore, unless specifically mentioned, every range mentioned herein is to be understood as being inclusive. For example, in the expression from 5 to 19 amino acids long is to be as including 5 and 19. This similarly applies with respect to other parameters such as sequences, length, concentrations, elements, and the like.

The sequences, regions, portions defined herein each include each and every individual sequence, region, and portion described thereby as well as each and every possible sub-sequence, sub-region, and sub-portion whether such sub-sequences, sub-regions, and sub-portions are defined as positively including particular possibilities, as excluding particular possibilities or a combination thereof. For example, an exclusionary definition for a region may read as follows: "provided that said polypeptide is no shorter than 4, 5, 6, 7, 8 or 9 amino acids. A further example of a negative limitation is the following; a sequence including SEQ ID NO:X with the exclusion of a polypeptide of SEQ ID NO:Y; etc. An additional example of a negative limitation is the following; provided that said polypeptide is not (does not include or consist of) SEQ ID NO:Z.

BRIEF DESCRIPTION OF THE DRAWINGS

FIG. 1 illustrates the structure of exemplary polypeptides of the invention (Angiopep is SEQ ID NO: 67, Peptide #67 comprises SEQ ID NO: 67, Peptide #76 comprises SEQ ID NO: 76, Peptide #91 comprises SEQ ID NO: 91, and Peptide #5 comprises SEQ ID NO: 5).

FIG. 20 is a set of graphs showing the effect of Taxol and TxlAn2 conjugate on NCI-H460 cell-cycle measured by FACS. Cells were exposed for 24 hrs with the vehicle (DMSO), Taxol (100 nM), or TxlAn2 conjugate (30 nM, equivalent to 100 nM of Taxol).

FIGS. 22A and 22B are photographs of western blots showing immunodetection of LRP in human brain tumor biopsies.

FIG. 31 illustrates the distribution volume in the brain parenchyma of free and Angiopep-2 conjugated EGFR antibody.

DETAILED DESCRIPTION OF THE INVENTION

Figure 2:
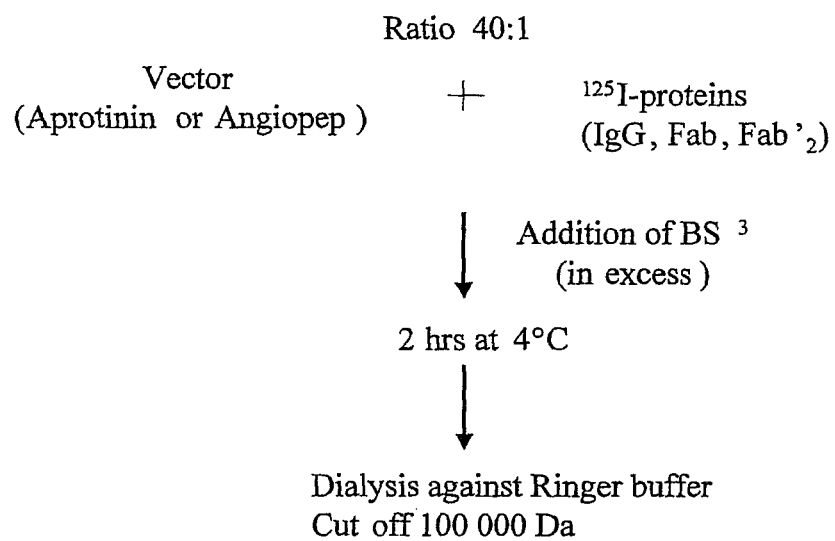
FIG. 2 illustrates the protocol used to conjugate aprotinin with IgG using cross-linker BS$^3$.

We have discovered that Angiopep-7 can be efficiently transported into particular cell types or organs such as liver, lungs, kidneys, spleen, and muscle, but is not efficiently transported across the blood-brain barrier (BBB), relative to polypeptides such as Angiopep-1 or Angiopep-2. On this basis we have identified Angiopep-7 as a vector suitable for transporting agents (e.g., for treatment of diseases associated with these tissues, such as cancer or any of the diseases described herein). We also have identified other polypeptides, including Angiopep-3, Angiopep-4a, Angiopep-4b, Angiopep-5, and Angiopep-6, which also may be used as vectors in the invention. These polypeptides may retain the ability to be efficiently transported across the BBB, or to be transported into particular tissues or cell types (e.g., liver, lungs, kidneys, spleen, and muscle). For these polypeptides, agents which are unable or ineffective at efficiently crossing the BBB, may be transported across the BBB when conjugated to the polypeptide. Conjugates can be in the form of a composition, such as a pharmaceutical composition, for treatment or diagnosis of a condition or disease.

The conjugates of the invention (e.g., any of those described herein) may also have advantageous in vivo pharmacokinetic properties as compared to the agent alone. These properties may include increased half-life in vivo or increased concentration in, increased rate of accumulation in, or decreased removal from a desired cell type. On this basis, it may be possible to administer conjugates of the invention to a subject either at a lower dosage, less frequently, or for a shorter duration than the unconjugated agent. Lower amounts, frequency, or duration of administration may be especially desirable for therapeutics with known side effects. In other cases, the conjugating the agent to a polypeptide described herein may result in higher efficacy, due to increased concentration in the target cells or tissue. Indeed, by concentrating the agent in a target cell type, unwanted side effects can be reduced (e.g., with increased efficacy). This may decrease the required duration of therapy. In some cases, it may even be possible to administer the conjugate at an increased dosage, frequency, or duration, relative to the dosage of the unconjugated agent and observe increased efficacy, reduced side effects, or both.

Polypeptides of the Invention

The invention features any of polypeptides described herein, for example, any of the polypeptides described in Table 1 (e.g., a polypeptide defined in any of SEQ ID NOS: 1-105 and 107-112 such as SEQ ID NOS:1-97, 99, 100, 101, or 107-112), or any fragment, analog, derivative, or variant thereof. In certain embodiments, the polypeptide may have at least 35%, 40%, 50%, 60%, 70%, 80%, 90%, 95%, 99%, or even 100% identity to a polypeptide described herein. The polypeptide may have one or more (e.g., 2, 3, 4, 5, 6, 7, 8, 9, 10, 11, 12, 13, 14, or 15) substitutions relative to one of the sequences described herein. Other modifications are described in greater detail below.

The invention also features fragments of these polypeptides (e.g., a functional fragment). In certain embodiments, the fragments are capable of entering or accumulating in a particular cell type (e.g., liver, lung, kidney, spleen, or muscle) or capable of crossing the BBB. Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof Other fragments include sequences where internal portions of the polypeptide are deleted.

Additional polypeptides may be identified by using one of the assays or methods described in U.S. Patent Application Publication No. 2006/0189515, which is hereby incorporated by reference, or by any method known in the art. For example, a candidate vector may be produced by conventional polypeptide synthesis, conjugated with Taxol and administered to a laboratory animal. A biologically active vector may be identified, for example, based on its efficacy to increase survival of an animal injected with tumor cells and treated with the conjugate as compared to a control which has not been treated with a conjugate (e.g., treated with the unconjugated agent).

In another example, a biologically active polypeptide may be identified based on its location in the parenchyma in an in situ cerebral perfusion assay. In vitro BBB assays, such as the model developed by CELLIAL™ Technologies, may be used to identify such vectors.

Assays to determine accumulation in other tissues may be performed as well. See, for example, Example 1 herein. Labeled conjugates of a polypeptide can be administered to an animal, and accumulation in different organs can be measured. For example, a polypeptide conjugated to a detectable label (e.g., a near-IR fluorescence spectroscopy label such as Cy5.5) allows live in vivo visualization. Such a polypeptide can be administered to an animal, and the presence of the polypeptide in an organ can be detected, thus allowing determination of the rate and amount of accumulation of the polypeptide in the desired organ. In other embodiments, the polypeptide can be labeled with a radioactive isotope (e.g., $^{125}$I). The polypeptide is then administered to an animal. After a period of time, the animal is sacrificed, and the animal's organs are extracted. The amount of radioisotope in each organ can then measured using any means known in the art. By comparing the amount of a labeled candidate polypeptide in a particular organ without amount of labeled control, the ability of the candidate polypeptide the rate or amount of accumulation of a candidate polypeptide in a particular tissue can be ascertained. Appropriate negative controls include any polypeptide known not be transported into a particular cell type.

TABLE 1

| SEQ ID NO: | |
|---|---|
| 1 | T F V Y G G C R A K R N N F K S A E D |
| 2 | T F Q Y G G C M G N G N N F V T E K E |
| 3 | P F F Y G G C G G N R N N F D T E E Y |
| 4 | S F Y Y G G C L G N K N N Y L R E E E |
| 5 | T F F Y G G C R A K R N N F K R A K Y |
| 6 | T F F Y G G C R G K R N N F K R A K Y |

TABLE 1-continued

| SEQ ID NO: | Sequence |
|---|---|
| 7 | T F F Y G G C R A K K N N Y K R A K Y |
| 8 | T F F Y G G C R G K K N N F K R A K Y |
| 9 | T F Q Y G G C R A K R N N F K R A K Y |
| 10 | T F Q Y G G C R G K K N N F K R A K Y |
| 11 | T F F Y G G C L G K R N N F K R A K Y |
| 12 | T F F Y G G S L G K R N N F K R A K Y |
| 13 | P F F Y G G C G G K K N N F K R A K Y |
| 14 | T F F Y G G C R G K G N N Y K R A K Y |
| 15 | P F F Y G G C R G K R N N F L R A K Y |
| 16 | T F F Y G G C R G K R N N F K R E K Y |
| 17 | P F F Y G G C R A K K N N F K R A K E |
| 18 | T F F Y G G C R G K R N N F K R A K D |
| 19 | T F F Y G G C R A K R N N F D R A K Y |
| 20 | T F F Y G G C R G K K N N F K R A E Y |
| 21 | P F F Y G G C G A N R N N F K R A K Y |
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | I F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | I F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |

TABLE 1-continued

| SEQ ID NO: | |
|---|---|
| 83 | T F F Y G G C L G N R N N F K T E E Y |
| 84 | T F F Y G C G R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |
| 111 | I F F Y G G S R G K R N N F R T E E Y |
| 112 | T F F Y G G S R G R R N N F R T E E Y |

Peptide no. 5 includes the sequence of SEQ ID NO: 5 and is amidated at its C-terminus (see for example FIG. 1).
Peptide No. 67 includes the sequence of SEQ ID NO: 67 and is amidated at its C-terminus (see for example FIG. 1).
Peptide No. 76 includes the sequence of SEQ ID NO: 76 and is amidated at its C-terminus (see for example FIG. 1).
Peptide no. 91 includes the sequence of SEQ ID NO: 91 and is amidated at its C-terminus (see for example FIG. 1).
Peptide No. 107 includes the sequence of SEQ ID NO: 97 and is acetylated at its N-10 terminus.
Peptide No. 109 includes the sequence of SEQ ID NO: 109 and is acetylated at its N-terminus.
Peptide No. 110 includes the sequence of SEQ ID NO: 110 and is acetylated at its N-terminus.

The amine groups of Angiopep-1 (SEQ ID NO:67) and Angiopep-2 (SEQ ID NO:97) have been used as sites for conjugation of agents. To study the role of amine groups in conjugation and their impact in the overall transport capacity of these vectors, new vectors, based on the Angiopep-1 and Angiopep-2 sequence, were designed with variable reactive amine groups and variable overall charge. These polypeptides are shown in Table 2.

TABLE 2

Vectors with variable amine group targets

| Polypeptide Name | Polypeptide Sequences | Reactive amines (positions) | Charge | SEQ ID No. |
|---|---|---|---|---|
| Angiopep-3* | Ac$^1$-TFFYGGSRGKRNNFKTEEY | 2 (10, 15) | +1 | 107 |
| Angiopep-4b | RFFYGGSRGKRNNFKTEEY | 3 (1, 10, 15) | +3 | 108 |
| Angiopep-4a | Ac$^1$-RFFYGGSRGKRNNFKTEEY | 2 (10, 15) | +2 | 109 |
| Angiopep-5 | Ac$^1$-RFFYGGSRGKRNNFRTEEY | 1 (10) | +2 | 110 |
| Angiopep-6 | TFFYGGSRGKRNNFRTEEY | 2 (1, 10) | +2 | 111 |
| Angiopep-7 | TFFYGGSRGRRNNFRTEEY | 1 (1) | +2 | 112 |

*Angiopep-3 is an acetylated form of Angiopep-2.
$^1$Ac represents acetylation.

Modified Polypeptides

The invention also includes a polypeptide having a modification of an amino acid sequence described herein (e.g., polypeptide having a sequence described in any one of SEQ ID NOS:1-105 and 107-112 such as Angiopep-3, -4a, -4b, -5, -6, or -7). In certain embodiments, the modification does not destroy significantly a desired biological activity. In some embodiments, the modification may cause a reduction in biological activity (e.g., by at least 5%, 10%, 20%, 25%, 35%, 50%, 60%, 70%, 75%, 80%, 90%, or 95%). In other embodiments, the modification has no effect on the biological activity or may increase (e.g., by at least 5%, 10%, 25%, 50%, 100%, 200%, 500%, or 1,000%) the biological activity of the original polypeptide. The modified polypeptide may have or may optimize one or more of the characteristics of a polypeptide of the invention which, in some instance might be needed or desirable. Such characteristics include in vivo stability, bioavailability, toxicity, immunological activity, or immunological identity.

Polypeptides of the invention may include amino acids or sequences modified either by natural processes, such as post-translational processing, or by chemical modification techniques known in the art. Modifications may occur anywhere in a polypeptide including the polypeptide backbone, the amino acid side-chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide may further include an amino acid insertion, deletion, or substitution, either conservative or non-conservative (e.g., D-amino acids, desamino acids) in the polypeptide sequence (e.g., where such changes do not substantially alter the biological activity of the polypeptide).

Substitutions may be conservative (i.e., wherein a residue is replaced by another of the same general type or group) or non-conservative (i.e., wherein a residue is replaced by an amino acid of another type). In addition, a non-naturally occurring amino acid may substituted for a naturally occurring amino acid (i.e., non-naturally occurring conservative amino acid substitution or a non-naturally occurring non-conservative amino acid substitution).

Polypeptides made synthetically may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogues may be generated by substitutional mutagenesis and retain the biological activity of the original polypeptide. Examples of substitutions identified as "conservative substitutions" are shown in Table 3. If such substitutions result in a change not desired, then other type of substitutions, denominated "exemplary substitutions" in Table 3, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe), (2) neutral hydrophilic: Cysteine (Cys), Serine (Ser), Threonine (Thr)

(3) acidic/negatively charged: Aspartic acid (Asp), Glutamic acid (Glu)

(4) basic: Asparagine (Asn), Glutamine (Gln), Histidine (His), Lysine (Lys), Arginine (Arg)

(5) residues that influence chain orientation: Glycine (Gly), Proline (Pro);

(6) aromatic: Tryptophan (Trp), Tyrosine (Tyr), Phenylalanine (Phe),

Histidine (His), (7) polar: Ser, Thr, Asn, Gln (8) basic positively charged: Arg, Lys, His, and;

(9) charged: Asp, Glu, Arg, Lys, His

Other conservative amino acid substitutions are listed in Table 3.

TABLE 3

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Additional Analogues

The polypeptides and conjugates of the invention may include polypeptide analogs of aprotinin known in the art. For example, U.S. Pat. No. 5,807,980 describes Bovine Pancreatic Trypsin Inhibitor (aprotinin)-derived inhibitors as well as a method for their preparation and therapeutic use, including the polypeptide of SEQ ID NO:102. These polypeptides have been used for the treatment of a condition characterized by an abnormal appearance or amount of tissue factor and/or factor VIIIa such as abnormal thrombosis. U.S. Pat. No. 5,780,265 describes serine protease inhibitors capable of inhibiting plasma kallikrein, including SEQ ID NO:103. U.S. Pat. No. 5,118,668 describes Bovine Pancreatic Trypsin Inhibitor variants, including SEQ ID NO:105. The aprotinin amino acid sequence (SEQ ID NO:98), the Angiopep-1 amino acid sequence (SEQ ID NO:67), and SEQ ID NO:104, as well as some sequences of biologically active analogs may be found in International Application Publication No. WO 2004/060403.

An exemplary nucleotide sequence encoding an aprotinin analogue is illustrated in SEQ ID NO:106 (atgagaccag atttct-gcct cgagccgccg tacactgggc cctgcaaagc tcgtatcatc cgttacttct acaatgcaaa ggcaggcctg tgtcagacct tcgtatacgg cggctgcaga gctaagcgta acaacttcaa atccgcggaa gactgcatgc gtacttgcgg tggt-gcttag; Genbank accession No. X04666). This sequence encodes a lysine at position 16 instead of a valine, as found in SEQ ID NO:98. A mutation in the nucleotide sequence of SEQ ID NO:106 may be introduced by methods known in the art to change the produce the polypeptide of SEQ ID NO:98 having a valine in position 16. Additional mutations or fragments may be obtained using any technique known in the art.

Other examples of aprotinin analogs may be found by performing a protein BLAST using the synthetic aprotinin sequence (or portion thereof) disclosed in International Application No. PCT/CA2004/000011. Exemplary aprotinin analogs are found under accession Nos. CAA37967 (GI: 58005) and 1405218C (GI:3604747).

Preparation of Polypeptide Derivatives and Peptidomimetics

In addition to polypeptides consisting only of naturally occurring amino acids, peptidomimetics or polypeptide analogs are also encompassed by the present invention. Polypeptide analogs are commonly used in the pharmaceutical industry as non-polypeptide drugs with properties analogous to those of the template polypeptide. The non-polypeptide compounds are termed "polypeptide mimetics" or peptidomimetics (Fauchere et al., Infect. Immun. 54:283-287,1986; Evans et al., J. Med. Chem. 30:1229-1239, 1987). Polypeptide mimetics that are structurally related to therapeutically useful polypeptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —$CH_2NH$—, —$CH_2S$—, —$CH_2$—$CH_2$—, —$CH$=$CH$— (cis and trans), —$CH_2SO$—, —$CH(OH)CH_2$—, —$COCH_2$— etc., by methods well known in the art (Spatola, Peptide Backbone Modifications, Vega Data, 1(3):267, 1983); Spatola et al. (Life Sci. 38:1243-1249, 1986); Hudson et al. (Int. J. Pept. Res. 14:177-185, 1979); and Weinstein. B., 1983, Chemistry and Biochemistry, of Amino Acids, Peptides and Proteins, Weinstein eds, Marcel Dekker, New-York). Such polypeptide mimetics may have significant advantages over naturally-occurring polypeptides including more economical production, greater chemical stability, enhanced pharmacological properties (e.g., half-life, absorption, potency, efficiency), reduced antigenicity and others.

While the polypeptides of the invention may be effective in entering particular cell types (e.g., those described herein), their effectiveness may be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the polypeptide and require a free N-terminus (Powell et al., Pharm. Res. 10:1268-1273, 1993). In light of this, it is often advantageous to use modified versions of polypeptides. The modified polypeptides retain the structural characteristics of the original L-amino acid polypeptides that confer biological activity with regard to IGF-1, but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable polypeptides. Thus, a polypeptide derivative or peptidomimetic of the present invention may be all L, all D or mixed D, L polypeptide. The presence of an N-terminal or C-terminal D-amino acid increases the in vivo stability of a polypeptide because peptidases cannot utilize a D-amino acid as a substrate (Powell et al., Pharm. Res. 10:1268-1273, 1993). Reverse-D polypeptides are polypeptides containing D-amino acids, arranged in a reverse sequence relative to a polypeptide containing L-amino acids. Thus, the C-terminal residue of an L-amino acid polypeptide becomes N-terminal for the D-amino acid polypeptide, and so forth. Reverse D-polypeptides retain the same tertiary conformation and therefore the same activity, as the L-amino acid polypeptides, but are more stable to enzymatic degradation in vitro and in vivo, and thus have greater therapeutic efficacy than the original polypeptide (Brady and Dodson, Nature 368:692-693, 1994; Jameson et al., Nature 368:744-746, 1994). In addition to reverse-D-polypeptides, constrained polypeptides comprising a consensus sequence or a substantially identical consensus sequence variation may be generated by methods well known in the art (Rizo and Gierasch, Ann. Rev. Biochem. 61:387-418, 1992). For example, constrained polypeptides may be generated by adding cysteine residues capable of forming disulfide bridges and, thereby, resulting in a cyclic polypeptide. Cyclic polypeptides have no free N- or C-termini. Accordingly, they are not susceptible to proteolysis by exopeptidases, although they are, of course, susceptible to endopeptidases, which do not cleave at peptide termini. The amino acid sequences of the polypeptides with N-terminal or C-terminal D-amino acids and of the cyclic polypeptides are usually identical to the sequences of the polypeptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., J. Pharm. Pharmacol. 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the polypeptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S— alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., *Pharm. Res.* 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified polypeptides consisting of polypeptides bearing an N-terminal acetyl group and/or a C-terminal amide group.

Also included by the present invention are other types of polypeptide derivatives containing additional chemical moieties not normally part of the polypeptide, provided that the derivative retains the desired functional activity of the polypeptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives.

Longer polypeptide sequences which result from the addition of additional amino acid residues to the polypeptides of the invention are also encompassed in the present invention. Such longer polypeptide sequences would be expected to have the same biological activity (e.g., entering particular cell types) as the polypeptides described above. While polypeptides having a substantial number of additional amino acids are not excluded, it is recognized that some large polypeptides may assume a configuration that masks the effective sequence, thereby preventing binding to a target (e.g., a member of the LRP receptor family such as LRP or LRP2). These derivatives could act as competitive antagonists. Thus, while the present invention encompasses polypeptides or derivatives of the polypeptides described herein having an extension, desirably the extension does not destroy the cell targeting activity of the polypeptide or derivative.

Other derivatives included in the present invention are dual polypeptides consisting of two of the same, or two different polypeptides of the present invention covalently linked to one another either directly or through a spacer, such as by a short stretch of alanine residues or by a putative site for proteolysis (e.g., by cathepsin, see e.g., U.S. Pat. No. 5,126,249 and European Patent No. 495 049). Multimers of the polypeptides of the present invention consist of polymer of molecules formed from the same or different polypeptides or derivatives thereof.

The present invention also encompasses polypeptide derivatives that are chimeric or fusion proteins containing a polypeptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids of a polypeptide of the present invention and desirably has a functional activity equivalent or greater than a polypeptide of the invention.

Polypeptide derivatives of the present invention can be made by altering the amino acid sequences by substitution, addition, or deletion or an amino acid residue to provide a functionally equivalent molecule, or functionally enhanced or diminished molecule, as desired. The derivative of the present invention include, but are not limited to, those containing, as primary amino acid sequence, all or part of the amino acid sequence of the polypeptides described herein (e.g., any one of SEQ ID NOS:1-105 and 107-112) including altered sequences containing substitutions of functionally equivalent amino acid residues. For example, one or more amino acid residues within the sequence can be substituted by another amino acid of a similar polarity which acts as a functional equivalent, resulting in a silent alteration. Substitution for an amino acid within the sequence may be selected from other members of the class to which the amino acid belongs. For example, the positively charged (basic) amino acids include, arginine, lysine and histidine. The nonpolar (hydrophobic) amino acids include, leucine, isoleucine, alanine, phenylalanine, valine, proline, tryptophan and methionine. The uncharged polar amino acids include serine, threonine, cysteine, tyrosine, asparagine and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

Assays to Identify Peptidomimetics

As described above, non-peptidyl compounds generated to replicate the backbone geometry and pharmacophore display (peptidomimetics) of the polypeptides identified by the methods of the present invention often possess attributes of greater metabolic stability, higher potency, longer duration of action and better bioavailability.

The peptidomimetics compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, *Anticancer Drug Des.* 12:145, 1997). Examples of methods for the synthesis of molecular libraries can be found in the art, for example, in: DeWitt et al. (*Proc. Natl. Acad. Sci. USA* 90:6909, 1993); Erb et al. (*Proc. Natl. Acad. Sci. USA* 91:11422, 1994); Zuckermann et al., *J. Med. Chem.* 37:2678, 1994); Cho et al. (*Science* 261:1303, 1993); Carell et al. (*Angew. Chem, Int. Ed. Engl.* 33:2059, 1994 and ibid 2061); and in Gallop et al. (*Med. Chem.* 37:1233, 1994). Libraries of compounds may be presented in solution (e.g., Houghten, *Biotechniques* 13:412-421, 1992) or on beads (Lam, *Nature* 354:82-84, 1991), chips (Fodor, *Nature* 364:555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990), or luciferase, and the enzymatic label detected by determination of conversion of an appropriate substrate to product.

Once a polypeptide of the present invention is identified, it may be isolated and purified by any number of standard methods including, but not limited to, differential solubility (e.g., precipitation), centrifugation, chromatography (e.g., affinity, ion exchange, size exclusion, and the like) or by any other standard techniques used for the purification of polypeptides, peptidomimetics or proteins. The functional properties of an identified polypeptide of interest may be evaluated using any functional assay known in the art. Desirably, assays for evaluating downstream receptor function in intracellular signaling are used (e.g., cell proliferation).

For example, the peptidomimetics compounds of the present invention may be obtained using the following three-phase process: (1) scanning the polypeptides of the present invention to identify regions of secondary structure necessary for targeting the particular cell types described herein; (2) using conformationally constrained dipeptide surrogates to refine the backbone geometry and provide organic platforms corresponding to these surrogates; and (3) using the best organic platforms to display organic pharmocophores in libraries of candidates designed to mimic the desired activity of the native polypeptide. In more detail the three phases are as follows. In phase 1, the lead candidate polypeptides are scanned and their structure abridged to identify the requirements for their activity. A series of polypeptide analogs of the original are synthesized. In phase 2, the best polypeptide analogs are investigated using the conformationally constrained dipeptide surrogates. Indolizidin-2-one, indolizidin-9-one and quinolizidinone amino acids ($I^2$aa, $I^9$aa and Qaa respectively) are used as platforms for studying backbone geometry of the best polypeptide candidates. These and related platforms (reviewed in Halab et al., *Biopolymers* 55:101-122, 2000; and Hanessian et al. *Tetrahedron* 53:12789-12854, 1997) may be introduced at specific regions of the polypeptide to orient the pharmacophores in different directions. Biological evaluation of these analogs identifies improved lead polypeptides that mimic the geometric requirements for activity. In phase 3, the platforms from the most active lead polypeptides are used to display organic surrogates of the pharmacophores responsible for activity of the native polypeptide. The pharmacophores and scaffolds are combined in a parallel synthesis format. Derivation of polypeptides and the above phases can be accomplished by other means using methods known in the art.

Structure function relationships determined from the polypeptides, polypeptide derivatives, peptidomimetics, or other small molecules of the present invention may be used to refine and prepare analogous molecular structures having similar or better properties. Accordingly, the compounds of the present invention also include molecules that share the structure, polarity, charge characteristics, and side chain properties of the polypeptides described herein.

In summary, based on the disclosure herein, those skilled in the art can develop polypeptides and peptidomimetics screening assays which are useful for identifying compounds for targeting an agent to particular cell types (e.g., those described herein). The assays of this invention may be developed for low-throughput, high-throughput, or ultra-high throughput screening formats. Assays of the present invention include assays which are amenable to automation.

Conjugates of the Invention

The polypeptides described herein or derivatives thereof may be linked to an agent. For example, the polypeptide (e.g., Angiopep-7) may be attached to a therapeutic agent, a diagnostic agent, or to a label. In certain embodiments, the polypeptide is linked to or labeled with a detectable label, such as a radioimaging agent, for diagnosis of a disease or condition. Examples of these agents include a radioimaging agent-antibody-vector conjugate, where the antibody binds to a disease or condition-specific antigen (e.g., for diagnosis or therapy). Other binding molecules are also contemplated by the invention. In other cases, the polypeptide or derivative is linked to a therapeutic agent, to treat a disease or condition, or may be linked to or labeled with mixtures thereof. The disease or condition may be treated by administering a vector-agent conjugate to an individual under conditions which allow transport of the agent across the BBB or into a particular cell type. Each polypeptide may include at least 1, 2, 3, 4, 5, 6, or 7 agents. In other embodiments, each agent has at least 1, 2, 3, 4, 5, 6 7, 10, 15, 20, or more polypeptides attached thereto. The conjugates of the invention may be able to promote accumulation (e.g., due to increased uptake or reduced removal) of the agent in a particular cell type or tissue such as liver, lung, kidney, spleen or muscle of a subject.

The agent may be releasable from the vector after transport into a particular cell type or across the BBB. The agent can be released, for example, by enzymatic cleavage or other breakage of a chemical bond between the vector and the agent. The released agent may then function in its intended capacity in the absence of the vector.

Therapeutic Agents

A therapeutic agent may be any biologically active agent. For example, a therapeutic may be a drug, a medicine, an agent emitting radiation, a cellular toxin (for example, a chemotherapeutic agent), a biologically active fragment thereof, or a mixture thereof to treat a disease (e.g., to killing cancer cells) or it may be an agent to treat a disease or condition in an individual. A therapeutic agent may be a synthetic product or a product of fungal, bacterial or other microorganism (e.g., mycoplasma or virus), animal, such as reptile, or plant origin. A therapeutic agent and/or biologically active fragment thereof may be an enzymatically active agent and/or fragment thereof, or may act by inhibiting or blocking an important and/or essential cellular pathway or by competing with an important and/or essential naturally occurring cellular component. Other therapeutic agents include antibodies and antibody fragments.

Anticancer agents. Any anticancer agent known in the art may be part of a conjugate of the invention. Cancers of the brain may be treated with a conjugate containing a vector that is efficiently transported across the BBB (e.g., Angiopep-3, Angiopep-4a, Angiopep-4b, Angiopep-5, or Angiopep-6). Liver, lung, kidney, or spleen cancers may be treated with an anticancer agent conjugated to a vector that is transported efficiently into the appropriate cell type (e.g., Angiopep-7). Exemplary agents include abarelix, aldesleukin, alemtuzumab, alitertinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin (e.g., sodium), darbepoetin alfa, dasatinib, daunorubicin, daunomycin, decitabine, denileukin, denileukin diftitox, dexrazoxane, docetaxel, doxorubicin, dromostanolone propionate, eculizumab, epirubicin (e.g., HCl), epoetin alfa, erlotinib, estramustine, etoposide (e.g., phosphate), exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), Interferon alfa-2b, irinotecan, lapatinib ditosylate, lenalidomide, letrozole, leucovorin, leuprolide (e.g., acetate), levamisole, lomustine, CCNU, meclorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa-2b, pemeterxed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., hcl), toremifene, Tositumomab/I-131 (tositumomab), trastuzumab, trastuzumab, tretinoin (ATRA), uracil mustard, valrubicin, vinblastine, vincristine, vinorelbine, vorinostat, zoledronate, and zoledronic acid. Exemplary derivatives of paclitaxel are described in U.S. Pat. No. 6,911,549, the entire contents of which are hereby incorporated by reference.

Detectable Labels

For the purpose of detection or diagnosis, the conjugate of the invention may be labeled. Detectable labels, or markers, may be a radiolabel, a fluorescent label, a nuclear magnetic resonance active label, a luminescent label, a chromophore label, a positron emitting isotope for PET scanner, chemiluminescence label, or an enzymatic label. Exemplary radioimaging agents emitting radiation (detectable radiolabels) include indium-111, technitium-99, or low dose iodine-131. Gamma and beta emitting radionuclides include $^{67}$Cu, $^{67}$Ga, $^{90}$Y, $^{111}$In, $^{99m}$Tc, and $^{201}$Tl). Positron emitting radionuclides include $^{18}$F, $^{55}$Co, $^{60}$Cu, $^{62}$Cu, $^{64}$Cu, $^{66}$G$_a$, $^{68}$Ga, $^{82}$Rb, and $^{86}$Y. Fluorescent labels include Cy5.5, green fluorescent protein (GFP), fluorescein, and rhodamine. Chemiluminescence labels include luciferase and β-galactosidase. Enzymatic labels include peroxidase and phosphatase. A histag may also be a detectable label. For example, conjugates may include a vector moiety and an antibody moiety (antibody or antibody fragment), which may further include a label. In this case, the label may be attached to either the vector or to the antibody.

Antibodies

Antibodies may also be conjugated to the polypeptides of the invention by any means known in the art (e.g., using the conjugation strategies described herein). Any diagnostic or therapeutic antibody may be conjugated to one or more (e.g., 2, 3, 4, 5, 6, 7, 8, 9, 10, or more) vectors of the invention. In addition, antibody fragments (e.g., capable of binding to an antigen) may also be conjugated to the vectors of the invention. Antibody fragments include the Fab and Fc regions, heavy chain, and light chain of an antibody (e.g., of any antibody described herein). Exemplary antibodies for use in diagnosis and therapy of cancer include ABX-EGF (Panitimumab), OvaRex (Oregovemab), Theragyn (pemtumomabytrrium-90), Therex, Bivatuzumab, Panorex (Edrecolomab), ReoPro (Abciximab), Bexxar (Tositumomab), MAb, idiotypic 105AD7, Anti-EpCAM (Catumaxomab), MAb lung cancer (from Cytoclonal), Herceptin (Trastuzumab), Rituxan (Rituximab), Avastin (Bevacizumab), AMD Fab (Ranibizumab), E-26 (2$^{nd}$ gen. IgE) (Omalizumab), Zevalin (Rituxan+yttrium-90) (Ibritumomab tiuxetan), Cetuximab, BEC2 (Mitumomab), IMC-1C11, nuC242-DM1, LymphoCide (Epratuzumab), LymphoCide Y-90, CEA-Cide (Labetuzumab), CEA-Cide Y-90, CEA-Scan (Tc-99m-labeled arcitumomab), LeukoScan (Tc-99m-labeled sulesomab), LymphoScan (Tc-99m-labeled bectumomab), AFP-Scan (Tc-99m-labeled), HumaRAD-HN (+yttrium-90), HumaSPECT (Votumumab), MDX-101 (CTLA-4), MDX-210 (her-2 overexpression), MDX-210/MAK, Vitaxin, MAb 425, IS-IL-2, Campath (alemtuzumab), CD20 streptavidin, Avidicin, (albumin+NRLU13), Oncolym (+iodine-131) Cotara (+iodine-131), C215 (+staphylococcal enterotoxin, MAb lung/kidney cancer (from Pharmacia Corp.), nacolomab tafenatox (C242 staphylococcal enterotoxin), Nuvion (Visilizumab), SMART M195, SMART 1D10, CEAVac, TriGem, TriAb, NovoMAb-G2 radiolabeled, Monopharm C, GlioMAb-H (+gelonin toxin), Rituxan (Rituximab), and ING-1. Additional therapeutic antibodies include 5G1.1 (Ecluizumab), 5G1.1-SC (Pexelizumab), ABX-CBL (Gavilimomab), ABX-IL8, Antegren (Natalizumab), Anti-CD11a (Efalizumab), Anti-CD18 (from Genetech), Anti-LFA1, Antova, BTI-322, CDP571, CDP850, Corsevin M, D2E7 (Adalimumab), Humira (Adalimumab), Hu23F2G (Rovelizumab), IC14, IDEC-114, IDEC-131, IDEC-151, IDEC-152, Infliximab (Remicade), LDP-01, LDP-02, MAK-195F (Afelimomab), MDX-33, MDX-CD4, MEDI-507 (Siplizumab), OKT4A, OKT3 (Muromonab-CD3), and ReoPro (Abciximab).

Conjugation Linkers

The conjugate (e.g., a protein-protein conjugate) may be obtained using any cross-linking (conjugation) reagent or protocol know in the art, many of which are commercially available. Such protocols and reagents include, cross-linkers reactive with amino, carboxyl, sulfhydryl, carbonyl, carbohydrate and/or phenol groups. The amounts, times, and conditions of such protocols can be varied to optimize conjugation. Cross-linking reagents contain at least two reactive groups and are generally divided into homofunctional cross-linkers (containing identical reactive groups) and heterofunctional cross-linkers (containing non-identical reactive groups). The cross-linkers of the invention may be either homobifunctional and/or heterobifunctional. Furthermore the cross-linker may incorporate a 'spacer' between the reactive moieties, or the two reactive moieties in the cross-linker may be directly linked. Bonds may include ester bonds.

Figure 3:
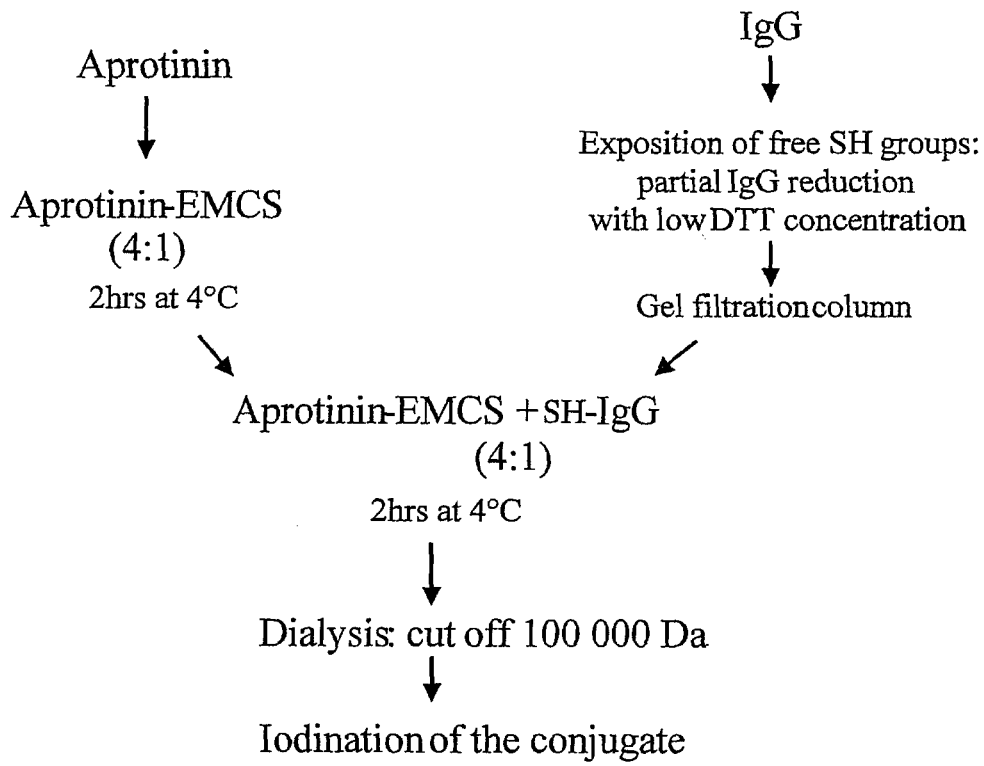
FIG. 3 illustrates the protocol used to conjugate aprotinin with IgG using cross-linker sulfo-EMCS.
Figure 5:
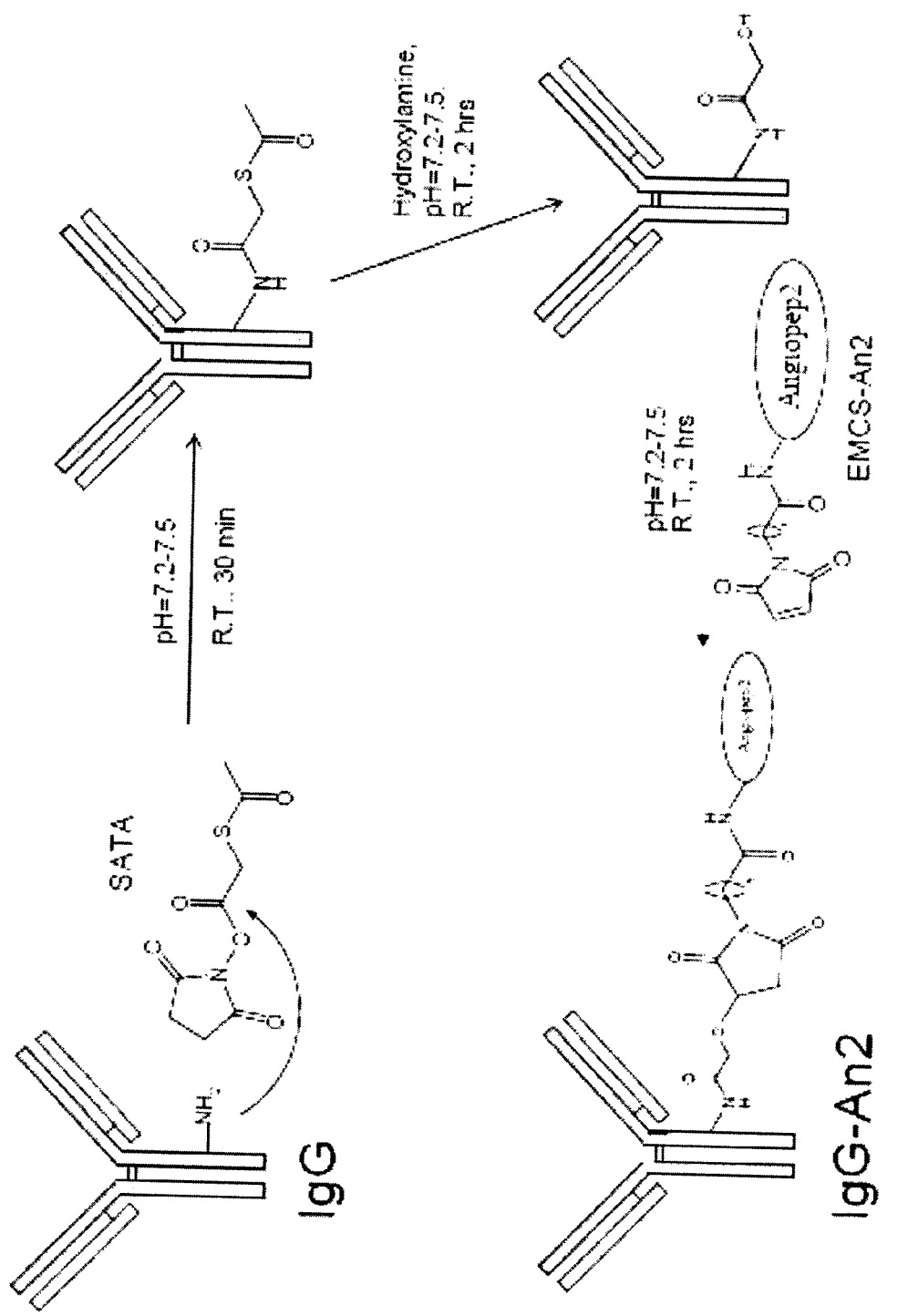
FIG. 5 illustrates the protocol used to conjugate Angiopep-2 with antibodies using cross-linker SATA.
Figure 6:
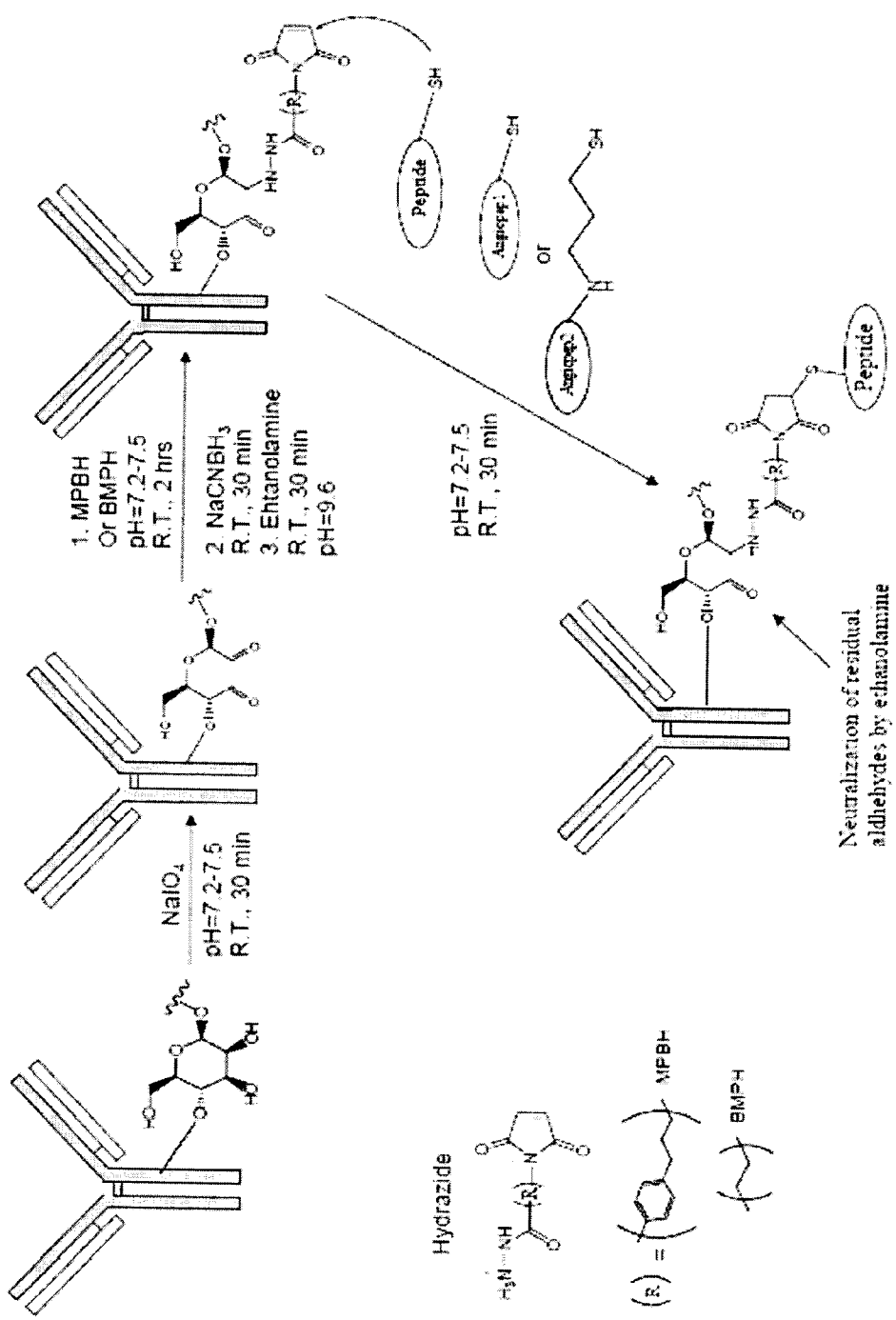
FIG. 6 illustrates the protocol used to conjugate Angiopep-2 with antibodies using carbohydrate targets via hydrazide.
Figure 7:
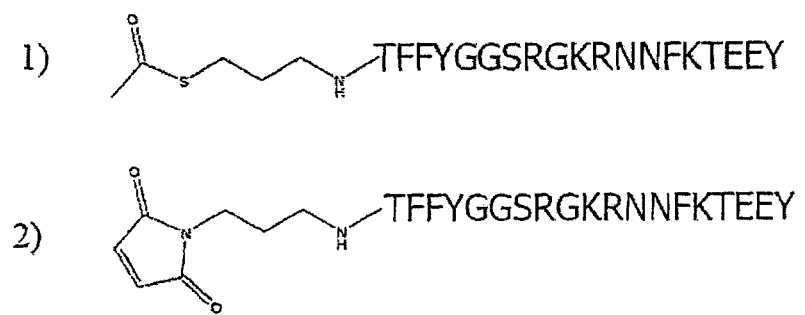
FIG. 7 illustrates other possible linkers which may be used in the making of a conjugate attached to a polypeptide with the amino acid sequence SEQ ID NO: 97.

Exemplary linkers include BS$^3$ [Bis(sulfosuccinimidyl) suberate], NHS/EDC (N-hydroxysuccinimide and N-ethyl-(dimethylaminopropyl)carbodimide, Sulfo-EMCS ([N-e-Maleimidocaproic acid]hydrazide), SATA (N-succinimidyl-S-acetylthioacetate), and hydrazide. BS$^3$ is a homobifunctional N-hydroxysuccinimide ester that targets accessible primary amines. A conjugation scheme is exemplified in FIG. 2. NHS/EDC allows for the conjugation of primary amine groups with carboxyl groups. Sulfo-EMCS are heterobifunctional reactive groups (maleimide and NHS-ester) that are reactive toward sulfhydryl and amino groups. Amine coupling using sulfo-NHS/EDC activation may be used to cross-link therapeutic antibodies with the polypeptides of the invention, as exemplified in FIGS. 3 and 4. This is a fast, simple and reproducible coupling technique. The resulting conjugate is stable and retains the biological activity of the antibody. Moreover, it has a high conjugation capacity that can be reliably controlled and a low non-specific interaction during coupling procedures. SATA is reactive towards amines and adds protected sulfhydryls groups. The NHS-ester reacts with primary amines to form stable amide bonds. Sulfhydryl groups may be deprotected using hydroxylamine. This conjugation method is exemplified in FIG. 5. Hydrazide can be used to link carboxyl groups to primary amines, as shown in FIG. 6, and may therefore be useful for linking glycoproteins. Additional exemplary linkers are illustrated in FIG. 7.

Figure 8:
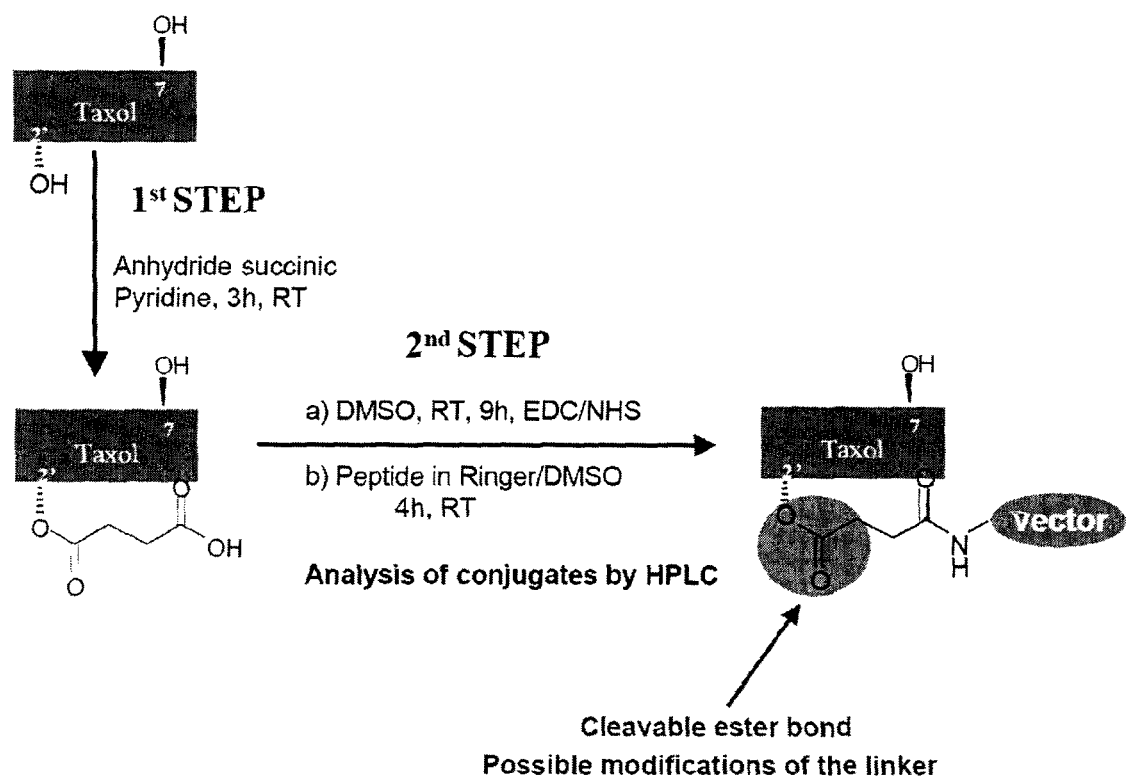
FIG. 8 illustrates a method for attaching a vector of the invention to paclitaxel.

Small molecules such as therapeutic agents can be conjugated to the polypeptides of the invention. The exemplary small molecule, paclitaxel, has two strategic positions (position C2' and C7) useful for conjugation. Conjugation of a vector or vector of the invention to paclitaxel can be performed as follows (FIG. 8). Briefly, paclitaxel is reacted with anhydride succinic pyridine for three hours at room temperature to attach a succinyl group in position 2'. The 2'-succinyl paclitaxel has a cleavable ester bond in position 2' can simply release succinic acid. This cleavable ester bond can be further used for various modifications with linkers, if desired. The resulting 2'-O-succinyl-paclitaxel is then reacted with EDC/NHS in DMSO for nine hours at room temperature, followed by the addition of the vector or vector in Ringer/DMSO for an additional reaction time of four hours at room temperature. The reaction of conjugation depicted in FIG. 8 is monitored by HPLC. Each intermediate, such as paclitaxel, 2'-O-succinyl-paclitaxel and 2'-O—NHS-succinyl-paclitaxel, is purified and validated using different approaches such as HPLC, thin liquid chromatography, NMR ($^{13}$C or $^1$H exchange), melting point, or mass spectrometry. The final conjugate is analyzed by mass spectrometry and SDS-polyacrylamide gel electrophoresis. This allows determining the number of paclitaxel molecules conjugated on each vector.

Conjugate Activities

By conjugating and agent to a vector described herein, desirable properties, such as altered pharmacokinetics, altered tissue distribution (e.g., increased delivery to particular tissues or cell types such as liver, brain, lung, spleen, or kidney) may be achieved. Briefly, we have identified vectors that efficiently transport agents across the BBB (e.g., Angiopep-3, Angiopep-4a, Angiopep-4b, Angiopep-5, and Angiopep-6). Like Angiopep-2, these vectors may also be capable of targeting agents to other cell types or tissues (e.g., liver, lung, kidney, spleen, or muscle). We have also identified a vector, Angiopep-7, which is not efficiently transported across the BBB, but is transported to particular tissues (e.g., liver, lung, kidney, spleen, or muscle). Accordingly, vectors with this activity may be useful where transport across the BBB is not desired.

Because the conjugates of the invention transport agents to specific tissues, conjugated agents may result in lower toxicity (e.g., fewer side effects), higher efficacy (e.g., because the agent is concentrated into a target tissue due to increased uptake or decreased efflux from the tissue or cells or because the agent has greater stability when conjugated), or a combination thereof Such activities are described below and in International Publication No. WO 2007/009229, hereby incorporated by reference.

In some cases, conjugation of an agent to a vector allows the agent to escape the action of P-glycoprotein (P-gp), an efflux pump capable of expelling certain agents from a cell. By decreasing the ability of P-gp to expel an agent from a cell, the potency of that agent in a cell can be increased. These conjugates can thus actively inhibit cancer cell proliferation. Moreover, results obtained for in vivo tumor growth indicate that the vectors of the invention may target the receptor LRP. Also, conjugation may modify the pharmacokinetics or biodistribution of the unconjugated agent.

Taken together, conjugates can be used against primary tumors including breast, lung, and skin cancers as well as metastasis originating from primary tumors.

P-glycoprotein Bypass

Figure 9:
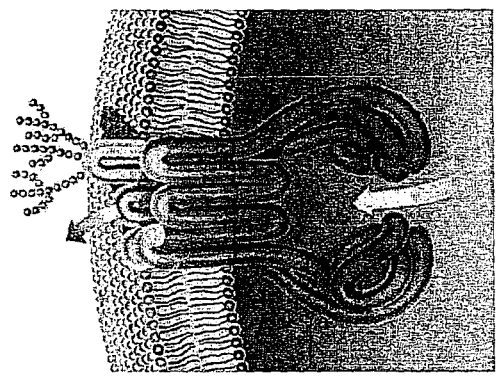
FIG. 9 is a schematic representation of the efflux pump, P-glycoprotein (P-gp or MDR1) at the cell surface. The efflux pump, P-gp or MDR1, associated with multidrug resistance is highly expressed at the cell surface of many cancer cells and various tissues including the blood-brain barrier (BBB).

Because the resistance towards various chemotherapeutic agents such as vincristine, etoposide, and doxorubicin is mediated through P-gp (MDR1) overexpression (FIG. 9), bypassing this efflux pump may potentiate the action of these drugs on various cancer types. By conjugating a vector to such an agent, it is now possible to decrease P-gp mediated efflux of the agent. These conjugates may be useful for increasing the potency of drugs associated with resistance mediated by P-gp. As exemplified below, the vectors described herein were tested for their ability to avoid expulsion by P-gp.

LRP Mediated Uptake

Based on our previous work (see International Patent Application No. PCT/CA2004/00011, hereby incorporated by reference), receptor-associated protein (RAP) inhibited transcytosis of aprotinin in an in vitro model of the blood brain barrier. LRP is expressed on a variety of cancer cells (see, e.g., International Publication No. WO 2007/009229). We therefore proposed that the low-density lipoprotein related receptor (LRP) is involved in the penetration of aprotinin into the brain. Similar inhibition of Angiopep-1 and Angiopep-2 transport across an in vitro model of the blood-brain barrier was also obtained (data not shown) suggesting that transcytosis of these polypeptide across brain endothelial cell also involved LRP as well. On this basis, we believe that LRP may be involved, generally, in uptake of the aprotinin related polypeptides described herein.

LRP is a heterodimeric membrane receptor of 600 kDa composed of two subunits; the subunit-α (515 kDa) and the subunit-β (85 kDa). Because LRP may be involved in the transport of a vector as described herein, the conjugates of the invention may target cells and tumors expressing this receptor. Certain cancer cells, for example, express a member of the LRP (e.g., LRP or LRP2).

Methods of Treatment

The invention also features methods of treatment using the polypeptide conjugates described herein. Conjugates that are efficiently transported across the BBB (e.g., Angiopep-3, Angiopep-4a, Angiopep-4b, Angiopep-5, and Angiopep-6) may be used to treat any brain or central nervous system disease. These conjugates are also efficiently transported to the liver, lung, kidney, spleen or muscle and therefore may also be used, in conjunction with an appropriate therapeutic agent, to treat a disease associated with these tissues (e.g., a cancer). Because Angiopep-7 is not efficiently transported to the brain, but is transported efficiently to tissues and cells such as liver, lung, kidney, spleen and muscle, Angiopep-7 may be especially well suited as a vector treatment of diseases associated with these tissues when targeting the agent to the brain is not desired.

Liver diseases include amebic liver abscess, cirrhosis, disseminated coccidioidomycosis; drug-induced cholestasis, hemochromatosis, hepatitis A, hepatitis B, hepatitis C, hepatitis D, hepatocellular carcinoma, liver cancer, liver disease due to alcohol, primary biliary cirrhosis, pyogenic liver abscess, Reye' syndrome, sclerosing cholangitis, and Wilson's disease. Amebic liver abscess may be treated by administration of a vector conjugated to metronidazole. Hepatitis B may be treated, for example, by administration of vector conjugated to interferon-alpha, lamivudine, adefovir dipivoxil, entecavir, or other antiviral agent. Hepatitis C may be treated, for example, by administration of a vector conjugated to pegylated interferon or ribavirin, or a combination thereof.

Lung diseases include lung cancers such as small cell carcinoma (e.g., oat cell cancer), mixed small cell/large cell carcinoma, combined small cell carcinoma, and metastatic tumors. Metastatic tumors can originate from cancer of any tissue, including breast cancer, colon cancer, prostate cancer, sarcoma, bladder cancer, neuroblastoma, and Wilm's tumor. Spleen diseases include cancers such as lymphoma, non-Hodgkin's lymphoma, and certain T-cell lymphomas.

Additional exemplary cancers that may be treated using a conjugate or composition of the invention include hepatocellular carcinoma, breast cancer, cancers of the head and neck including various lymphomas such as mantle cell lymphoma, non-Hodgkins lymphoma, adenoma, squamous cell carcinoma, laryngeal carcinoma, cancers of the retina, cancers of the esophagus, multiple myeloma, ovarian cancer, uterine cancer, melanoma, colorectal cancer, bladder cancer, prostate cancer, lung cancer (including non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adenocarcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), comeal neovascularization, diabetic retinopathy, neovascular glaucoma, myopic degeneration and other proliferative diseases and conditions such as restenosis and polycystic kidney disease. Brain cancers that may be treated with vector that is transported efficiently across the BBB include astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, and teratoma.

A conjugate or composition of the invention may be administered by any means known in the art; e.g., orally, intraarterially, intranasally, intraperitoneally, intravenously, intramuscularly, subcutaneously, transdermally, or per os to the subject. The agent may be, for example, an anti-angiogenic compound.

Pharmaceutical Compositions

Pharmaceutical compositions of the invention may include a polypeptide or conjugate described herein, in association with a pharmaceutically acceptable carrier. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially, and intratumorally.

Pharmaceutically acceptable carriers further include 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Other formulations include poly-oxyethylene esters of a fatty acid (e.g., 12-hydroxystearic acid) such as Solutol® HS15. Thus, in some embodiments, a pharmaceutical composition may comprise a) a conjugate described herein, b) Solutol® HS15 and c) an aqueous solution or buffer (e.g., Ringer/Hepes solution at a pH of 5 to 7). The concentration of Solutol® HS 15 in the formulation may be at least 5%, 10%, 15%, 20%, 25%, 30%, 35%, 40%, 45%, 50%, or 60% (e.g., 30%) or within any range between any two of these numbers. The concentration of conjugate may be determined based upon the dose required for efficiently treating a subject, or the amount the ester required for solubility of the conjugate being administered. The use of Solutol in a formulation for administration of a Taxol conjugate is described, for example, in International Publication No. WO 2007/009229, hereby incorporated by reference.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the agent in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in *Encyclopedia of Pharmaceutical Technology*, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

Dosages

The dosage of any conjugate or composition described herein or identified using the methods described herein depends on several factors, including: the administration method, the disease (e.g., cancer) to be treated, the severity of the disease, whether the cancer is to be treated or prevented, and the age, weight, and health of the subject to be treated.

With respect to the treatment methods of the invention, it is not intended that the administration of a vector, conjugate, or composition to a subject be limited to a particular mode of administration, dosage, or frequency of dosing; the invention contemplates all modes of administration. The conjugate, or composition may be administered to the subject in a single dose or in multiple doses. For example, a compound described herein or identified using screening methods of the invention may conjugate be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the vector, conjugate, or composition. For example, the dosage of a conjugate can be increased if the lower dose does not provide sufficient activity in the treatment of a disease or condition described herein (e.g., cancer). Conversely, the dosage of the compound can be decreased if the disease (e.g., cancer) is reduced or eliminated.

While the attending physician ultimately will decide the appropriate amount and dosage regimen, a therapeutically effective amount of a vector, conjugate, or composition described herein, may be, for example, in the range of 0.0035 µg to 20 µg/kg body weight/day or 0.010 µg to 140 µg/kg body weight/week. Desirably a therapeutically effective amount is in the range of 0.025 µg to 10 µg/kg, for example, at least 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 µg/kg body weight administered daily, every other day, or twice a week. In addition, a therapeutically effective amount may be in the range of 0.05 µg to 20 µg/kg, for example, at least 0.05, 0.7, 0.15, 0.2, 1.0, 2.0, 3.0, 4.0, 5.0, 6.0, 7.0, 8.0, 10.0, 12.0, 14.0, 16.0, or 18.0 µg/kg body weight administered weekly, every other week, or once a month. Furthermore, a therapeutically effective amount of a compound may be, for example, in the range of 100 µg/m$^2$ to 100,000 µg/m$^2$ administered every other day, once weekly, or every other week. In a desirable embodiment, the therapeutically effective amount is in the range of 1,000 µg/m$^2$ to 20,000 µg/m$^2$, for example, at least 1,000, 1,500, 4,000, or 14,000 µg/m$^2$ of the compound administered daily, every other day, twice weekly, weekly, or every other week.

The following examples are intended to illustrate, rather than limit the invention.

EXAMPLE 1

Distribution and Pharmacokinetics of Conjugates

Figure 10B:
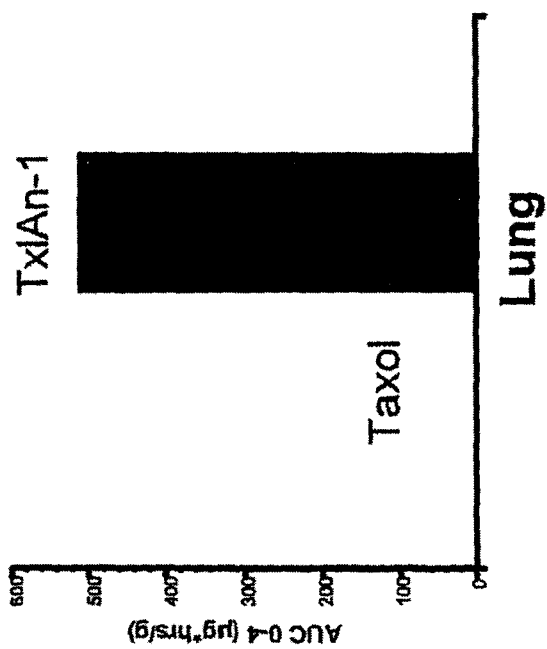
FIGS. 10A and 10B are diagrams representing tissue distribution of Taxol and TxlAn1 conjugate.
Figure 10A:
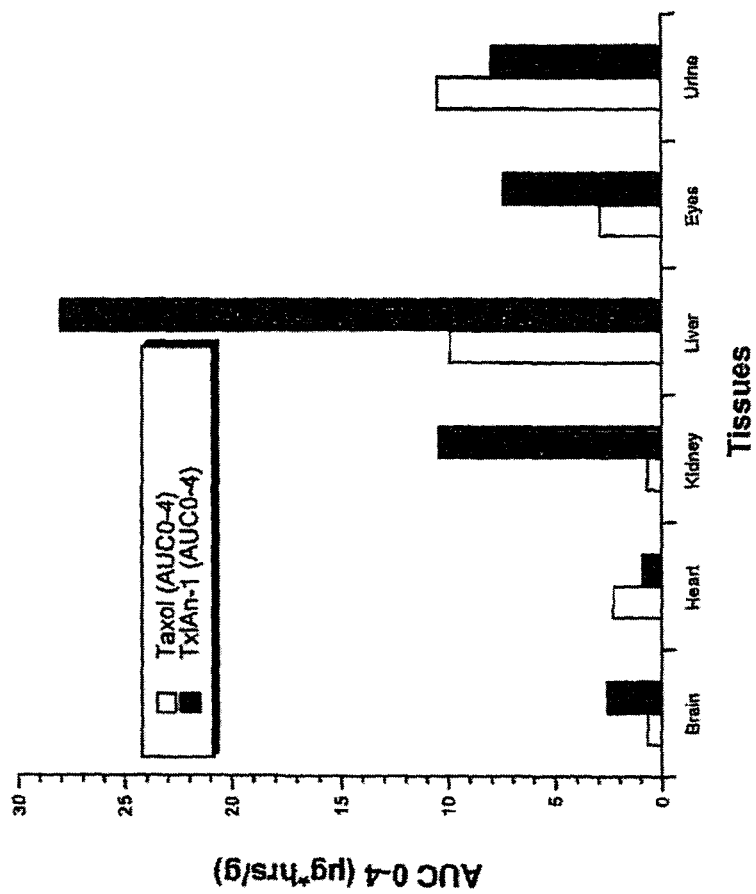

The effect of conjugation of an agent to a vector on distribution of the agent can be evaluated by administering a labeled polypeptide or conjugate to an animal and measuring distribution of the polypeptide or conjugate to organs. In one example, either $^3$H-Taxol (5 mg/kg) or $^{125}$I-Taxol-Angiopep-1 (TxlAn-1) (10 mg/kg, equivalent to 5 mg Taxol/kg) to mice. Similar experiments can be performed with any of Angiopep-3, Angiopep-4a, Angiopep-4b, Angiopep-5, Angiopep-6, and Angiopep-7. Here the unconjugated anticancer agent and the conjugates are injected intravenously to mice as a bolus. Tissues are collected at different times (0.25, 0.5, 1, and 4 hrs) and homogenized. To quantify the amount of $^3$H-Taxol, tissue homogenates are digested with tissue solubilizer, and 10 ml of liquid scintiliator was added to samples. The amount of the $^{125}$I labeled conjugate, in the different tissues is measured after TCA precipitation. Radioactivity associated with the tissues is quantified. The area under the curve (AUC 0-4) is estimated using the Prism software and is plotted for the different tissues. Using an Angiopep-1 conjugate, the AUC 0-4 values obtained for the conjugate are higher than that of Taxol in various tissues including the brain, kidney, liver, and the eyes (FIG. 10A) indicating a higher accumulation of the conjugate in these tissues compared to the unconjugated agent. The accumulation of the conjugate is much higher than unconjugated agent in the lung (FIG. 10B).

Results of a similar experiment conducted with the Taxol-Angiopep-2 conjugate are summarized in Table 4 below. Although there is difference with results obtained for the TxlAn-1 conjugate, the conjugate of Table 4 also accumulates in the lungs, brain, and liver more efficiently than unconjugated Taxol.

TABLE 4

| | AUC 0-4 (µg/g of tissue) | | |
|---|---|---|---|
| Tissue | TxlAn-2 | Taxol | Ratio (TxlAn-2/Taxol) |
| Plasma | 170 | 2.2 | 77.3 |
| Brain | 0.32 | 0.07 | 4.6 |
| Lung | 3.4 | 1.1 | 3.0 |
| Kidney | 11.2 | 8.0 | 1.4 |
| Heart | 5.0 | 2.5 | 2.0 |
| Liver | 513 | 22 | 23 |
| Eye | 0.99 | 0.57 | 1.7 |
| Urine | 35.7 | 88 | 0.4 |

Treatments equivalent to 5 mg/kg of Taxol

Figure 11:
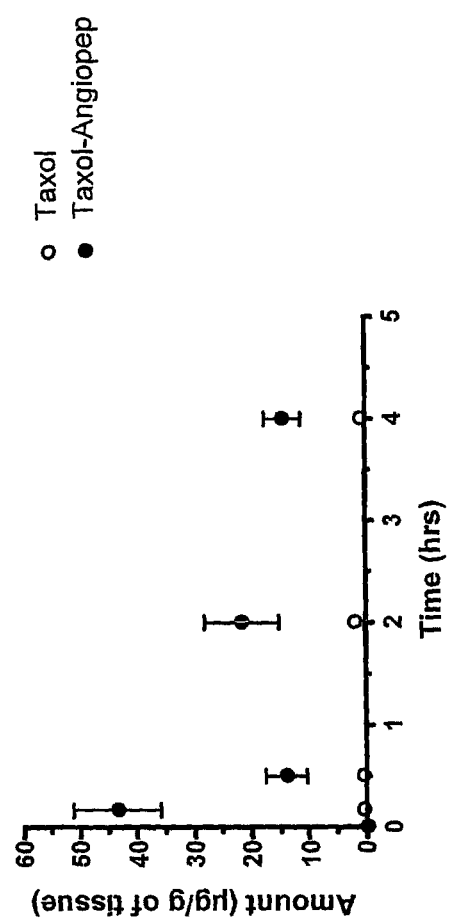
FIG. 11 is a diagram representing lung distribution of Taxol and TxlAn1.
Figure 12:
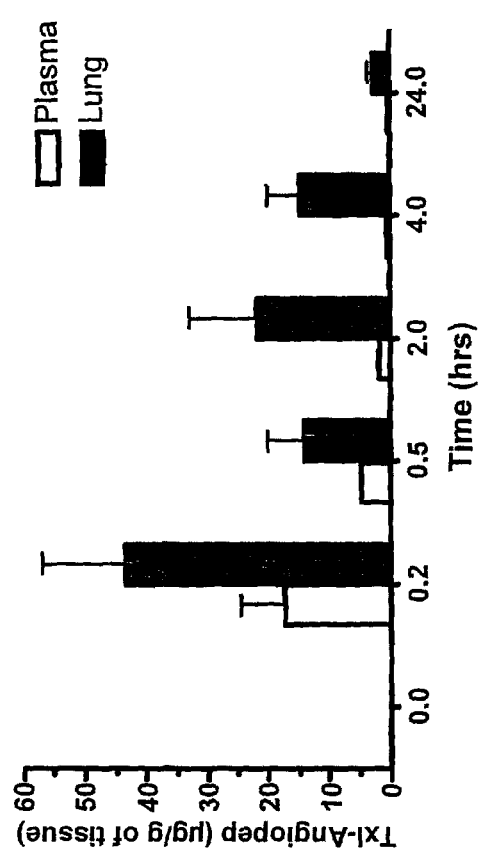
FIG. 12 is a diagram representing the levels of TxlAn1 conjugate in plasma and lung.

The kinetics of Taxol and Taxol-Angiopep-1 accumulation in the lung were studied (FIG. 11). The amount of the conjugate measured in the lungs at different times is much higher than for the unconjugated agent. Accumulation of the conjugate in the lung is also much higher than its concentration in the serum (plasma) at various times (FIG. 12). These results indicate that biodistribution or pharmacokinetics of an anticancer agent such as Taxol can be altered by conjugation to a vector of the invention (e.g., Angiopep-1 or 2).

EXAMPLE 2

Angiopep-7 is Not Efficiently Transported to the Brain

Figure 13B:
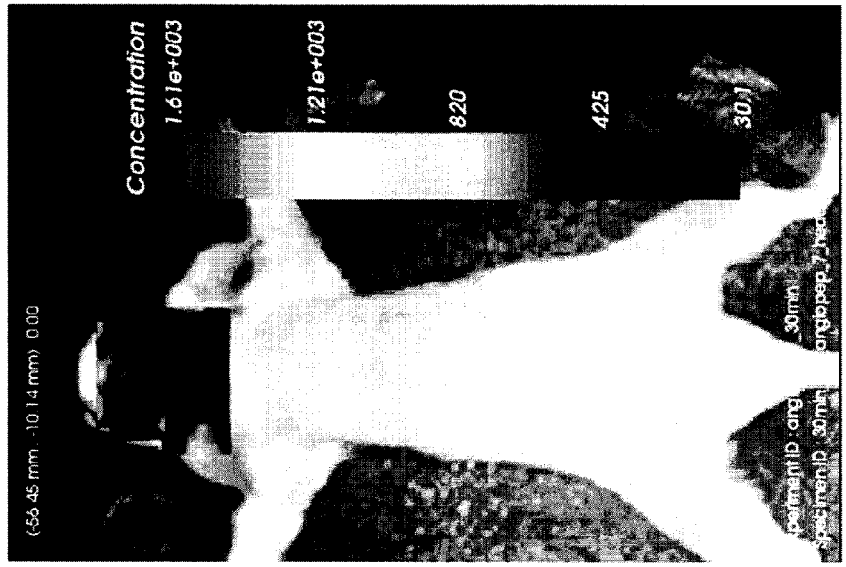
FIG. 13 is a set of images showing in vivo accumulation of Angiopep-2 and Angiopep-7 in the brains of rats 30 minutes following IV injection. Angiopep-2 accumulates to a greater extent in the brain as compared to Angiopep-7.
Figure 13A:
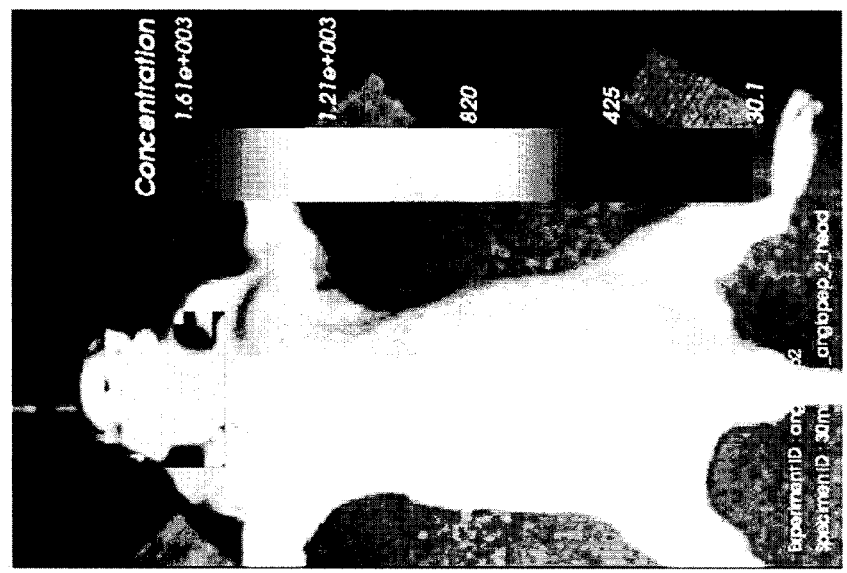

Angiopep-7 is not efficiently transported across the blood-brain barrier. Measuring accumulation of Angiopep-2 and Angiopep-7 in the brain of rats 30 minutes following IV injection, Angiopep-7 was present in the brain at lower levels than either Angiopep-1 or Angiopep-2 (FIG. 13).

Figure 14:
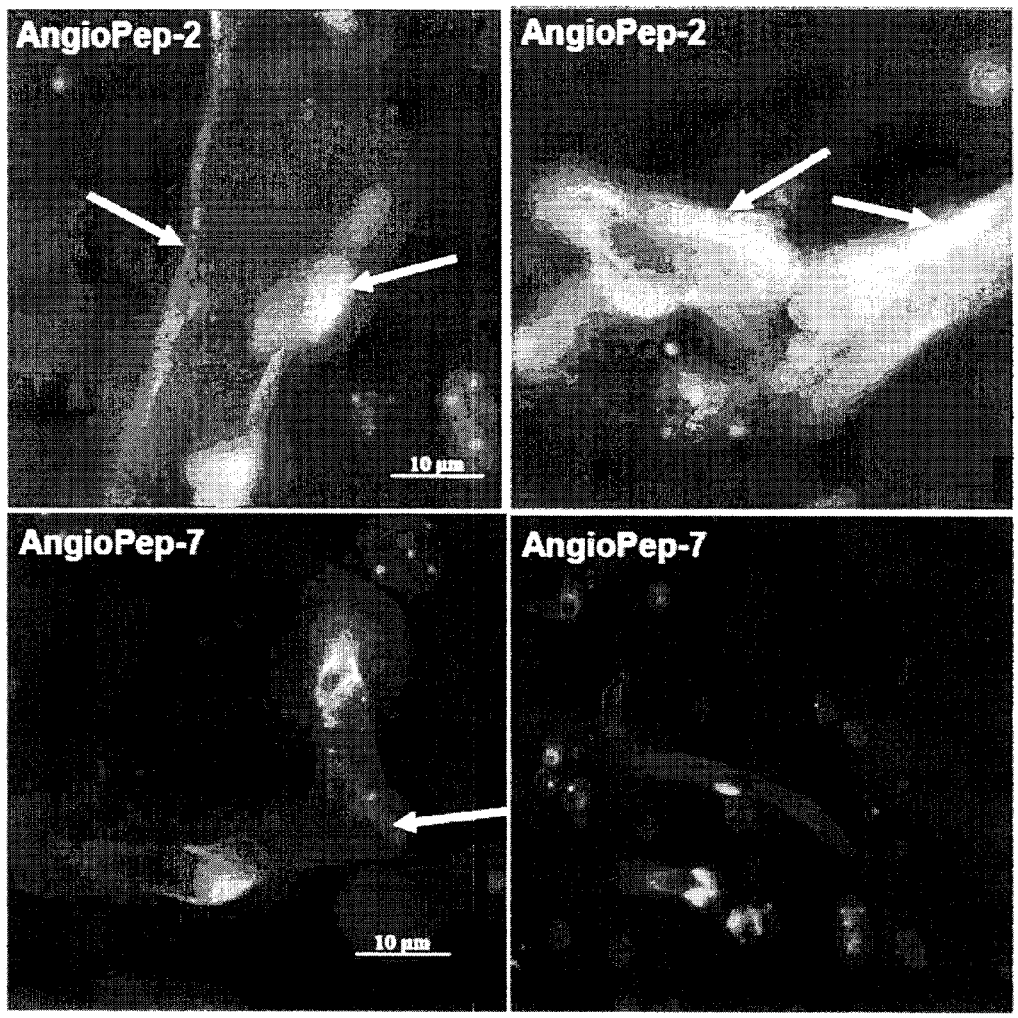
FIG. 14 is a set of images showing fluorescence microscopy of brain sections following a 10 min in situ perfusion of either fluorescently labeled Angiopep-2 or Angiopep-7. These images show that Angiopep-2 is localized within the brain, whereas Angiopep-7 is localized within the capillaries.

We have also examined accumulation of Angiopep-2 and Angiopep-7 in the brain using fluorescence microscopy after a 10 minute in situ brain perfusion. Here, 2 mM of Angiopep-2 or Angiopep-7, each conjugated to the Cy5.5 fluorescent marker, were injected into the carotid artery. The brains of the animals were then evaluated by fluorescence microscopy. In each case, the capillaries were stained with Vessel Green (FITC-lectin), the nuclei of brain cells were stained with DAPI (blue), and the Angiopeps were visualized using the Cy5.5 label (FIG. 14). From these sections, Angiopep-2 is observed to be localized within the brain, whereas Angiopep-7 is observed to be localized within the capillaries. Lower brain accumulation of Angiopep-7 as compared to Angiopep-2 is also observed in vivo. Each of Angiopep-2 and Angiopep-7 were conjugated to Cy5.5 and administered to rats. After 30 minutes, accumulation in the brain was measured using the fluorescence of the Cy5.5 indicator. On this basis, we conclude that Angiopep-7 is not efficiently transported across the BBB, whereas Angiopep-2 is transported across the BBB efficiently.

EXAMPLE 3

Angiopep-7 is Efficiently Transported to Liver, Kidney Lungs, Spleen, and Muscle Using rats administered Angiopep-2 or Angiopep-7 conjugated to Cy5.5 as described in Example 2, the levels of Angiopep-7 and Angiopep-2 were measured in organs such as liver, kidney, and lung. In these organs, similar levels of polypeptide were observed with Angiopep-7 as compared to Angiopep-2. In view of these results, we believe that Angiopep-7 may be especially useful for delivery of agent to the liver, kidney, and lungs in applications where delivery to the brain is not desired.

Figure 15B:
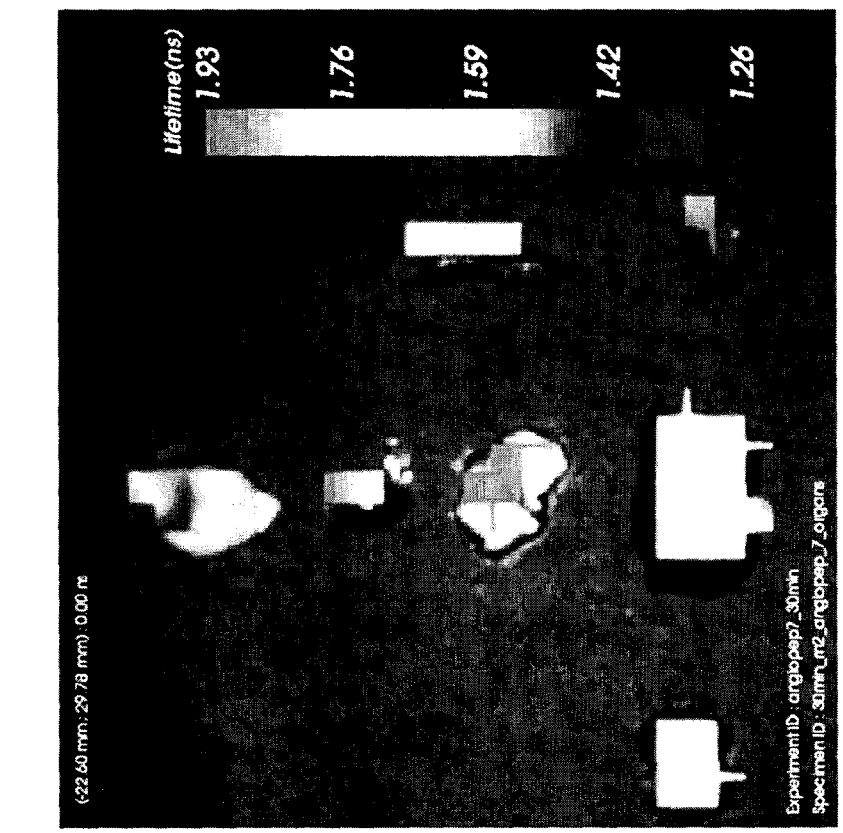
FIG. 15B is a graph showing ex-vivo organ imaging 24 hours following injection of either Angiopep-2 or Angiopep-7 in a rat. Both polypeptides accumulate in the kidneys, liver, and lungs. Angiopep-2 accumulates to a greater degree in the brain as compared to Angiopep-7.
Figure 15A:
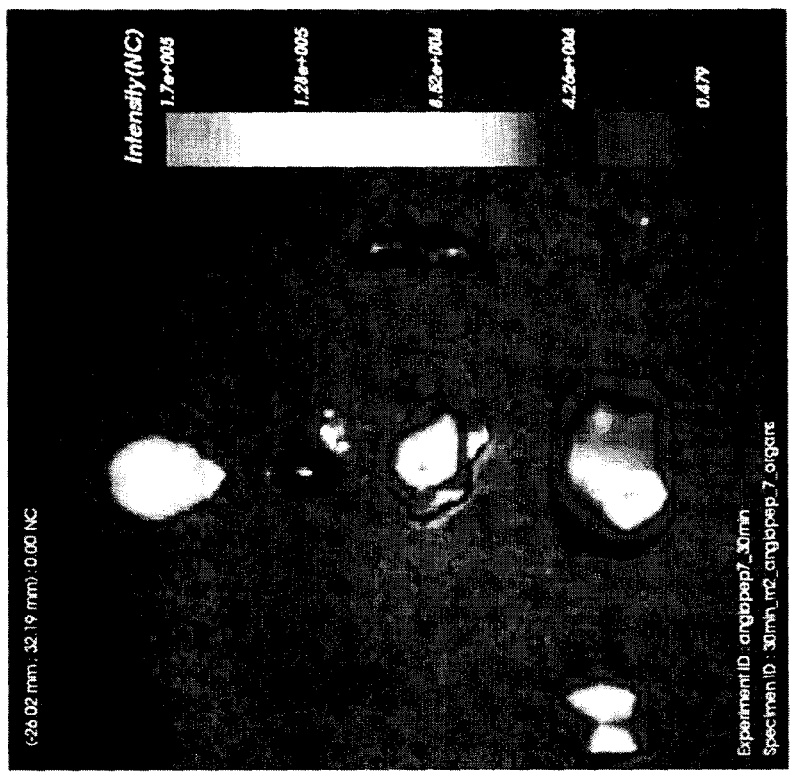
FIG. 15A is a set of images showing in vivo imaging of Angiopep-7 in the liver, lungs, and kidneys of a rat. Angiopep-7 is observed to accumulate in these tissues.

To measure Angiopep-7 concentrations in animals, imaging studies of Angiopep-7 conjugated to Cy5.5 have been performed. Based on in vivo imaging studies 30 minutes following injection, accumulation of the Cy5.5 signal was observed in the kidneys, the liver, and the lungs (FIG. 15A). Ex vivo organ analysis 24 hours after injection of Angiopep-7 was performed, and compared to injection using Angiopep-2. These studies also revealed significant accumulation of both Angiopep-2 and Angiopep-7 in the liver, lungs, and kidneys. However, Angiopep-7 showed significant less brain accumulation as compared to Angiopep-2 (FIG. 15B). Based on these results, we believe Angiopep-7 is useful as a vector for agents into peripheral organs such as the liver, kidney, lungs, spleen, or muscle in applications where delivery to the brain is not desired.

EXAMPLE 4

Transport of IgG Conjugates

Brain uptake of these vectors was measured using the in situ brain perfusion experimental model. Results (shown in Table 5 below) revealed that lysines at position 10 and 15 are important in these vectors ability to cross the BBB.

TABLE 5

Brain uptake of Angiopeps measured by in situ brain perfusion

| Vector | Parenchyma (ml/100 g) | Transport relative to Angiopep-1 (250 nM), expressed as percent |
|---|---|---|
| Angiopep-1 (50 nM) | 34.9 | 155.46 |
| Angiopep-1 (250 nM) | 22.45 | 100.00 |
| Angiopep-1 (dimer) (250 nM) | 27.03 | 120.40 |
| Angiopep-2 (250 nM) | 19.62 | 87.39 |
| Angiopep-3 (250 nM) | 17.08 | 76.08 |
| Angiopep-4a (250 nM) | 17.57 | 78.26 |
| Angiopep-4b (250 nM) | 12.05 | 53.67 |
| Angiopep-5 (250 nM) | 11.82 | 52.65 |
| Angiopep-6 (250 nM) | 8.64 | 38.49 |
| Angiopep-7 (250 nM) | 2.99 | 13.32 |

Figure 16:
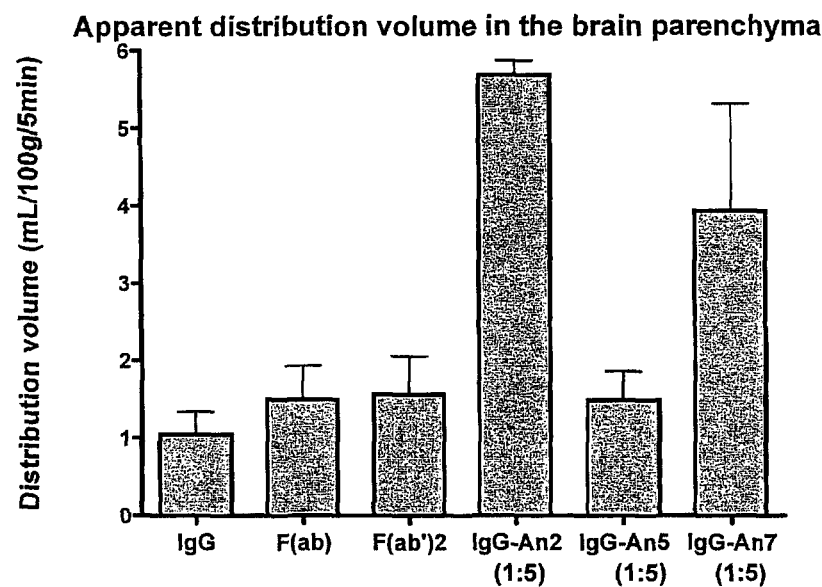
FIG. 16 illustrates the distribution volume in the brain parenchyma of free and Angiopeps conjugated IgG.

The Angiopep polypeptides were conjugated to IgG using the SATA cross-linker and their transport capacity was studied using in situ brain perfusion. As shown in FIG. 16, Angiopep-2 is the most highly distributed conjugate in brain parenchyma. It also appears that polypeptide dimers are efficiently transported. Angiopep-7 was not efficiently transported into the brain.

EXAMPLE 5

Effect of Conjugates on Cell Growth In Vitro

Figure 17:
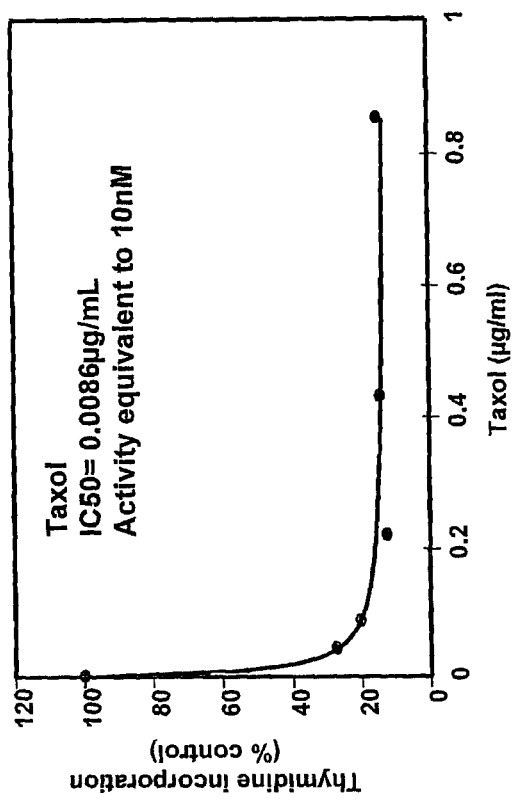
FIG. 17 is a diagram of cell proliferation in the presence of the parent drug Taxol. Glioblastoma cells (U-87) were exposed to various concentrations of Taxol for 3-days. $^3$H-Thymidine incorporated in cells were plotted as a function of Taxol concentrations.

To test for the ability of conjugates including a vector and an anticancer agent to kill cancer cells, in vitro can be performed. In one example, Taxol (unconjugated) is shown to block the proliferation of gliobiastoma cells (U-87) with IC50 value of around 10 nM (FIG. 17). The effect of Taxol conjugated when conjugated a vector described herein is evaluated and compared to unconjugated Taxol. As shown in Table 6A, the IC50 values obtained for the Taxol-Angiopep-2 (TxlAn2) conjugate were very similar to that of unconjugated Taxol in many cancer cells. Endothelial cells from rat brain (RBE4) were less sensitive than the tested cancer cell lines. For comparison purposes, results obtained were expressed in term of Taxol concentration.

Most of theses cells (U-87, U-118, NC1-H460, A549) express LRP. This data is however unavailable for RBE4 cells. The anti-proliferation activity of the conjugate against cancer cells in vitro is assessed. In this assay, cancer cells (U87 and U118) are exposed for 48 hrs to an anticancer agent (e.g., Taxol) and conjugate (e.g., TxlAn2 (3:1) conjugate. Incorporation of [$^3$H]-thymidine in U87 and U118 cells decreases as a function of the concentration of the agent. The values required to inhibit cell proliferation by 50% (1C50) are expressed. Results obtained from the proliferation assays indicate that the IC50 values required for the inhibition of cancer cell proliferation are expressed in nM and demonstrate that TxlAn2 (3:1) conjugate is 3 times more potent than paclitaxel, and are in the same range when reported in paclitaxel equivalent (Table 6B). Similar experiments can be performed using any of the vectors or conjugates described herein.

The capacity of a conjugate (e.g., TxlAn2 (3:1)) to block the proliferation of other cancer cell types is also estimated. Such assays can be performed in lung cancer cells (NC1-

H460)as well as the breast cancer cell line (MDA-MB231, MDA-MB-468, HCC-1954, BT-474) in hepatocarcinomas (SK-Hep1) and glioblastomas (U-87MG). We have shown that such cells are also very sensitive to TxlAn2 (3:1) conjugate (Table 6B).

TABLE 6A

Effect of conjugate on cell proliferation.

| | IC50 (nM) | |
|---|---|---|
| Cell lines | Taxol | Taxol-Angiopep-2 (3:1) |
| Glioblastomas | | |
| U-87 | 9.5 | 9.7 |
| U-118 | 7.2 | 8.1 |
| Lung carcinoma | | |
| NCI-H460 | 9.3 | 12.5 |
| A549 | 3.6 | 6.0 |
| Calu-3 | 17.2 | 25.0 |
| Endothelial cells | | |
| RBE4 | 137 | 139 |

TABLE 6B

In vitro cytotoxicity of Taxol and TxlAn2 (3:1) conjugate

| | Paclitaxel | | | | TxlAn2 (3:1) conjugate | | | |
|---|---|---|---|---|---|---|---|---|
| | IC50 (nM) | | Residual survival % | | IC50 (nM) | | Residual survival % | |
| Cell line | Mean | SD | Mean | SD | Mean | SD | Mean | SD |
| BT-474 | 62.86 | — | 52.24 | 3.87 | 40.22 | — | 51.83 | 1.70 |
| HCC1954 | 6.12 | — | 48.82 | 11.17 | 8.26 | 3.37 | 44.08 | 8.63 |
| MDA-MB-231 | 17.61 | — | 45.62 | 13.89 | 28.16 | — | 46.95 | 7.50 |
| MDA-MB-468 | 13.52 | — | 54.26 | 10.34 | 1.41 | — | 55.34 | 5.55 |
| NCI-H460 | 6.61 | 3.35 | 24.98 | 10.80 | 12.68 | 10.08 | 30.44 | 9.36 |
| SK-HEP-1 | 8.84 | — | 55.18 | 13.17 | 7.83 | — | 54.09 | 11.03 |
| U-87 MG | 12.94 | 2.49 | 40.35 | 2.40 | 17.75 | 10.82 | 44.13 | 1.85 |

EXAMPLE 6

Inhibition of Tumor Growth In Vivo (U-87)

Figure 18A:
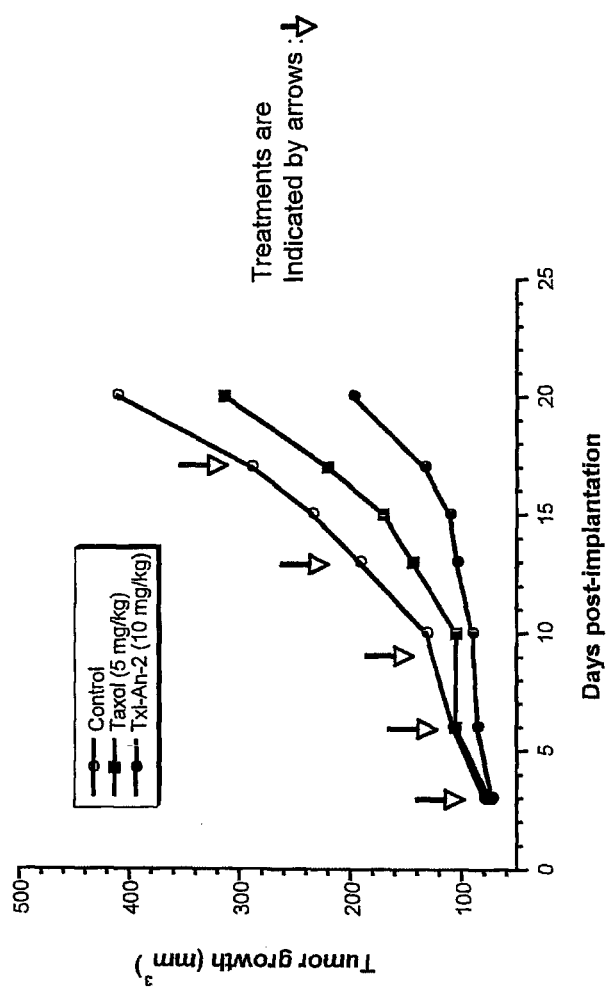
FIGS. 18A and 18B are graphs representing the effect of TxlAn2 treatment on subcutaneous glioblastomas (U-87) tumor growth.

The ability of a conjugate to inhibit tumor growth can be evaluated in an in vivo model (see, e.g., FIG. 18A). U-87 cells are subcutaneously implanted in the right flank of mice and, on day 3 post-implantation, mice are injected with the vehicle (DMSO/Ringer:80/20; control), an unconjugated agent (e.g., Taxol (5 mg/kg)) or the agent as part of a conjugate (e.g., Taxol-Angiopep-2 (10 mg/kg) equivalent to 5 mg Taxol/kg. Tumor growth inhibition is more pronounced in mice treated with the conjugate than in mice treated with the unconjugated anticancer agent.

In one example, at day 17 post-implantation, tumor growth was inhibited by more than 75% using the TxlAn2, whereas tumor growth was inhibited by 34% using the unconjugated agent (Table 7). Thus, the conjugates are more efficient than unconjugated agents at inhibiting tumor growth in vivo. Overall, a 2.2-fold tumor growth inhibition level was measured for the conjugate compared to the unconjugated agent.

TABLE 7

Inhibition of tumor growth with conjugates.

| | Tumor volume (mm$^3$) (mean ± sem) Days post-injection | | Tumor growth | Inhibition | T/C |
|---|---|---|---|---|---|
| Groups | Day 0* | Day 14** | Δ (mm$^3$) | (%) | (%) |
| Control | 79 ± 7 | 289 ± 50 | 203 ± 47 | | 100 |
| Taxol (5 mg/kg) | 74 ± 5 | 219 ± 52 | 134 ± 55 | 34 | 66 |
| TxlAn2 (3:1) (10 mg/kg) | 88 ± 9 | 144 ± 27 | 56 ± 32 | 73 | 27 |

Treatment equivalent to 5 mg/kg of Taxol
*corresponds to 3 days post-implantation (first treatment)
**corresponds to 17 days post-implantation (after 4 treatments)

EXAMPLE 7

Inhibition of Tumor Growth In Vivo (Hepatocarcinoma)

In vivo studies are conducted to determine whether a conjugate can inhibit the growth of hepatocarcinoma cells (SK-Hep 1) implanted subcutaneously. Nude mice receive a subcutaneous injection of 2.5×10$^6$ human SK-Hep 1 cells in their right flank. Treatments are started when the size of the implanted tumor reached approximately 200 mm$^3$. Animals receive treatment with a conjugate or vehicle by intraperitoneal injections.

Figure 18B:
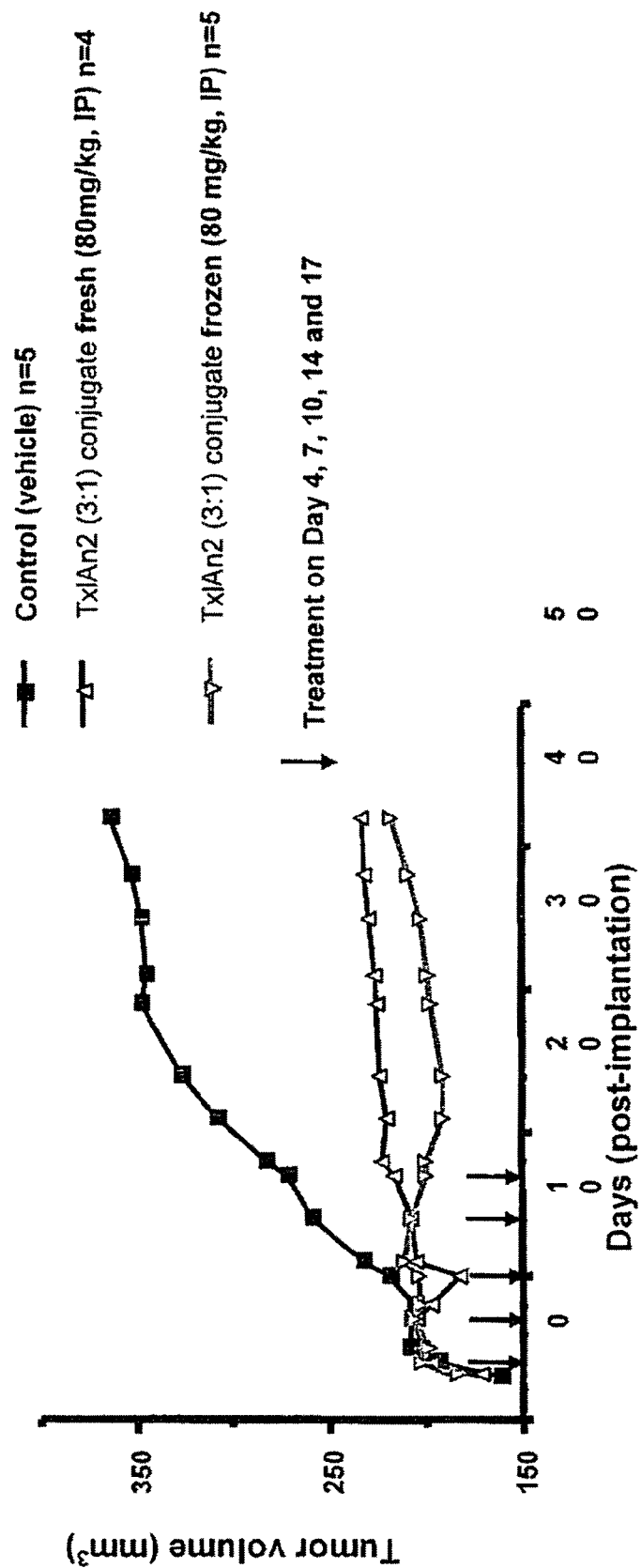

Results from an experiment performed with a TxlAn2 (3:1) administered at 80 mg/kg by intraperitoneal injection are shown in FIG. 18B; treatments are indicated by black arrows. In this experiment, treatments were given twice a week for five treatments maximum at the dose indicated of 80 mg/kg. TxlAn2 (3:1) conjugate administered i.p. shows high efficacy in inhibiting the growth of hepatocarcinomas, a type of cancer usually not sensitive to Taxol® (FIG. 18B).

EXAMPLE 8

Methods for Evaluating Conjugate Activity

The following methods were used in Examples described herein.

Cell Proliferation Assay

For the in vitro cell proliferation assay, between 2.5 and 5×10$^4$ of U87 or A549 cells are seeded in a 24 well tissue culture microplate in a final volume of 1 ml of medium with 10% serum and incubated for 24 hours at 37° C. and 5% $CO_2$. The medium is then replaced with serum-free medium and incubated overnight. The next morning the agent is freshly dissolved in dimethyl sulfoxide (DMSO) and the medium is replaced with complete medium containing the agent at different concentrations in triplicates. The final concentration of DMSO is 0.1%. The control used is a microplate well with cells and without agent. The cells are incubated for 48 to 72 hrs at 37° C. and 5% $CO_2$. After the incubation, the medium is changed and replaced with 1 ml of complete medium containing [$^3$H]-thymidine (1 pCi/assay). The plate is incubated at 37° C. and 5% $CO_2$ for 4 hrs. The medium is removed, and the cells are washed with PBS at 37° C. The cells are fixed with a mix of ethanol:acetic acid (3:1), are washed with water, and precipitated 3 times with 10% of ice-cold TCA (trichloroacetic acid). Finally 500 µl of PCA (perchloric acid) is added to the wells and the microplates are heated for 30 min at 65° C. and 30 min at 75° C. The contents of each well is then transferred in a scintillation vial with 10 ml of scintillation cocktail and the activity is measured in CPM (count per minute) on a liquid scintillation counter Tri-Carb from Packard.

Iodination of Polypeptides

Polypeptides are iodinated with standard procedures using iodo-beads from Sigma. Briefly polypeptides are diluted in 0.1 M phosphate buffer, pH 6.5 (PB). Two iodo-beads are used for each protein. These beads are washed twice with 3 ml of PB on a Whatman filter and re-suspended in 60 µl of PB. $^{125}$I (1 mCi) from Amersham-Pharmacia biotech was added to the bead suspension for 5 min at room temperature. Each iodination was initiated by the addition of the polypeptide (100 µg). After an incubation of 10 min at room temperature, the free iodine was removed by HPLC.

Subcutaneous Implantation

In order to estimate the efficiency of the conjugates and formulations on tumor growth, we developed a subcutaneous model of glioblastomas. In this model, $2.5 \times 10^6$ cells in 100 µl of cell medium without serum containing 1% methylcellulose are subcutaneously injected in the mice flank. The tumor is clearly visible and can be measured using a vernier caliper. The estimated tumor volume was then plotted as a function of time.

In situ Mouse Brain Perfusion

The uptake of [$^{125}$I]-polypeptides to the luminal side of mouse brain capillaries is measured using the in situ brain perfusion method adapted in our laboratory for the study of agent uptake in the mouse brain. Briefly, the right common carotid of ketamine/xylazine (140/8 mg/kg i.p.) anesthetized mice is exposed and ligated at the level of the bifurcation of the common carotid, rostral to the occipital artery. The common carotid is then catheterized rostrally with polyethylene tubing filled with heparin (25 U/ml) and mounted on a 26-gauge needle. The syringe containing the perfusion fluid ([$^{125}$I]-polypeptides or [$^{14}$C]-inulin in Krebs/bicarbonate buffer at a pH7.4 gassed with 95% $O_2$ and 5% $CO_2$) is placed in an infusion pump (Harvard pump PHD 2000; Harvard Apparatus) and connected to the catheter. Prior to the perfusion, the contralateral blood flow contribution is eliminated by severing heart ventricles. The brain is perfused for the indicated times at a flow rate of 1.15 ml/min. After 14.5 min of perfusion, the brain is further perfused for 60 s with Krebs buffer to wash the excess of [$^{125}$I]-proteins. Mice are then decapitated to terminate perfusion and the right hemisphere is isolated on ice before being subjected to capillary depletion. Aliquots of homogenates, supernatants, pellets and perfusates are taken to measure their contents in [$^{125}$I]-conjugates by TCA precipitation and to evaluate the apparent volume of distribution.

EXAMPLE 9

Mechanism of Action of Conjugates

Figure 19:
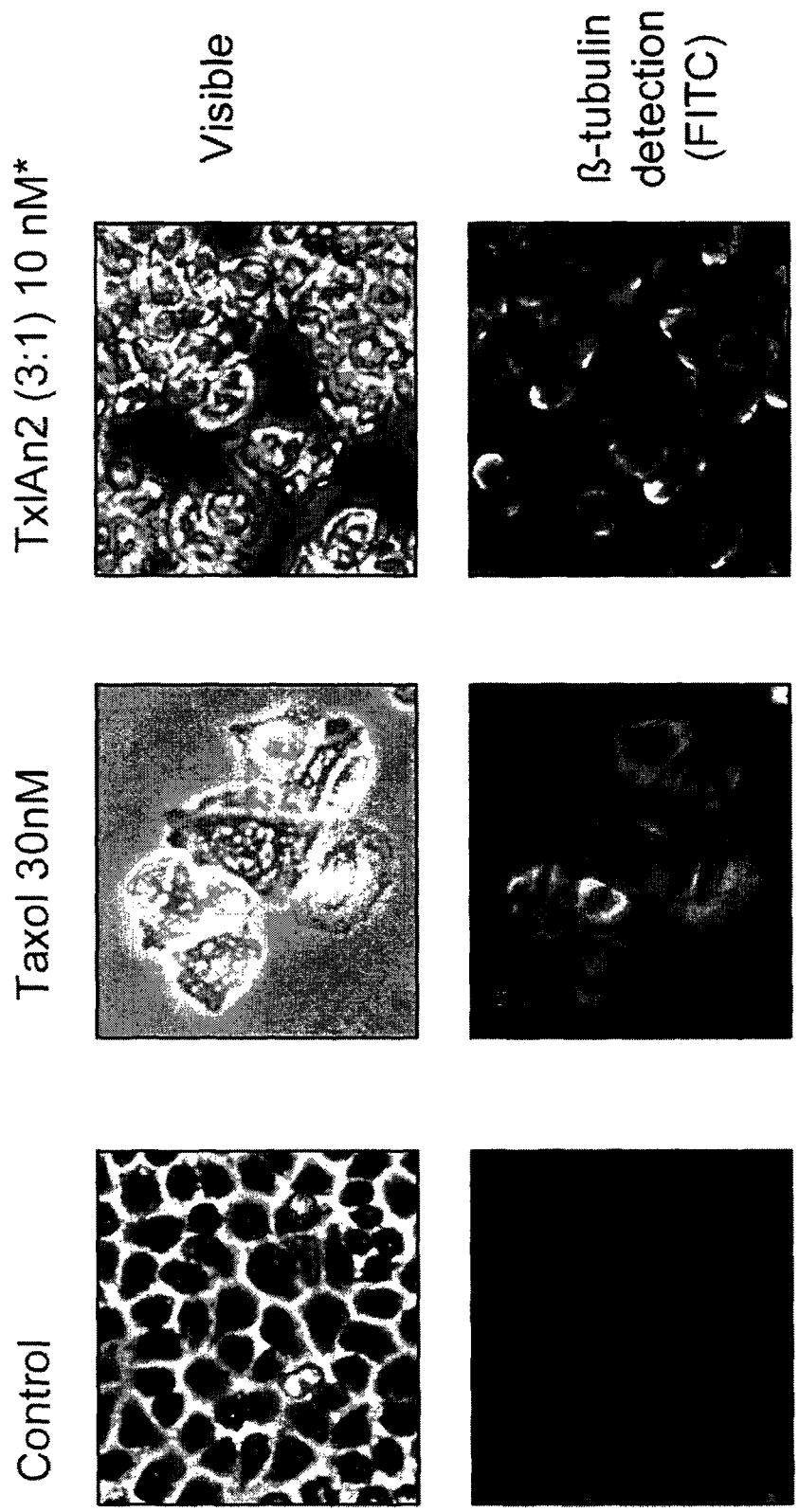
FIG. 19 is a set of photomicrographs showing detection of β-tubulin in NCI-H460 cells by immunofluoresence or visible light in cancer cells exposed to Taxol or TxlAn2 conjugate. As a control, cells were exposed to 1% DMSO.
Figure 21A:
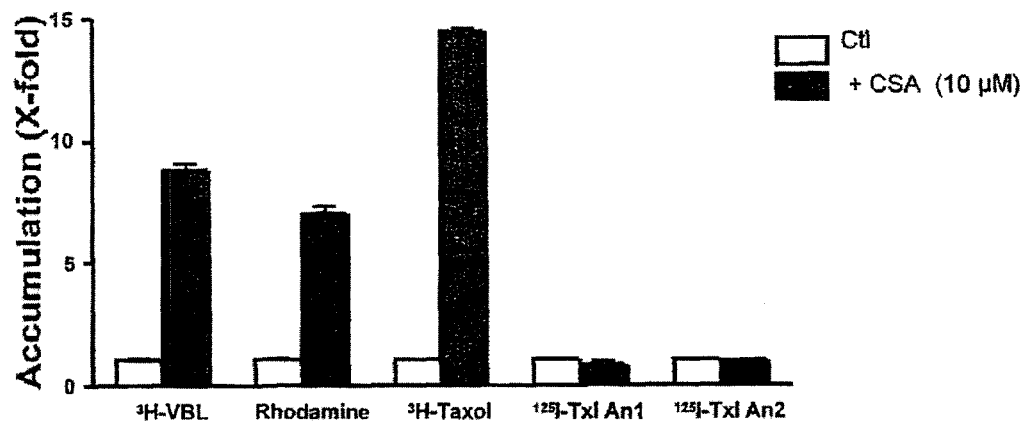
FIG. 21A is a graph showing accumulation of various drugs in MDCK cells transfected with MDR1 in the presence or absence (control) of 10 μM CsA, a P-gp inhibitor. The experiment was performed in the presence of 1% DMSO.
Figure 21B:
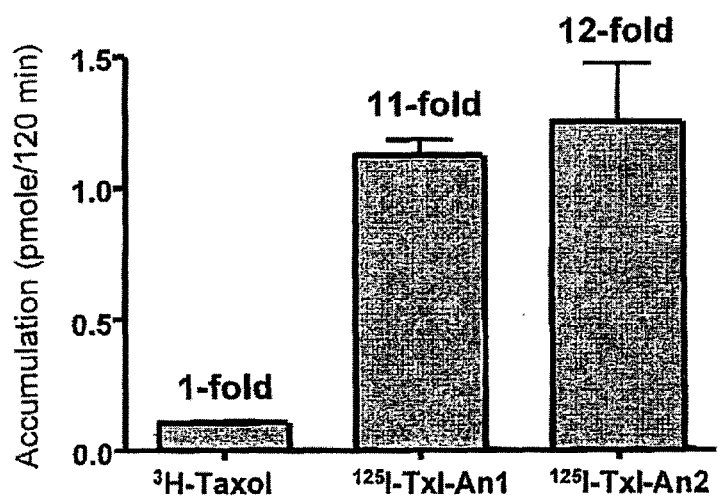
FIG. 21B is a graph showing accumulation of the conjugate in cells over-expressing P-gp.

Mechanism of action studies of conjugated therapeutic agents may also be performed. In one example, lung cancer cells (NCI-H460) are incubated for 24 hrs with either free Taxol (30 nM) or a Taxol conjugate (e.g., TxlAn2 10 nM; equivalent to 30 nM of Taxol; FIG. 19)). After cells are labeled for β-tubulin using a secondary antibody linked to FITC, pictures are taken in visible and fluorescence modes. In this example, both Taxol and the Taxol conjugate have similar effects on β-tubulin leading to its polymerization. As exemplified in FIG. 20, the addition of Taxol and the Taxol conjugate induce a blockade of NCI-H460 cell in G2/M phase. These results suggest that TxlAn conjugate has a similar mechanism of action on cancer cells than Taxol.

EXAMPLE 10

Preparation of Conjugates

Figure 23A:
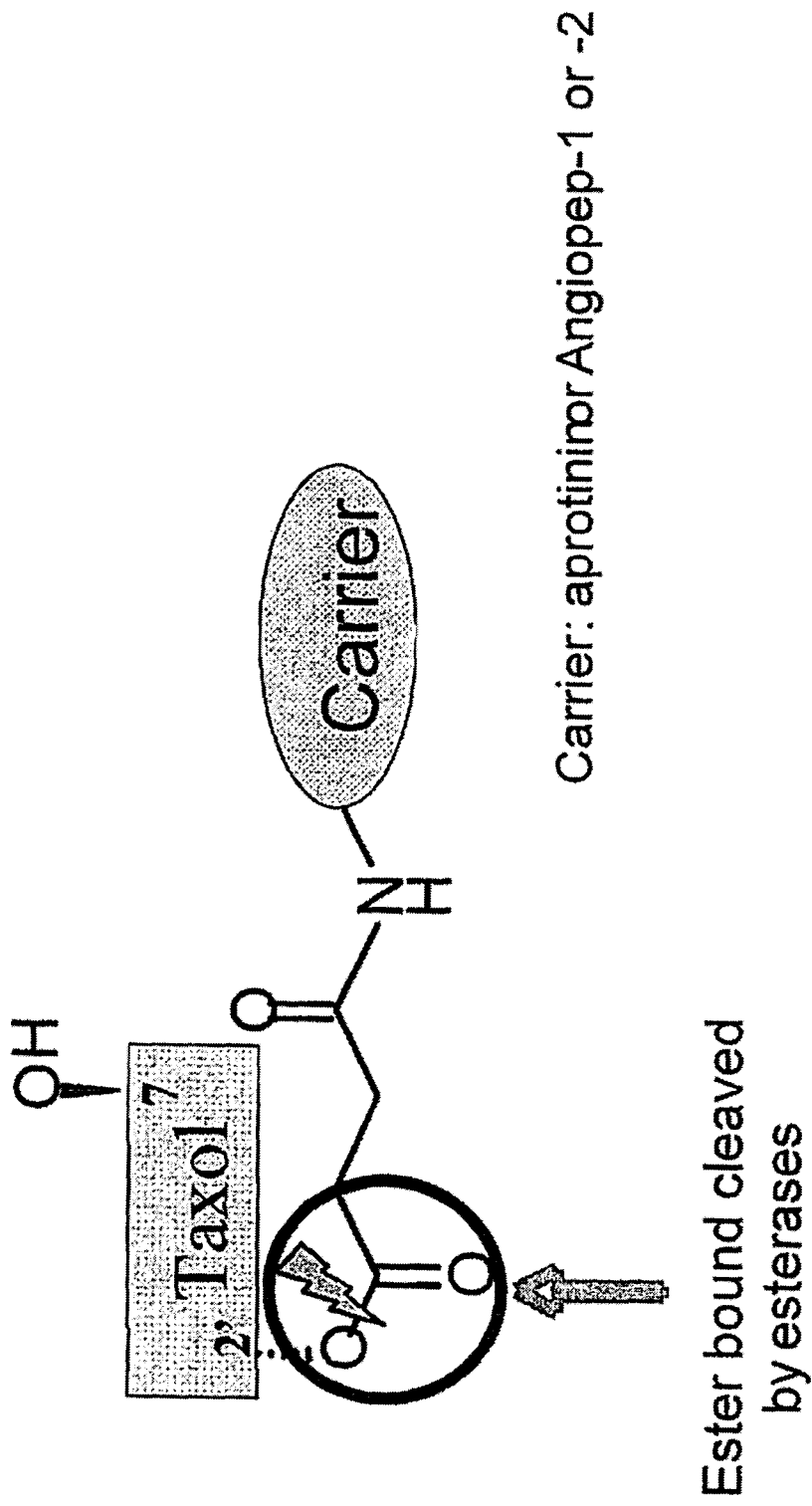
FIGS. 23A and 23B are a schematic representation of conjugation of a drug to the vector of the invention.
Figure 23B:
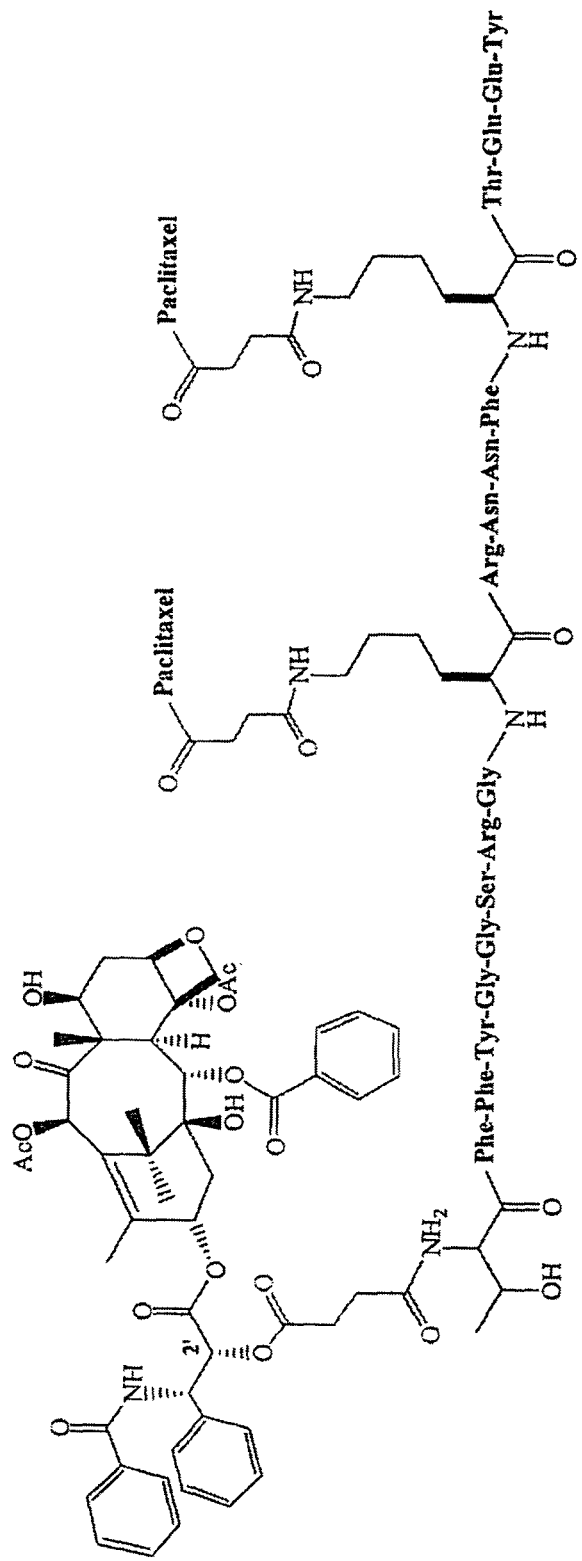

Conjugation of an agent to a vector described herein is exemplified in FIGS. 23A-23B. In this example, Taxol is first activated into an N-succinimide (2'-NHS-Txl) derivative. The amines found, for example, in a vector (e.g., amino-terminal amine or lysine residues) are reacted on the activated Taxol to form a peptide bond (amide bond). If multiple amine are available, this reaction produces multiple combinations of conjugates, e.g., with the addition of 1, 2 or 3 Taxols to the polypeptide, depending on the molar ratio used. The conjugation products are analyzed by HPLC, and conjugation is confirmed by Mass spectroscopy (Maldi-Tof). Taxol is found to be releasable from the vector by cleavage of the ester bond with an esterase.

Figure 24:
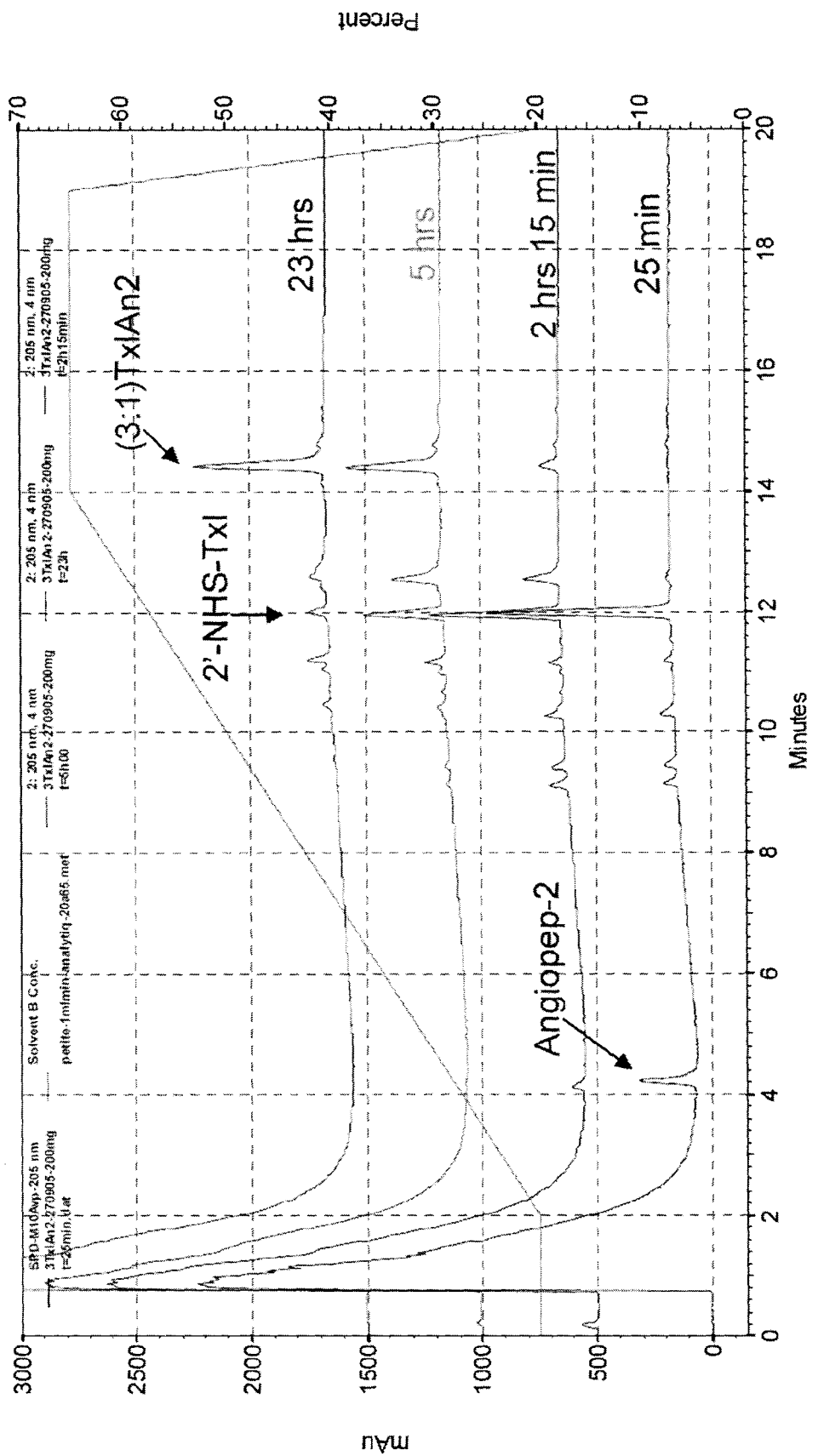
FIG. 24 is a chromatogram illustrating production of the TxlAn2 (3:1) conjugate.

Any vector described herein can be conjugated to an agent using this method. The production of the TxlAn2 (3:1) conjugate was carried out by directly adding 1 mole equivalent of Angiopep-2 to a solution of 2.5 moles equivalent of 2'-NHS-Taxol. The reaction was performed in 68% DMSO in Ringer solution (pH 7.3) for 1 hr at 12° C. After removing the cold bath, the reaction was allowed to continue for about 22 hrs at room temperature (FIG. 24). Angiopep-2, 2'-NHS-Taxol and TxlAn2 (3:1) conjugate are shown on the chromatogram by arrows. Aliquots of the reaction were sampled and analyzed by HPLC after 25 min, 2 hrs 15 min, 5 hrs and 23 hrs as indicated in FIG. 24 The peaks of Angiopep-2, 2'-NHS-Taxol and TxlAn2 (3:1) conjugate are shown by arrows on the chromatogram. Results of FIG. 24 illustrate the disappearance of Angiopep-2 and 2'-NHS-Taxol during the reaction mainly to the profit of the TxlAn2 (3:1) conjugate.

Figure 25:
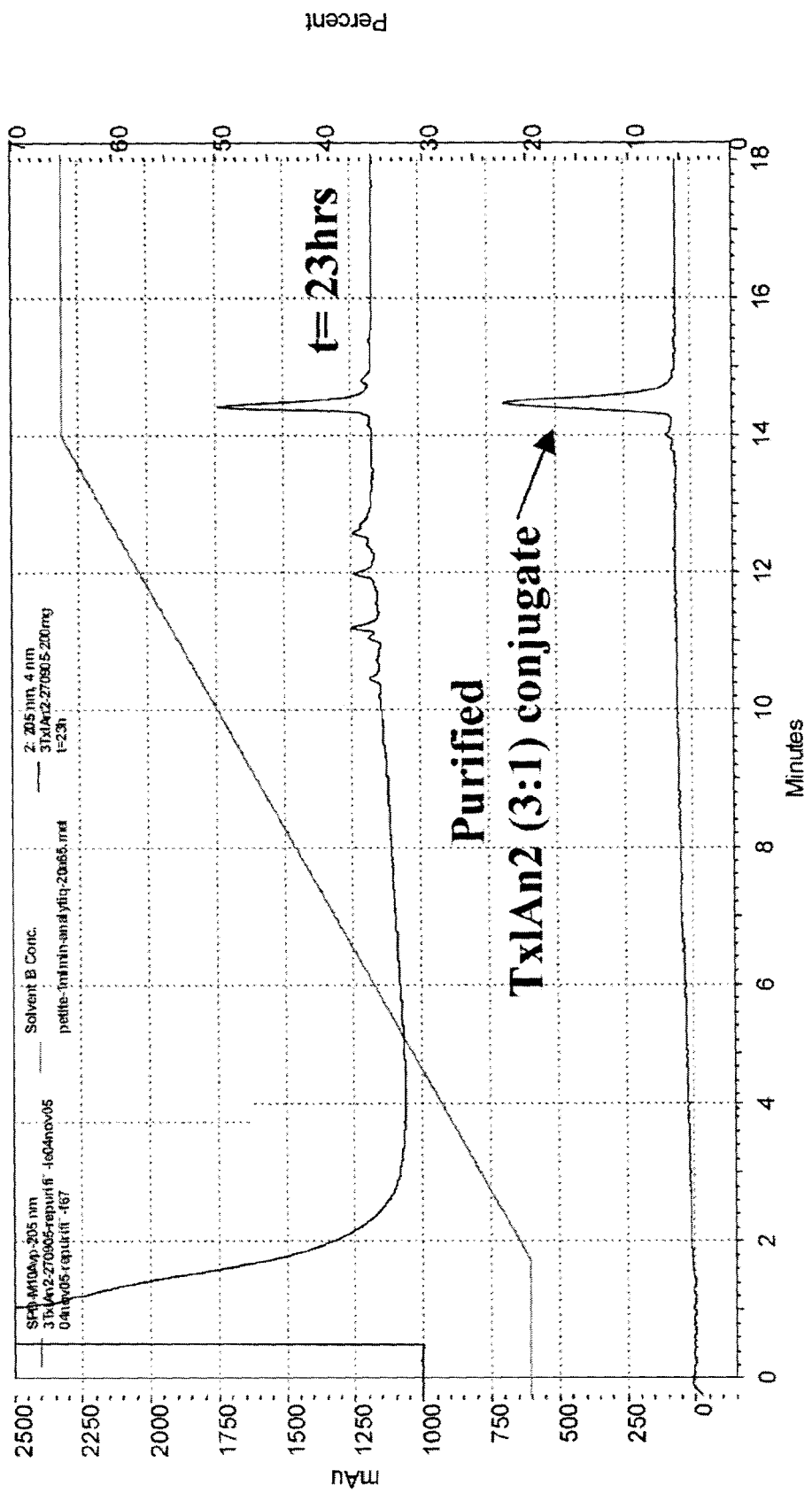
FIG. 25 is a HPLC analysis of the peak purified on a hydrophobic column using AKTA-explorer.

This mixture of products was separated by hydrophobic chromatography on a RPC 300 mm column with a flow rate at 4 ml/min using AKTA-explorer (FIG. 25). For the peak that corresponds to the TxlAn2 (3:1) conjugate, fractions were pooled, analyzed by HPLC and MS. In FIG. 25, the upper chromatogram corresponds to the running reaction at t=23 hrs whereas the lower one corresponds to the TxlAn2 (3:1) conjugate which has been confirmed by mass spectrometry (MW 5107) after AKTA purification.

EXAMPLE 11

Antibody Conjugation and Uptake

Antibodies can be conjugated to aprotinin as described in U.S. Patent Application Publication No. 2006/0189515. Similar results can be obtained with any vector described herein.

Figure 26:
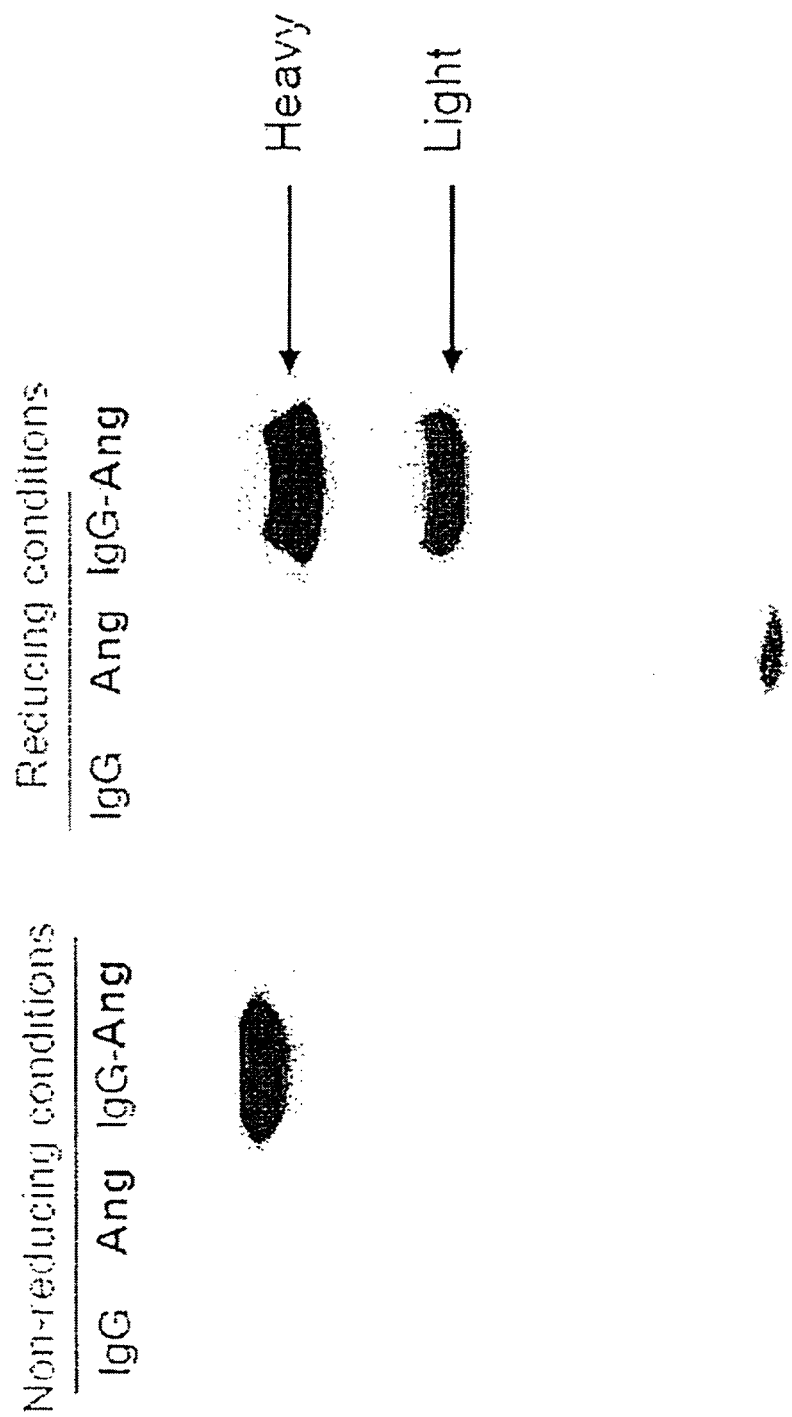
FIG. 26 illustrates the association of Angiopep-2 with the light and heavy chain of IgG.

We therefore conjugated Angiopep-2 to IgG using SATA. Following conjugation, about 3 to 5 molecules of Angiopep-2 are associated with both the light and heavy chains of IgG (FIG. 26). Therefore, using this approach, 2 to 6 molecules of vector (e.g., Angiopep-1, Angiopep-2) are expected to be conjugated for each molecule of antibody (heavy and light chains).

Figure 4:
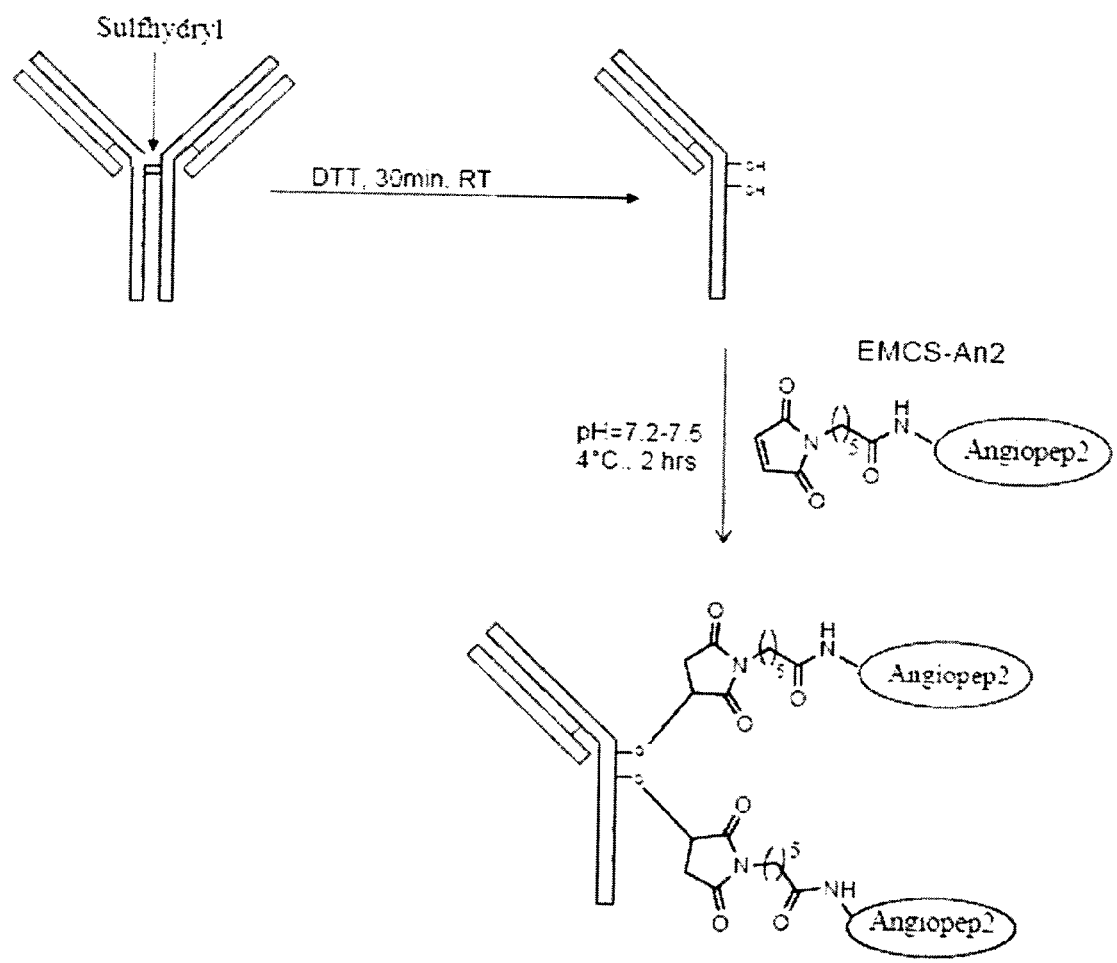
FIG. 4 illustrates the protocol used to conjugate Angiopep-2 with antibodies using cross-linker ECMS.
Figure 27:
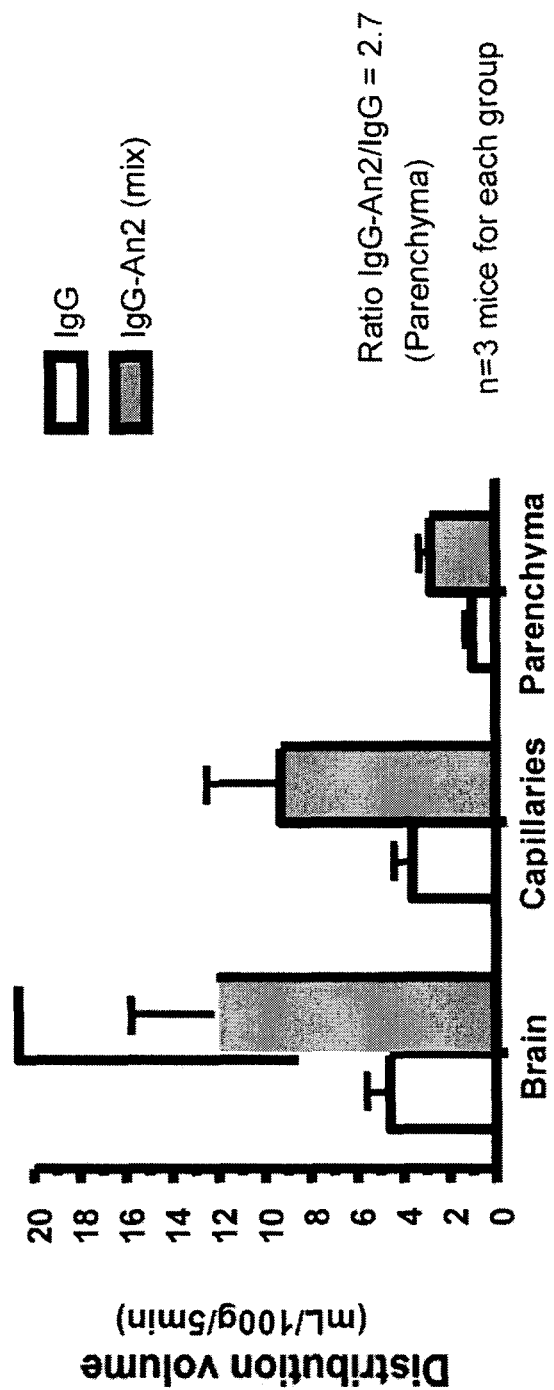
FIG. 27 illustrates increased brain distribution volume of IgG-Angiopep-2 conjugates cross-linked with sulfo-EMCS.

Conjugation of Angiopep-2 using sulfo-EMCS was also performed, as illustrated in FIG. 4. The brain distribution of IgG-Angiopep-2 conjugates coupled via sulfhydryl groups using EMCS-Angiopep-2 were tested in various brain tissues (total brain, capillaries, parenchyma). There is higher (about three fold difference) brain uptake of [$^{125}$I]-IgG-Angiopep-2 conjugate than that of unconjugated [$^{125}$I]-IgG (see FIG. 27). The conjugation of IgG with Angiopep-2 therefore increases IgG accumulation in the brain in vivo.

Figure 28:
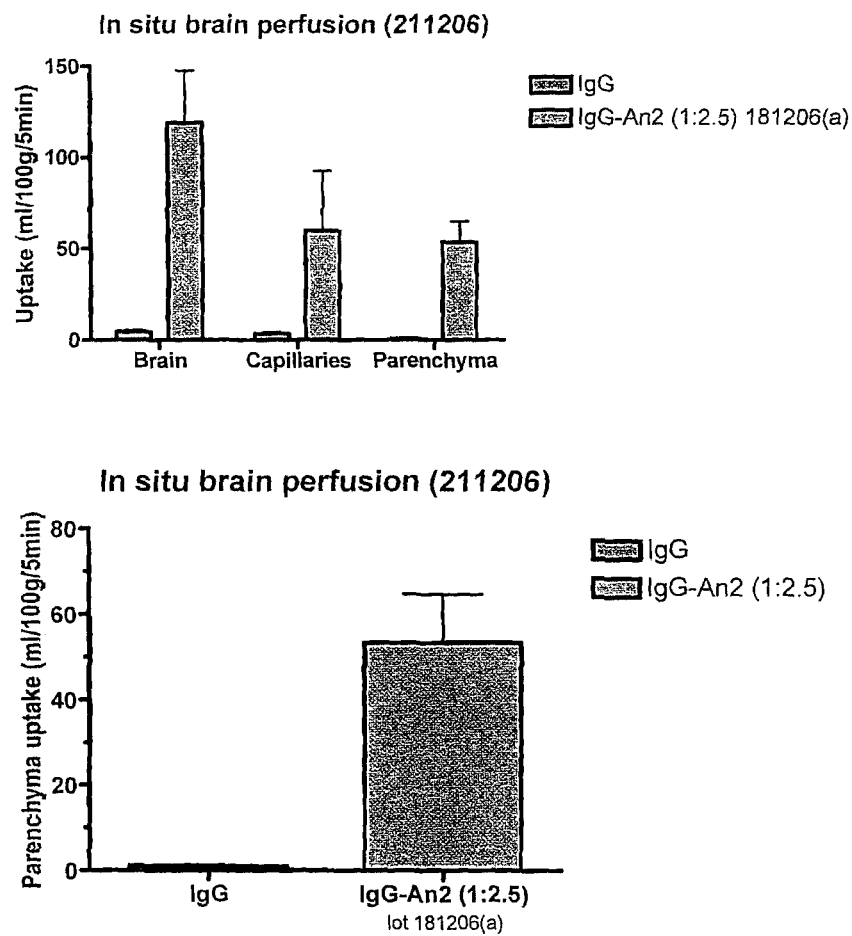
FIG. 28 illustrates the brain penetration for IgG-Angiopep-2 conjugates using in situ brain perfusion.

The transport of Angiopep-2-IgG conjugates coupled using the SATA method was also tested using in situ brain perfusion experiments. IgG-An2 conjugates are transported into brain tissues (FIG. 28). IgG-Angiopep-2 conjugates accumulated in the parenchyma about 50 times greater than IgG.

Figure 29:
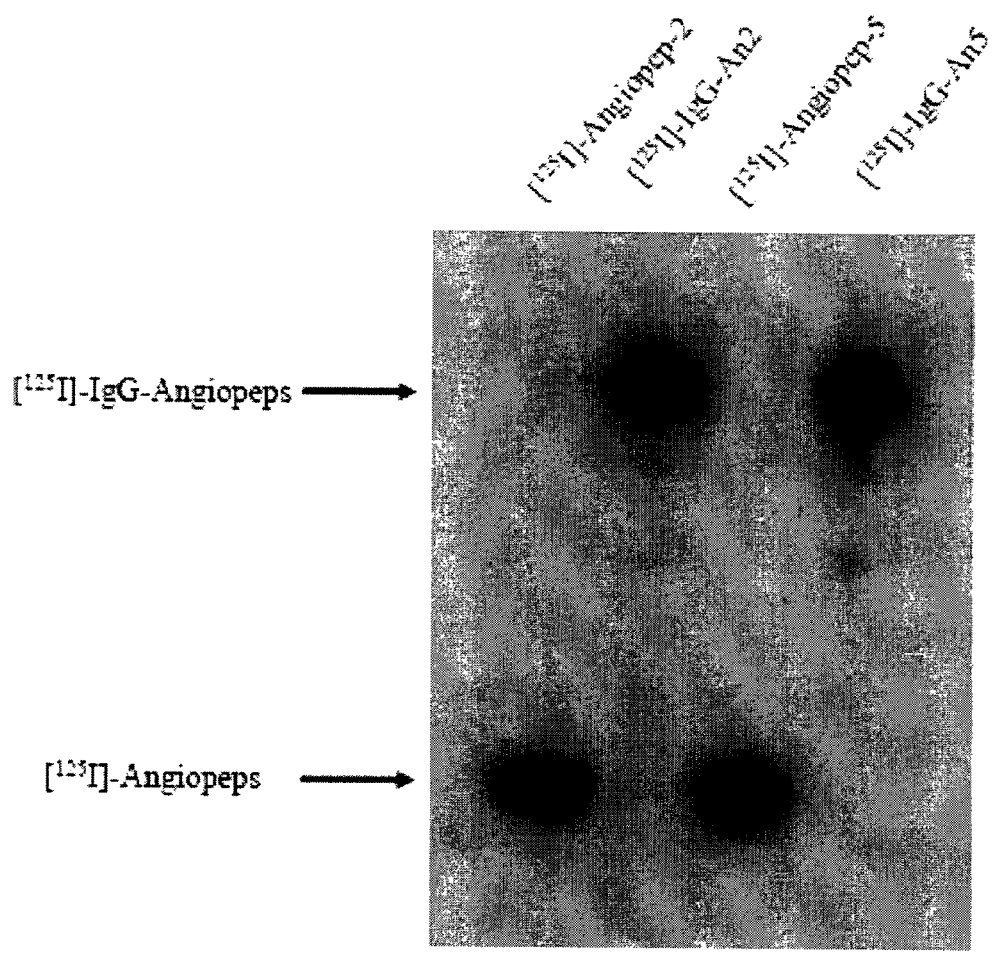
FIG. 29 illustrates an autoradiogram of radiolabeled [$^{125}$I]-IgG-Angiopep conjugates.

Following conjugation of IgG with vectors, SDS-polyacrylamide gel electrophoresis, immunodetection, and autoradiography were performed to ensure proper conjugation; see, e.g., FIG. 29, which shows only [$^{125}$I]-IgG-Angiopep conjugates were detected. There was no evidence of free Angiopep-2 conjugate, showing the efficiency of the conjugation approach.

EXAMPLE 12

Coupling of an Anti-EGFR Antibody to a Vector

Signaling via the epidermal growth factor receptor induces cell proliferative signals and is associated with the transformation of normal to malignant cells. Several mutations in EGFR may be detected in tumor cells. One of the most common mutation of EGFR is the EGFRvIII mutation wherein amino acids 6-273 are deleted.

Figure 30:
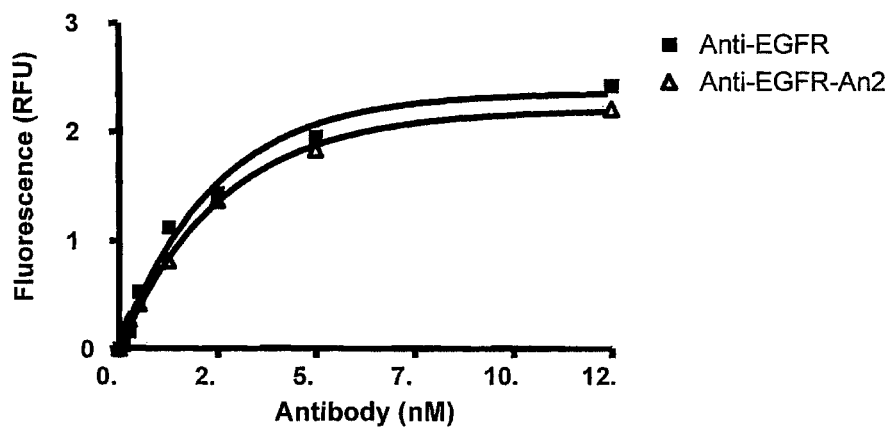
FIG. 30 illustrates the similar detection of EGFR on U87 cells with anti-EGFR and anti-EGFR-Angiopep-2 conjugate by FACS analysis.

To show that coupling of vectors of the invention to antibodies other than IgG was possible, and that coupling maintained the antibody function, an EGFR antibody (monoclonal 528 available from ATCC) was cross-linked to the vector using the cross-linker SATA as an exemplary therapeutic polypeptide. The biological activity of the coupled EGFR antibody was tested by staining EGFR positive U87 cells. Similar detection of EGFR in U87 using both uncoupled and coupled EGFR antibodies by FACS analysis was demonstrated (FIG. 30) showing that coupling of the antibodies of the vectors of the invention did not alter their activity.

In Table 8, we show that the antibodies are not inactivated by conjugation and present the same affinity for binding in an in vitro assay.

TABLE 8

Kinetics analysis of the conjugate binding to EGFR receptor by FACS

|  | Anti-EGFR | Anti-EGFR-Angiopep-2 |
|---|---|---|
| Bmax (RFU) | 23.6 | 22.0 |
| Half saturation (nM) | 1.7 | 1.8 |

Transport of EGFR antibody conjugates (e.g., anti-EGFR-Angiopep-2) across the BBB was then measured using a labeled conjugate. The uptake of anti-[$^{125}$I]-EGFR-Angiopep-2 to the luminal side of mouse brain capillaries was measured using the in situ brain perfusion method as shown in FIG. 31. There was higher brain uptake for [$^{125}$I]EGFR-Angiopep-2 conjugate than that of unconjugated [$^{125}$I]-EGFR Ab in all tissues tested. Therefore, the conjugation of EGFR Ab with Angiopep-2 increases its accumulation in the brain parenchyma in vivo. These conjugates represent an interesting avenue as several different tumor types were show to express EGFR at various levels (see Table 9).

TABLE 9

| Tumor type | Tumors with expressed EGFR (%) |
|---|---|
| Head and Neck | 90-95 |
| Breast | 82-90 |
| Renal carcinoma | 76-89 |
| Cervix/uterus | 90 |
| Esophagael | 43-89 |
| Pancreatic | 30-89 |
| Non-small-cell lung | 40-80 |
| Prostate | 40-80 |
| Colon | 25-77 |
| Ovarian | 35-70 |
| Glioma | 40-63 |
| Bladder | 31-48 |
| Gastric | 4-33 |

EXAMPLE 13

Coupling and Transport of an Anti-VEGF Antibody to a Vector

To further demonstrate the versatility and applicability of antibody coupling to vectors of the invention, another exemplary therapeutic antibody, Avastin, was used. Avastin is an anti-VEGF recombinant humanized monoclonal IgG1 kappa isotype antibody available from Roche Biochemical which binds to and inhibits biologically active forms of vascular endothelial growth factor (VEGF).

Figure 32:
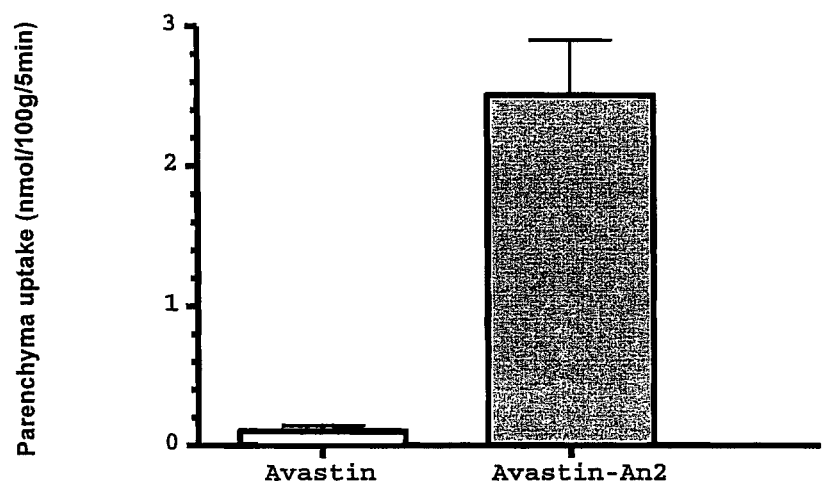
FIG. 32 illustrates the distribution volume in the brain parenchyma of free and Angiopep-2 conjugated VEFG antibody.

Following conjugation, the transport of Avastin conjugates across the BBB was then measured using the in situ brain perfusion method. There is higher brain uptake for [$^{125}$I] Avastin-Angiopep-2 conjugate than that of unconjugated [$^{125}$I]-Avastin (FIG. 32).

Conjugation of therapeutic antibodies (such as Avastin or MAb 528 available from ATCC) to vectors (e.g., Angiopep-1, -2, -3, -4a, -4b, 5, and 6) is therefore a useful strategy for their transport into the brain.

EXAMPLE 14

Dimer Transport

Vector dimers can also be transported. In one example, Angiopep-1 was incubated at 4° C. for at least 12 hours, thereby causing multimerization/dimerization of the polypeptide. The transcytosis capacity of the Angiopep-1 dimer was evaluated in vitro. Angiopep-1 dimer is transcytosed better than IgG. Moreover, as shown in Table 5, the dimeric form of Angiopep-1 shows a distribution volume higher than that of Angiopep-1. Thus, vector dimers can be transported across the BBB.

EXAMPLE 15

Conjugation of an Antibody to More than One Vector

Typically, cross-linking reactions yield between 1 to 6 molecules of vector per one molecule of antibody, heavy and light chains.

The level of conjugation of Angiopep-2 to IgGs was estimated using an assay allowing titration of the amount of sulfhydryl groups after deprotection of SATA on the amine of the IgGs before and after reaction with the maleimide group on the N terminal of Angiopep-2. By changing the relative concentration of the different reactants used in the conjugation protocol the amount of Angiopep-2 conjugated to IgGs may be optimized.

Figure 33:
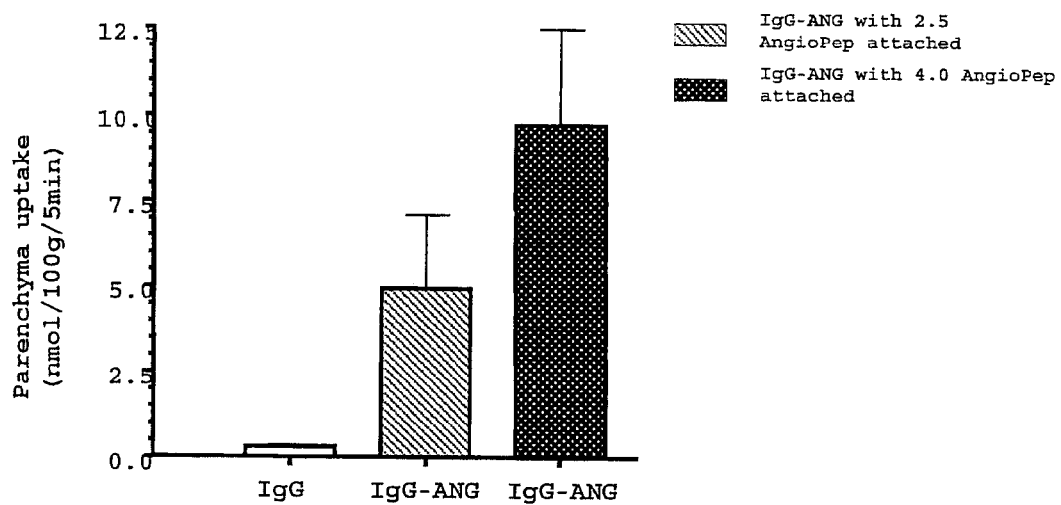
FIG. 33 illustrates the uptake of conjugates including different ratios of vector to the agent (antibody) in the parenchyma.

Using in vivo brain perfusion experiments, the higher the level of conjugation, the higher was the parenchymal uptake of conjugates (FIG. 33). Therefore, it may be desirably to have a larger number of vector per molecule. As such, more than 6 vectors may be used for transporting a compound (agent) across the BBB.

Other Embodiments

The content of each publication, patent, and patent application mentioned in the present application is incorporated by reference, including U.S. application Ser. No. 11/807,597, filed May 29, 2007, and Ser. No. 11/807,917, filed May 30, 2007, and U.S. Provisional Application No. 61/008,825, filed Dec. 20, 2007.

Although the invention has been described in details herein and illustrated in the accompanying drawings, it is to be understood that the invention is not limited to the embodiments described herein and that various changes and modifications may be effected without departing from the scope or spirit of the invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A polypeptide comprising an amino acid sequence having the amino acid sequence of Angiopep-7 (SEQ ID NO: 112) wherein said polypeptide is transported to at least one cell or tissue selected from the group consisting of liver, lung, kidney, spleen, and muscle.

2. The polypeptide of claim 1, wherein said polypeptide consists of the amino acid sequence of Angiopep-7 (SEQ ID NO: 112).

3. A composition comprising the polypeptide of claim 1.

4. The composition of claim 3 comprising a pharmaceutically acceptable carrier.

5. A conjugate comprising:
   (a) a vector comprising a polypeptide of claim 1; and
   (b) a therapeutic agent, diagnostic agent, or detectable label, wherein said agent or label is conjugated to said vector.

6. The conjugate of claim 5, wherein said vector consists of a polypeptide consisting of the amino acid sequence of Angiopep-7 (SEQ ID NO:112).

7. The conjugate of claim 5, wherein said vector is conjugated to a therapeutic agent.

8. The conjugate of claim 5, wherein said therapeutic agent is an anticancer agent.

9. The conjugate of claim 8, wherein said anticancer agent is selected from the group consisting of abarelix, aldesleukin, alitertinoin, allopurinol, altretamine, amifostine, anakinra, anastrozole, arsenic trioxide, asparaginase, azacitidine, BCG Live, bexarotene, bleomycin, bortezomib, busulfan, calusterone, capecitabine, carboplatin, carmustine, zoledronic, chlorambucil, cisplatin, cladribine, clofarabine, cyclophosphamide, cytarabine, dacarbazine, dactinomycin, actinomycin D, dalteparin, darbepoetin alfa, dasatinib, daunorubicin, daunomycin, decitabine, denileukin, Denileukin diftitox, dexrazoxane, docetaxel, doxorubicin, dromostanolone propionate, epirubicin, epoetin alfa, erlotinib, estramustine, etoposide, exemestane, fentanyl, filgrastim, floxuridine, fludarabine, fluorouracil, 5-FU, fulvestrant, gefitinib, gemcitabine, goserelin, histrelin, hydroxyurea, idarubicin, ifosfamide, imatinib, Interferon alfa-2b, irinotecan, lapatinib ditosylate, lenalidomide, letrozole, leucovorin, leuprolide, levamisole, lomustine, CCNU, meclorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, oprelvekin, oxaliplatin, paclitaxel, palifermin, pamidronate, pegademase, pegaspargase, pegfilgrastim, peginterferon alfa-2b, pemeterxed, pentostatin, pipobroman, plicamycin (mithramycin), porfimer, procarbazine, quinacrine, rasburicase, sargramostim, sorafenib, streptozocin, sunitinib, sunitinib maleate, talc, tamoxifen, temozolomide, teniposide (VM-26), testolactone, thalidomide, thioguanine (6-TG), thiotepa, thiotepa, thiotepa, topotecan, toremifene, tretinoin (ATRA), uracil mustard, valrubicin, vinblastine, vincristine, vinorelbine, vorinostat, zoledronate, and zoledronic acid.

10. The conjugate of claim 9, wherein said agent is paclitaxel.

11. The conjugate of claim 5, wherein said vector is not efficiently transported across the BBB.

12. The conjugate of claim 5, wherein said conjugate accumulates more rapidly, accumulates to a higher concentration, exhibits reduced P-gp mediated efflux in a liver, lung, kidney, or spleen cell, as compared to said agent or label when not conjugated to said vector.

13. A composition comprising the conjugate of claim 5 and a pharmaceutically acceptable carrier.

* * * * *

```
SEQUENCE LISTING

<160> NUMBER OF SEQ ID NOS: 112

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Ser Phe Tyr Tyr Gly Gly Cys Leu Gly Asn Lys Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: may be amidated

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Phe Phe Tyr Gly Gly Ser Arg Gly Lys Gly Asn Asn Phe Asp Arg
1               5                   10                  15

Ala Lys Tyr
```

```
<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Phe Phe Tyr Gly Gly Cys Gly Gly Asn Lys Asn Asn Phe Val Arg
1               5                   10                  15

Glu Lys Tyr
```

```
<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Phe Phe Tyr Gly Gly Cys Leu Gly Asn Arg Asn Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Phe Phe Tyr Gly Gly Cys Leu Gly Asn Arg Asn Asn Phe Val Arg
1               5                   10                  15

Glu Lys Tyr

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Phe Phe Tyr Gly Gly Cys Leu Gly Asn Lys Asn Asn Tyr Val Arg
1               5                   10                  15

Glu Lys Tyr
```

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Phe Phe Tyr Gly Gly Cys Leu Gly Asn Arg Asn Asn Phe Asp Arg

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

```
Met Arg Pro Asp Phe Cys Leu Glu Pro Pro Tyr Thr Gly Pro Cys Val
1               5                   10                  15

Ala Arg Ile
```

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Ala Arg Ile Ile Arg Tyr Phe Tyr Asn Ala Lys Ala Gly Leu Cys Gln
1               5                   10                  15

Thr Phe Val Tyr Gly
            20
```

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Tyr Gly Gly Cys Arg Ala Lys Arg Asn Asn Tyr Lys Ser Ala Glu Asp
1               5                   10                  15

Cys Met Arg Thr Cys Gly
            20
```

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Pro Asp Phe Cys Leu Glu Pro Pro Tyr Thr Gly Pro Cys Val Ala Arg
1               5                   10                  15

Ile Ile Arg Tyr Phe Tyr
            20
```

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: may be amidated

<400> SEQUENCE: 67

```
Thr Phe Phe Tyr Gly Gly Cys Arg Gly Lys Arg Asn Asn Phe Lys Thr
1               5                   10                  15

Glu Glu Tyr
```

<210> SEQ ID NO 68
<211> LENGTH: 19
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20
```

```
<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: may be amidated

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

```
Thr Phe Phe Tyr Gly Gly Lys Arg Gly Lys Arg Asn Asn Phe Lys Thr
1               5                   10                  15

Glu Glu Tyr
```

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Thr Phe Phe Tyr Gly Gly Cys Arg Gly Lys Arg Asn Asn Phe Lys Thr
1               5                   10                  15

Lys Arg Tyr
```

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Thr Phe Phe Tyr Gly Gly Lys Arg Gly Lys Arg Asn Asn Phe Lys Thr
1               5                   10                  15

Ala Glu Tyr
```

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Thr Phe Phe Tyr Gly Gly Lys Arg Gly Lys Arg Asn Asn Phe Lys Thr
1               5                   10                  15

Ala Gly Tyr
```

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Thr Phe Phe Tyr Gly Gly Lys Arg Gly Lys Arg Asn Asn Phe Lys Arg
1               5                   10                  15

Glu Lys Tyr
```

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Phe Phe Tyr Gly Gly Cys Leu Gly Asn Arg Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: may be amidated

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr
```

```
<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
            20                  25                  30

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<300> PUBLICATION INFORMATION:
<310> PATENT DOCUMENT NUMBER: US 5,780,265
<311> PATENT FILING DATE: 1995-07-05
<312> PUBLICATION DATE: 1998-07-14

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
            20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
```

```
<220> FEATURE:
<223> OTHER INFORMATION: synthetic construct

<400> SEQUENCE: 106
atgagaccag atttctgcct cgagccgccg tacactgggc cctgcaaagc tcgtatcatc    60
cgttacttct acaatgcaaa ggcaggcctg tgtcagacct tcgtatacgg cggctgcaga   120
gctaagcgta caacttcaa atccgcggaa gactgcatgc gtacttgcgg tggtgcttag    180

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: may be acetylated

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: may be acetylated

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: may be acetylated

<400> SEQUENCE: 110
```

```
Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Phe Phe Tyr Gly Gly Ser Arg Gly Arg Arg Asn Asn Phe Arg Thr
1               5                   10                  15

Glu Glu Tyr
```